United States Patent [19]

Berliner et al.

[11] Patent Number: 5,563,131

[45] Date of Patent: Oct. 8, 1996

[54] PREGNANE STEROIDS AS NEUROCHEMICAL INITIATORS OF CHANGE IN HUMAN HYPOTHALAMIC FUNCTION AND RELATED PHARMACEUTICAL COMPOSITIONS AND METHODS

[75] Inventors: David L. Berliner, Atherton, Calif.; Clive L. Jennings-White; Nathan W. Adams, both of Salt Lake City, Utah

[73] Assignee: Pherin Corporation, Menlo Park, Calif.

[21] Appl. No.: 286,073

[22] Filed: Aug. 4, 1994

[51] Int. Cl.[6] .................................................. A61K 31/56
[52] U.S. Cl. .......................... 514/177; 514/178; 514/182
[58] Field of Search .................................. 514/177, 178, 514/182

[56] References Cited

U.S. PATENT DOCUMENTS 5,155,045  10/1992  Cutler et al. ............................. 436/65

FOREIGN PATENT DOCUMENTS

| 7028114 | 7/1970 | France . |
| 1297603 | 8/1964 | Germany . |
| 32-30081 | 12/1957 | Japan . |
| 40-3445 | 1/1965 | Japan . |
| 287863 | 1/1963 | Netherlands . |
| 6514465 | 11/1965 | Netherlands . |

*Primary Examiner*—Kimberly Jordan
*Attorney, Agent, or Firm*—Fish & Richardson P.C.

[57] ABSTRACT

The invention relates to a method of altering hypothalamic function in an individual. The method comprises nasally administering a human vomeropherin, e.g. a pregnane steroid, or a pharmaceutical composition containing a vomeropherin, such that the vomeropherin binds to a specific neuroepithelial receptor. The steroid or steroids is/are preferably administered in the form of a pharmaceutical composition containing one or more pharmaceutically acceptable carriers. Other embodiments of the invention include pharmaceutical compositions containing the steroids.

30 Claims, 31 Drawing Sheets

PREGNANE STEROIDS AS NEUROCHEMICAL INITIATORS OF CHANGE IN HUMAN HYPOTHALAMIC FUNCTION AND RELATED PHARMACEUTICAL COMPOSITIONS AND METHODS

CROSS-REFERENCE TO RELATED APPLICATIONS

This application is related to U.S. application Ser. No. 08/127,908, filed Sep. 28, 1993 which is a continuation-in-part of U.S. application Ser. No. 07/903,604, filed 24 Jun. 1992, which in turn is a continuation-in-part of U.S. application Ser. No. 07/708,936, filed 31 May 1991, which in turn is a continuation-in-part of U.S. application Ser. No. 07/638,185, filed 7 Jan. 1991, now abandoned.

The application also relates to U.S. application Ser. No. 08/127,980 filed Sep. 28, 1993 which is another continuation-in-part of U.S. patent application Ser. No. 07/903,604, U.S. patent application Ser. No. 08/077,359, filed 15 Jun. 1993, and to commonly assigned, co-pending U.S. patent application Ser. No. 07/903,525, filed 24 Jun. 1992 (a continuation-in-part of U.S. application Ser. No. 07/707,862, filed 31 May 1991, which in turn is a continuation-in-part of U.S. application Ser. No. 07/638,743, filed 7 Jan. 1991, now abandoned) entitled "Estrene Steroids as Neurochemical Initiators of Change in Human Hypothalamic Function and Related Pharmaceutical Compositions and Methods"; and to the commonly assigned, co-pending continuation-in-part of 07/903,525, U.S. patent application Ser. No. 08/077,140. The aforementioned U.S. patent applications are each incorporated herein by reference.

Finally, this application may relate to U.S. Pat. No. 5,278,141, issued Jan. 11, 1994 entitled "Fragrance Compositions Containing Human Pheromones", and U.S. Pat. No. 5,272,134, issued Dec. 21, 1993, entitled "Fragrance Compositions and Other Compositions which Contains Human Pheromones."

TECHNICAL FIELD

This invention relates generally to pharmaceutical compositions and methods for effectuating change in human hypothalamic function, thereby altering certain behavior and physiology mediated by the hypothalamus of individuals. More particularly, the invention relates to the use of certain pregnane steroids as neurochemical effectuators of physiology and behavior.

DESCRIPTION OF THE RELATED ART

The present invention relates to certain compounds, namely pregnane steroids, particularly pregnane steroids and related compounds as will be described herein, and methods of using these compounds as human vomeropherins in order to alter hypothalamic function, thereby affecting certain consequent behavior and physiology, e.g., the reduction of anxiety. Pregnane steroids are characterized by a four ring steroidal structure, a methylation at the 13-position and at the 10-position, and ethylation at the 17-position. Pregnenes are a subset of pregnanes and have at least one double bond. Ohloff, G. et al. (*Helv. Chim. Acta* (1983) 66:192–217), which is incorporated herein by reference, have shown that several steroids (androstenes) have an odor which varies with different isomeric, diastereomeric, and enantiomeric forms. Some members of this group have been reported to act as a pheromone in some mammalian species—for instance, 5α-androst-16-en-3-one and 5α-androst-16-en-3α-ol in pigs (Melrose, D. R., et al., *Br. vet. J.* (1971) 127:497–502). These 16-androstenes produced by the boar induce mating behavior in estrus sows (Claus, et al., *Experimentia* (1979) 35:1674–1675).

Some studies have noted that, in some species, various characteristics of certain 16-androstenes (including 5α-Androst-16-en-3α-ol and 5α-Androst-16-en-3-one), such as concentration, metabolism, and localization, are sexually dimorphic (Brooksbank et al., *J. Endocr.* (1972) 52: 239–251; Claus, et al., *J. Endocr.* (1976) 68:483–484; Kwan, et al., *Med. Sci. Res.* (1987) 15:1443–1444). For instance, 5α-Androst-16-en-3α-ol and 5α-Androst-16-en-3-one, as well as Androsta-4,16-dien-3-one, have been found at different concentrations in the peripheral blood, saliva and axillary secretions of men and of women (Kwan, T. K., et al., *Med. Sci. Res.* (1987) 15:1443–1444), and their function as a human pheromone, to the extent of affecting choice and judgement, has been suggested (Id.; see also Gower, et al., "The Significance of Odorous Steroids in Axillary Odour", In, *Perfumery*, pp 68–72, Van Toller and Dodd, Eds., Chapman and Hall, 1988); Kirk-Smith, D. A., et al., *Res. Comm. Psychol. Psychiat. Behav.* (1978) 3:379). Androstenol (5α-androst-16-en-3α-ol) has been claimed to exhibit a pheromone-like activity in a commercial men's cologne and women's perfume (Andron™ for men and Andron™ for women by Jovan). Japanese Kokai No. 2295916, refers to perfume compositions containing androstenol and/or its analogues. Androstadien-3β-ol (and perhaps the 3α-ol) has also been identified in human axillary secretion (Gower, et al., Supra at 57–60. On the other hand, there is little agreement in the literature as to whether or not any putative pheromone actually plays any role in the sexual or reproductive behavior of mammals, particularly of humans. See: Beauchamp, G. K., et al., "The Pheromone Concept in Mammalian Chemical Communication: A Critique", In: *Mammalian Olfaction, Reproductive Processes and Behavior*, Doty, R. L., Ed., Academic Press, 1976). See also: Gower, et al., supra at 68–73.

The pheromone properties of some estrene steroids for some mammalian species has been described. Michael, R. P. et al., *Nature* (1968) 218:746 refers to Estrogens (particularly Estradiol) as a pheromonal attractant of male rhesus monkeys. Parrot, R. F., *Hormones and Behavior* (1976) 7:207–215, reports Estradiol benzoate injection induces mating behavior in ovariectomized rats; and the role of the blood level of Estradiol in make sexual response (Phoenix, C. H., *Physiol. and Behavior* (1976) 16:305–310) and female sexual response (Phoenix, C. H., *Hormones and Behavior* (1977) 8:356–362) in Rhesus monkeys has been described. On the other hand, there is little agreement in the literature as to whether or not pheromones as such play any role in the reproductive behavior and interpersonal communication of mammals (Beuchamp, G. K., et al., "The Pheromone Concept in Mammalian Chemical Communication: A Critique", In: *Mammalian Olfaction, Reproductive Processes, and Behavior*, Doty, R. L., Ed., Academic Press, 1976).

An embodiment of the subject invention concerns the non-systemic, nasal administration of certain pregnane and pregnene steroids to affect a specific behavioral or physiological response in human subjects, e.g., a reduction of negative affect, mood, and character traits. In particular, nasal administration provides for contacting neurochemical receptors of a heretofore poorly understood neuroendocrine structure, commonly known as the vomeronasal organ ("VNO"; also known as "Jacobson's organ"), with one or more steroid(s) or with compositions containing the steroid(s). This organ is accessed through the nostrils of most higher animals—from snakes to humans, and has been associated, inter alia, with pheromone reception in certain species (see generally Muller-Schwarze & Silverstein, *Chemical Signals*, Plenum Press, New York (1980)). The axons of the neuroepithelia of the vomeronasal organ, located supra palatinal, form the vomeronasal nerve and have direct synaptic connection to the accessory olfactory bulb and indirect input from there to the cortico-medial amygdaloid basal forebrain and hypothalamic nuclei of the brain. The distal axons of terminalis nerve neurons may also serve as neurochemical receptors in the VNO. Stensaas, L. J., et al., *J. Steroid Biochem. and Molec. Biol.* (1991) 39:553. This nerve has direct synaptic connection with the hypothalamus.

Johnson, A. et al. (*J. Otolaryngology* (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., supra; and by Moran, D. T., et al., Garcia-Velasco, J. and M. Mondragon; Monti-Bloch, L. and B. Grosser all in *J. Steroid Biochem. and Molec. Biol.* (1991) 39.

It is apparent that it would be desirable to identify and synthesize human vomeropherins and pheromones and to develop pharmaceutical compositions and methods of use to influence hypothalamic function. This invention relates to the unexpected discovery that, when nasally administered to human subjects, certain neurochemical ligands, particularly pregnane steroids, pregnene steroids and related compounds, or pharmaceutical compositions containing pregnanes, pregnenes or related compounds, specifically bind to chemoreceptors of certain nasal neuroepithelial cells and this binding generates a series of neurophysiological responses resulting in an alteration of hypothalamic function of an individual. When properly administered, the effect of certain of these compounds on the hypothalamus affects the function of the autonomic nervous system and a variety of behavioral- or physiological phenomena which include, but are not limited to the following: anxiety, premenstrual stress, fear, aggression, hunger, blood pressure, and other behavioral and physiological functions normally regulated by the hypothalamus. See Otto Appenzeller, *The Autonomic Nervous System. An introduction of basic and clinical concepts* (1990); Korner, P. I. *Central nervous control of autonomic cardiovascular function*, and Levy, N. M. and Martin, P. J. *Neural control of the heart*, both in *Handbook of Physiology: Section 2: Cardiovascular System—the heart*, Vol I, Washington D.C., 1979, American Physiological Society; Fishman, A. P., et al. editors, *Handbook of Physiology. Section 3: Respiratory System. Vol. II. Control of breathing*, Bethesda Md. 1986. American Physiological Society.

In some instances a single pregnane steroid, or related compound, is administered, in some instances combinations of pregnane steroids and/or related compounds are administered and in some instances one or more pregnane steroids are co-administered along with one or more estrane or estrene steroids, androstane or androstene steroids or a related compound.

SUMMARY OF THE INVENTION

Accordingly, it is an object of this invention to provide pharmaceutical compositions which contain human vomeropherins or pheromones and are suitable for nasal administration in an individual.

It is also an object of this invention to provide methods of using these compositions to alter hypothalamic function of an individual.

It is a further object of this invention to provide methods of using these compositions to affect physiological and behavioral functions of individuals which are normally regulated by the hypothalamus.

Finally, it is an object of this invention to provide methods of altering hypothalamic function which have the following advantages: 1) administration directly to the chemoreceptors in the nasal passage and the romeronasal organ, without pills or needles—i.e., non-invasively; 2) a mode of drug action through the nervous system and not through the circulatory system—thus brain function can be affected without consideration of the blood-brain barrier; 3) a direct means of affecting the hypothalamus—there is only one synaptic junction between pheromone receptors and the hypothalamus; and, 4) providing a highly specific drug effect, thereby greatly reducing the potential for undesirable side-effects—this because sensory nerves are addressed to a specific location in the brain.

Additional objects, advantages and novel features of the invention will be set forth in part in the description which follows, and in part will become apparent to those skilled in the art upon examination of the following, or may be learned by practice of the invention.

Objects of this invention are achieved by providing a pharmaceutical composition suitable for nasal administration in an individual. The composition contains a pharmaceutically acceptable carrier and a pregnane steroid with the formula:

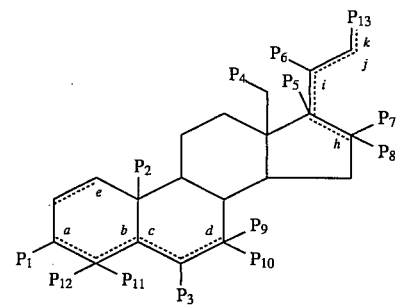

wherein $P_1$ is selected from the group consisting of oxo, $\alpha$-($\beta$-)hydroxy, $\alpha$,($\beta$-)acetoxy, $\alpha$-($\beta$-)propionoxy, $\alpha$-($\beta$-)methoxy, $\alpha$-($\beta$-)lower acyloxy, $\alpha$-($\beta$-) lower alkyloxy, and $\alpha$-($\beta$-)benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, oxo, halo, hydroxy, alkoxy, and acyloxy; $P_4$ through $P_{12}$ may each be, independently, hydrogen, halo, methyl, or halo-, dihalo-, or perhalomethyl and when $P_2$ is methyl and $P_3$ is $\beta$-hydroxy, $P_2$ and $P_3$ may be jointed to form a cylic ether; $P_{13}$ is hydrogen, methyl, methylene, halo-substituted methyl or halo-substituted methylene; and "a", "b", "c", "d", "e", "h", "i", and "j" are alternative sites for optional double bonds, and "j" may also be a triple bond. Halo substituents include fluoro, bromo, chloro and iodo atoms.

One class of preferred steroids has "b" as a double bond, particularly wherein "d" or "e" is also a double bond. Another preferred class has "a" and "c" as double bonds, or only "c" as a double bond. Yet another preferred class contains "h" as a double bond, with i and j being absent (i.e., single bonds), j being a double bond, or j being a triple bond. In another class, "h" is absent, and j or i is a double bond, or i and j are absent, or j and i are double bonds, or j is a triple bond.

The term lower alkyl, lower alkoxy, etc., is meant to encompass carbon chains of 1 to 6 carbon atoms, preferably 1 to 4 carbon atoms.

Other objects of this invention are achieved by providing a method of altering hypothalamic function and/or autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence, whether or not the modified steroids are explicitly disclosed.

DETAILED DESCRIPTION OF THE INVENTION

I. Definitions

Figure 1A:
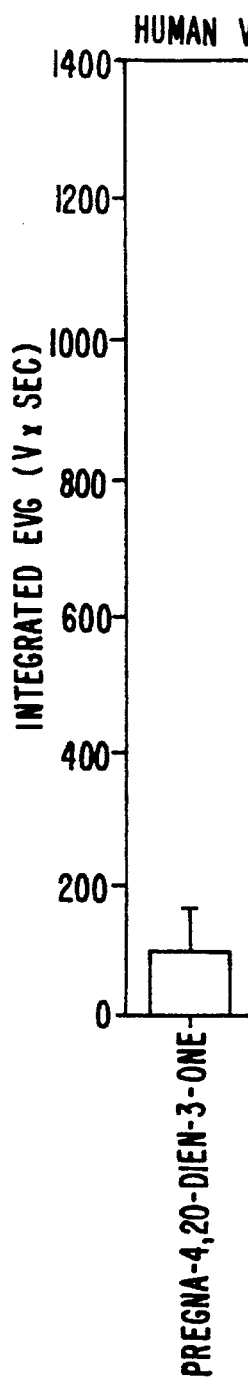
FIG. 1 is the data on the integrated EVG, GSR and ST for compound A1-P1 in males as tested according to Examples 16 and 17.

An "affect" is a transient feeling state. Typical negative affects are feelings of nervousness, tenseness, shame, anxiousness, irritability, anger, rage, and the like. "Moods" are longer lasting feeling states such as guilt, sadness, hopelessness, worthlessness, remorsefulness, misery, unhappiness and the like. "Character traits" are more permanent aspects of an individual's personality. Typical negative character traits are sensitivity, regretfulness, blameworthiness, stubbornness, resentfulness, bitterness, timidness, laziness and the like.

The vomeropherins according to the present invention may have use for stimulating, through contact with the VNO, of one or more of the hormonal, behavioral and autonomic functions of the hypothalamus. Due to the predominant role played by the hypothalamus in a wide variety of internal body functions and the neural connection between the VNO and the hypothalamus, the vomeropherins according to the present invention are in a position to stimulate such functions as endocrine output control, for example, the control of the pituitary output of vasopressin and oxytocin as well as a number of other peptides. Vasopressin is an anti-diuretic hormone because of its action within the kidney to enhance water uptake and to concentrate the urine. In addition, it has an action within the body to regulate blood pressure through its action on arterial smooth muscle and an action on metabolism through its enhancement of glycogen conversion to glucose in the liver. Oxytocin, receptors of which are found on uterine smooth muscle and on mammary smooth muscle, can cause milk letdown via contraction of the mammary smooth muscle and cause uterine contractions during birth. The hypothalamus also controls release of hormones from the anterior pituitary gland such as ACTH, prolactin, LH (Luteinizing Hormone), GH (Growth Hormone), TSH (Thyroid Stimulating Hormone), FSH (Follicle Stimulating Hormone) and beta-endorphin. Thus, for example, the ability to control LH secretion may lead to control of fertility, in females, or testosterone production in males. Testosterone production may be utilized for treatment of conditions such as low libido in males or for treatment of muscle wasting diseases or conditions, such as aging.

Control of behavioral hypothalamic functions is also feasible by use of the vomeropherins according to the present invention. It is known that the hypothalamus controls such behavioral outputs as fear, rage, pleasure and circadian rhythms which regulate sleep and wakefulness. Other functions controlled by the hypothalamus include appetite, thirst, sympathetic functions such as, flight and fight, and functions such as cardiovascular control, thermoregulation and visceral functions such as control of the gut muscle and acid secretion for digestion. Thus, while there is a multitude of sensory inputs into the hypothalamus from various parts of the anatomy it is believed that the vomeropherins of the present invention provide, for the first time, a way of stimulating through the nasal cavity by inhalation to contact the epithelial cells in the VNO, a method of stimulating functions of the hypothalamus discussed above.

"Pregnane steroids" are aliphatic polycyclic hydrocarbons characterized by a four-ring steroidal structure with a methylation at the 10- and 13-positions and ethylation (including unsaturated groups) at the 17-position. A pregnene is a subset of pregnanes commonly understood to mean that the compound has at least one double bond. Furthermore, all derivatives which have the structural characteristics described above are also referred to generically as pregnane steroids.

A "chemoreceptor" is a receptor molecule displayed on the surface of a "chemosensory" neuroepithelial cell which binds in a stereospecific fashion to a particular ligand or ligands. This specific binding initiates a signal transduction which initiates an afferent nerve impulse. Chemoreceptors are found, inter alia, in taste buds, olfactory epithelium and vomeronasal tissue.

"Pregnene steroids", as the term is used herein, are aliphatic polycyclic hydrocarbons with a four-ring steroidal structure, at least one double bond in the A-ring, methylation at the 10-position and 13-position, ethylation (including unsaturated groups) at the 17-position and an oxo, hydroxyl or hydroxyl derivative such as an alkoxy, ester, benzoate, cypionate, sulfate or glucuronide, at the 3-position. Derivatives which contain these structural characteristics are also referred to generically as pregnene steroids.

The following structure shows the four-ring steroidal structure common to pregnane and pregnene steroids. In describing the location of groups and substituents, the following numbering system will be employed:

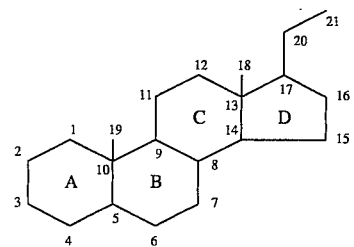

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to an individual in need of the drug. In the present case, a needy individual is one with a physiological or behavioral trait which is normally regulated by the hypothalamus and wherein it is desirable to affect the function of the hypothalamus or the trait. The effective amount of a given drug may vary depending upon the function to be affected, the desired effect, route of administration, and the like. For example, when the steroid is administered as a solution applied to the facial skin of a subject an effective concentration is from 1 microgram/ml to 100 μg/ml, preferably 10 to 50 μg/ml and most preferably 20 to 30 μg/ml. When the steroid is introduced directly into the VNO an effective amount is about 1 picogram to about 1 nanogram, more preferably about 10 picograms to about 50 picograms. When the steroid is administered to the nasal passage, by ointment, cream or aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammallary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the vomeropherin therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a vomeropherin) a summated change in cell surface receptor potential can be measured.

As used herein, "lower alkyl" means a branched or unbranched saturated hydrocarbon chain of 1 to 4 carbons, such as, for example, methyl, ethyl, n-propyl, i-butyl and the like. "Alkoxy" as used herein is used in its conventional sense to mean the group —OR wherein R is alkyl as herein defined.

A "pheromone" is a substance that provides chemical means of communication between members of the same species through secretion and peripheral chemoreception. In mammals pheromones are usually detected by receptors in the vomeronasal organ of the nose. Commonly, pheromones effect development, reproduction and related behaviors. A "vomeropherin" is a more general term which includes pheromones and describes a substance from any source which functions as a chemosensory messenger, binds to a specific vomeronasal neuroepithelial receptor, and induces a physiological or behavioral effect. The physiologic effect of a "vomeropherin" is mediated through the vomeronasal organ.

A picogram (pg) is equal to 0.001 nanograms (ng). A ng is equal to 0.001 micrograms (μg). A μg is equal to 0.001 mg.

II. Modes for Carrying Out the Invention

A. Pregnanes useful in the Invention

The invention is directed to a group of certain pregnane steroids.

A subset of pregnanes within the group are believed to be novel. Syntheses are described herein for the following compounds as designated on the chart:

Chart 1 includes pregnanes to which the invention is directed, but do not limit its scope. The synthesis diagrams that follow depict intermediate and substructure syntheses for the preparation of these pregnanes:

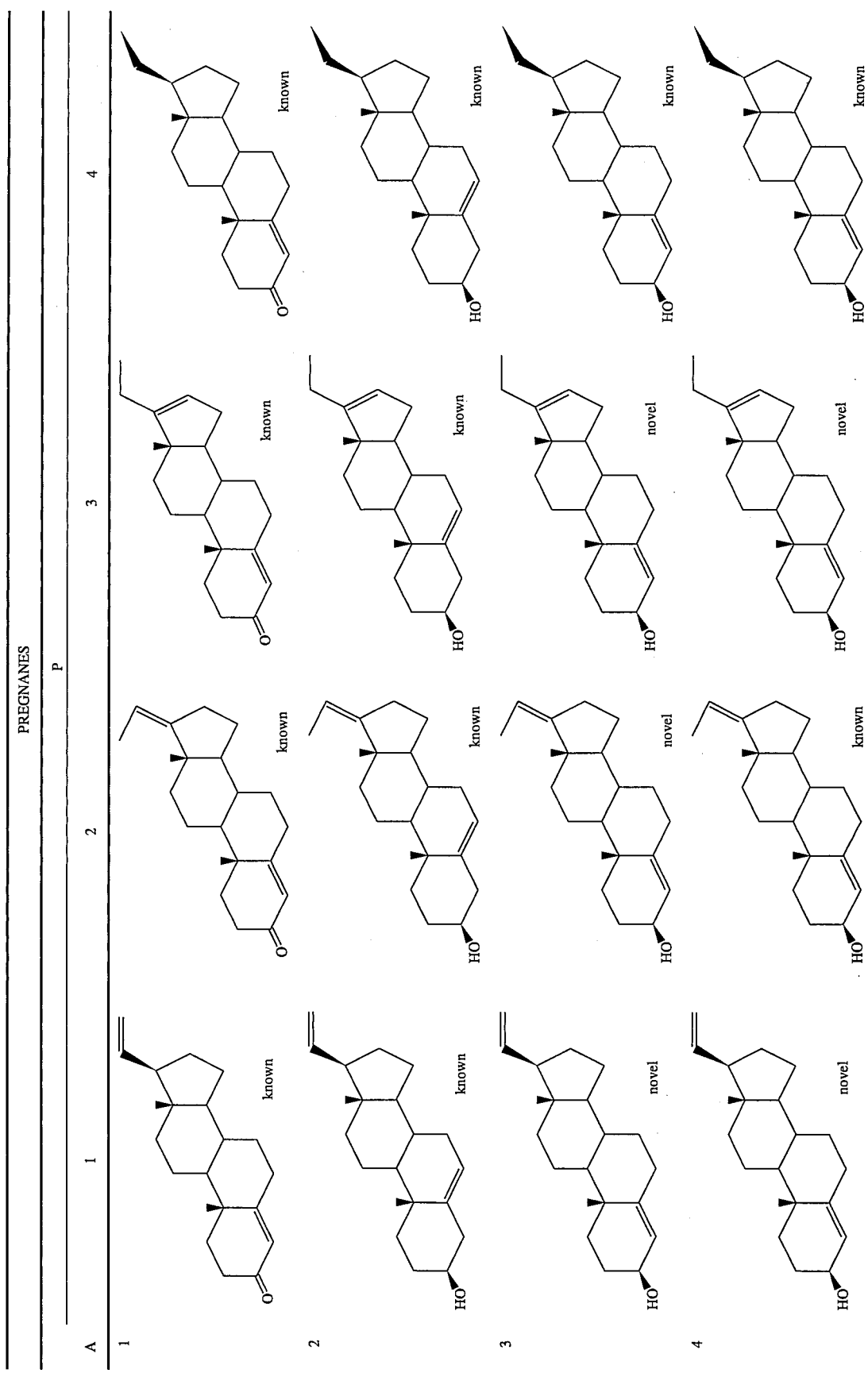

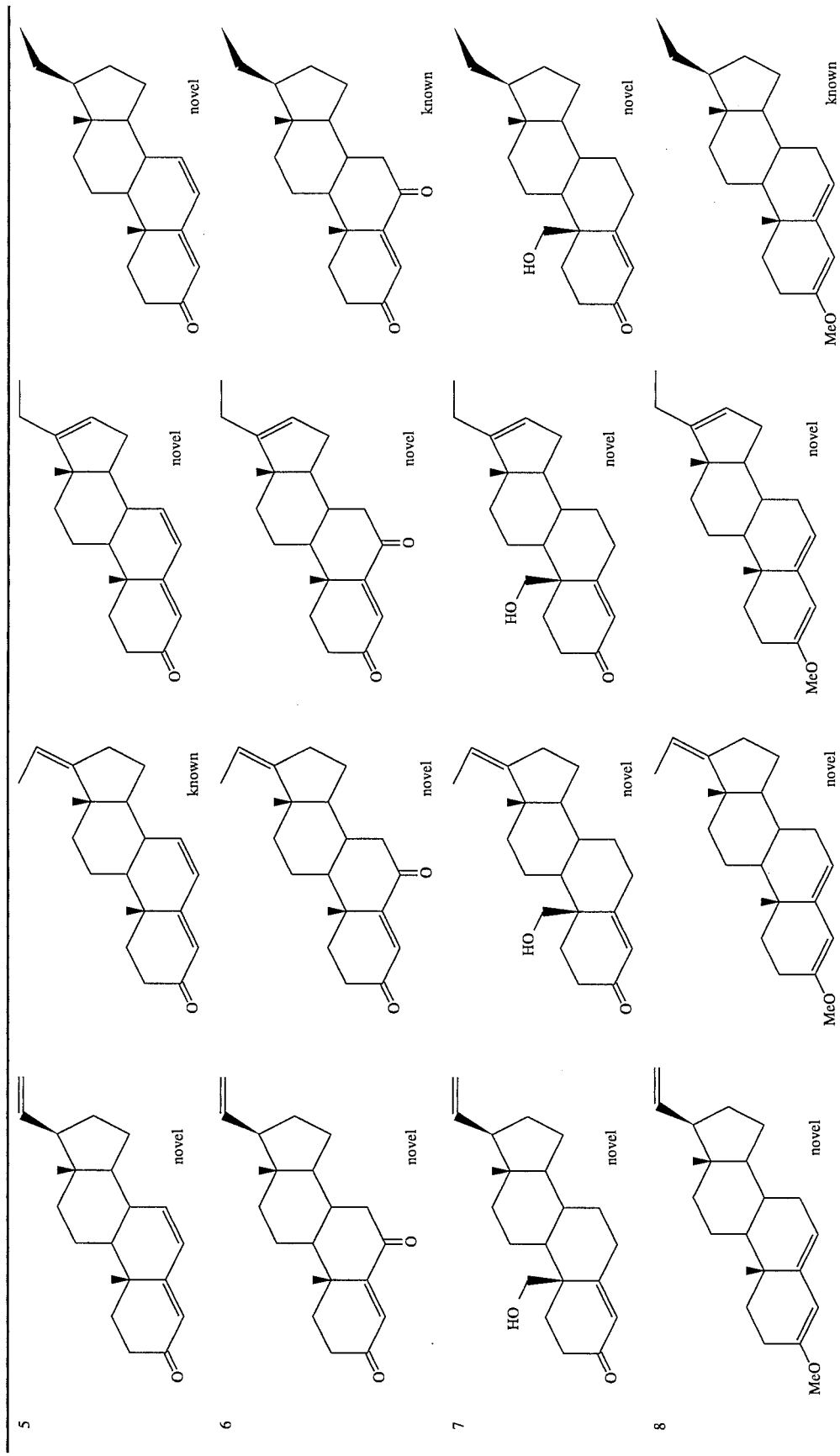

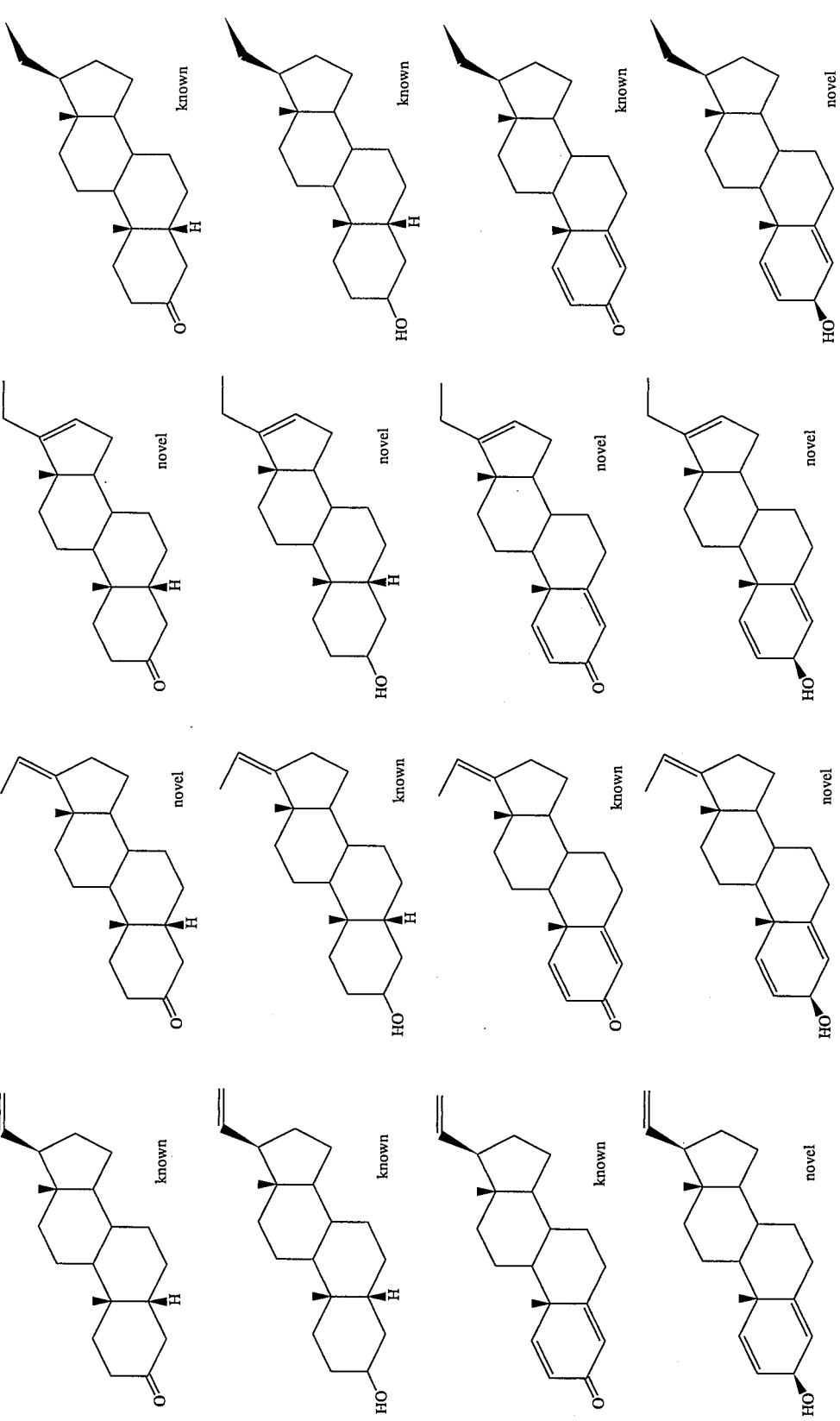

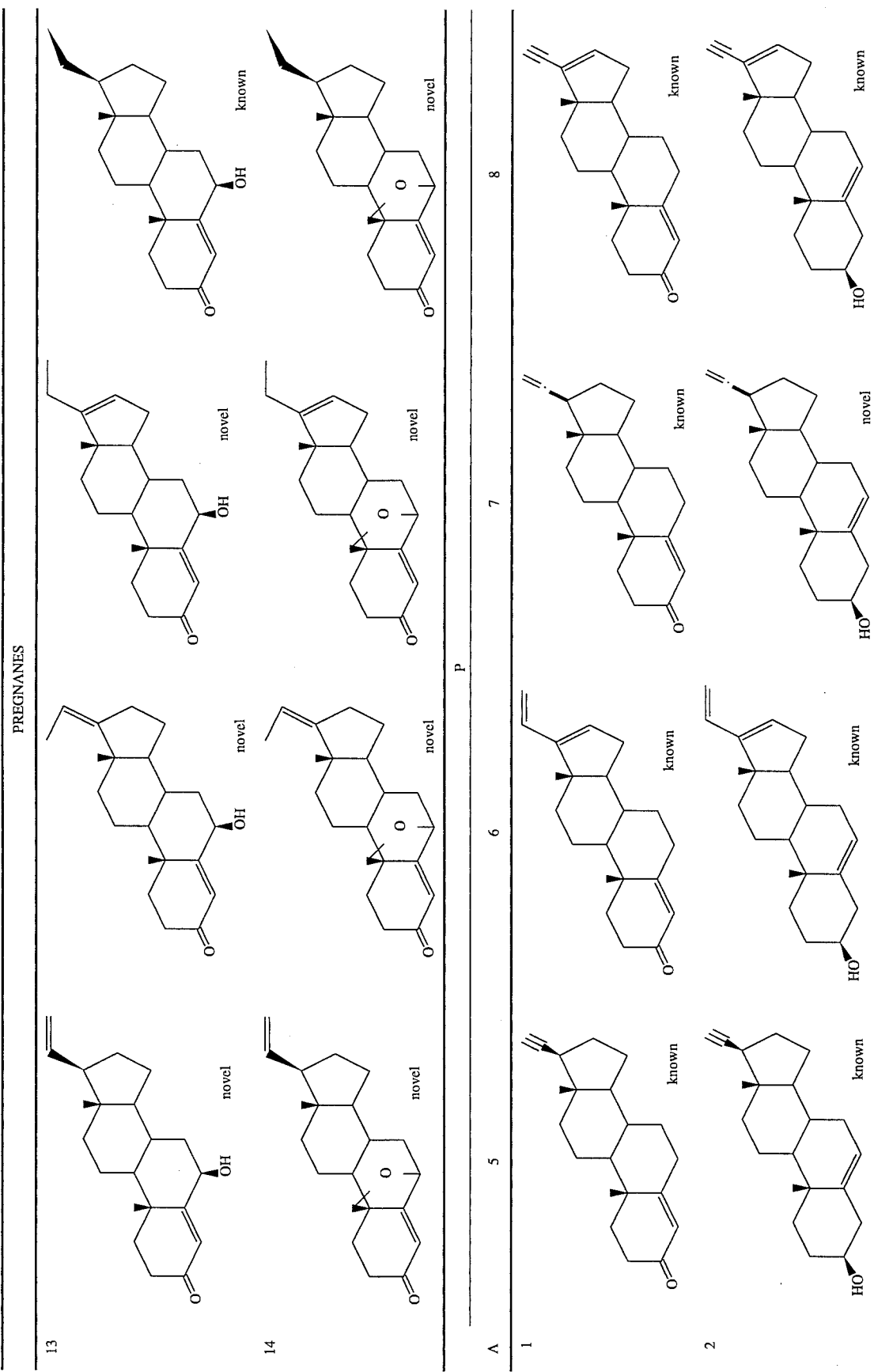

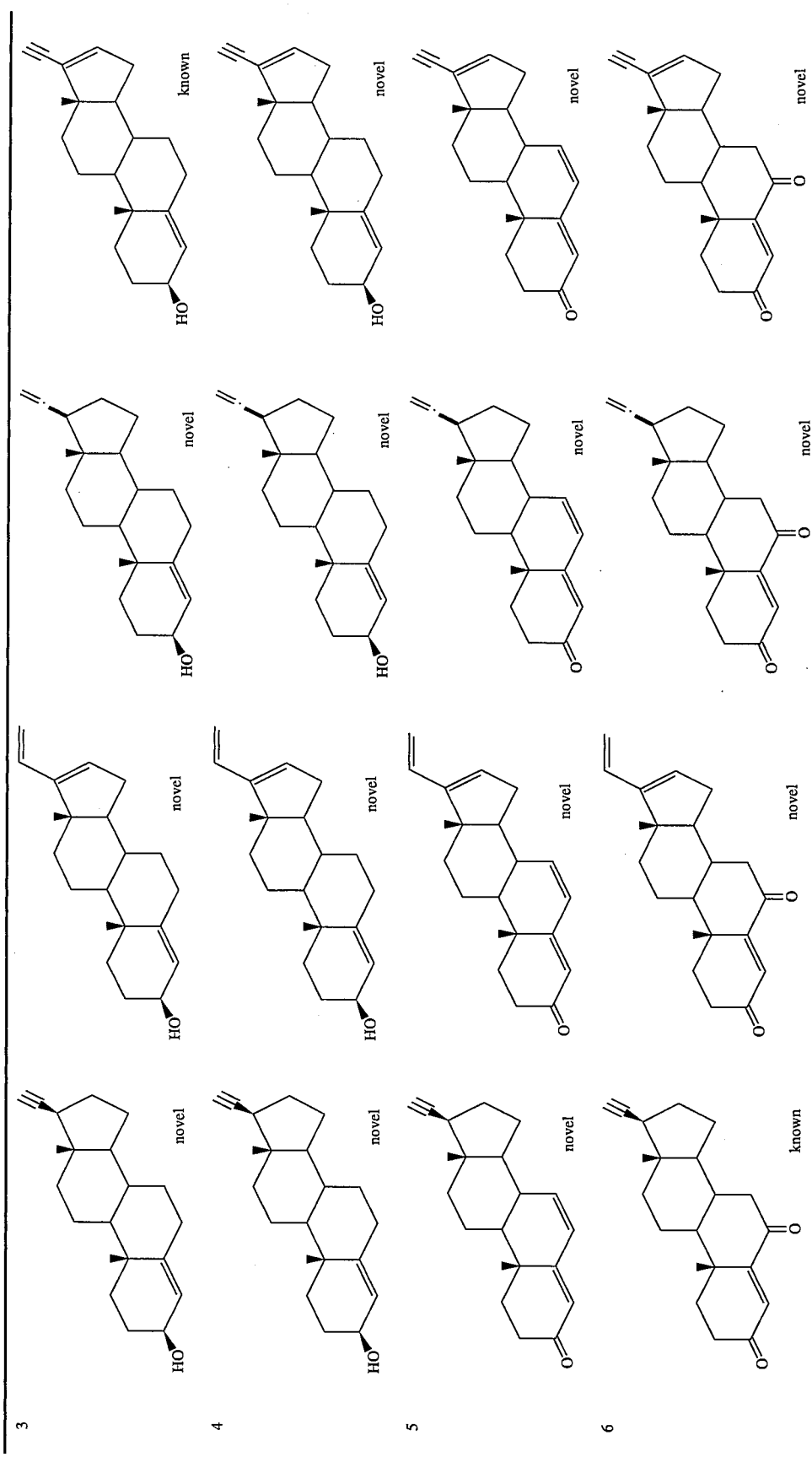

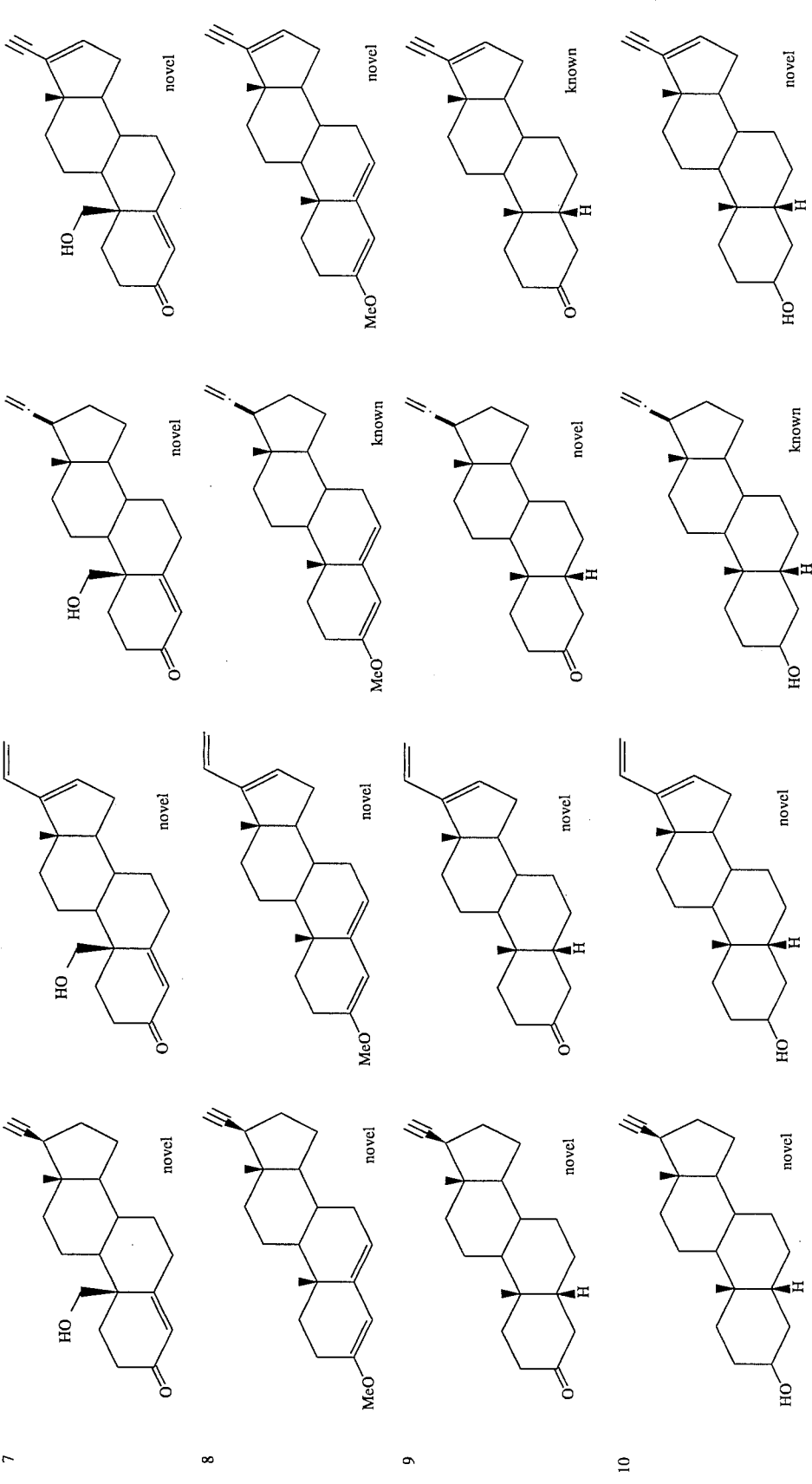

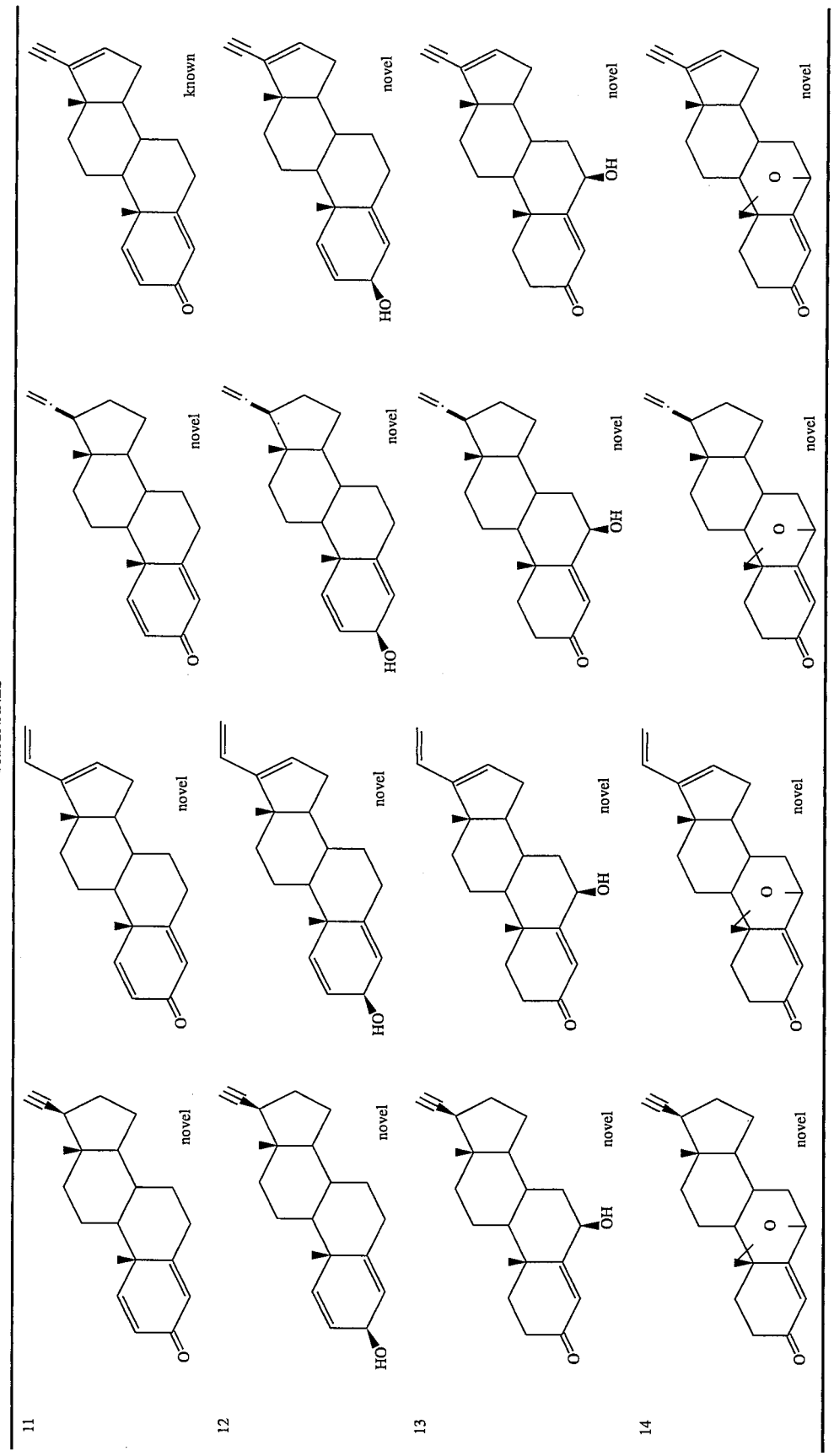

SUBSTRUCTURE SYNTHESES

Referring to the preceding table, the following are exemplary syntheses for intermediates in a given row (A1 through A13) or column (P1 through P8).

SUBSTRUCTURE SYNTHESES: TYPE A

A1:

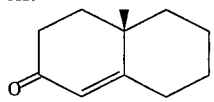

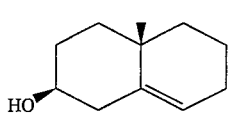
(A1)

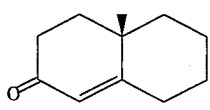
(A2)

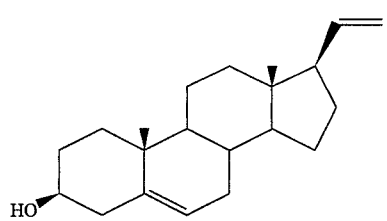

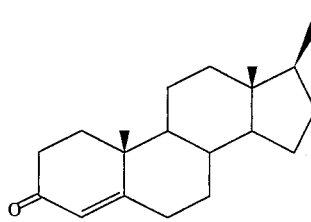

Percy L. Julian, Edwin W. Meyer and Helen C. Printy, *J. Amer. Chem. Soc.*, 1948, 70, 3, 887.

Also a commercially available substructure, for example, 17α-ethynyltestosterone.

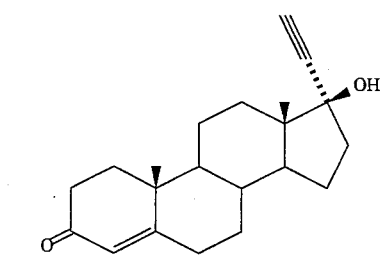

A2:

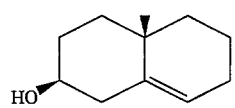

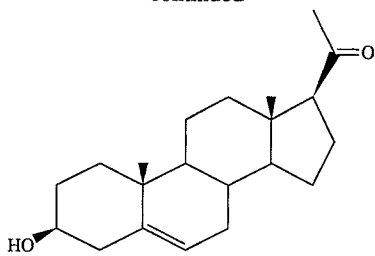

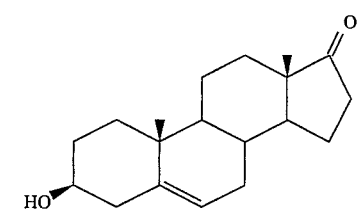

This is a commercially available substructure, for example, dehydroepiandrosterone, pregnenolone.

A3:

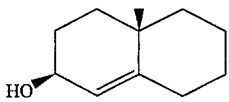

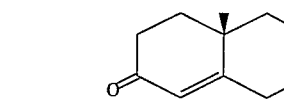
(A1)

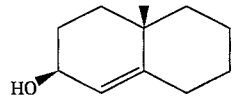
(A3)

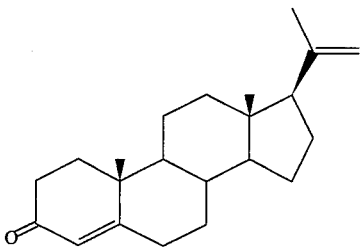

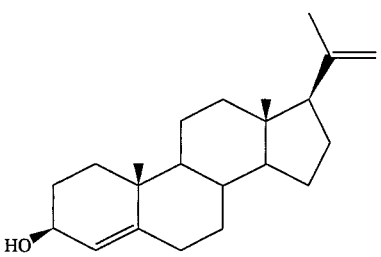

David G. Loughhead, *J. Org. Chem.*, 1985, Vol. 50, No. 20, p. 3931.

A4:

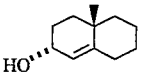

27
-continued
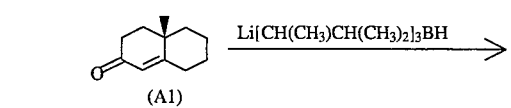
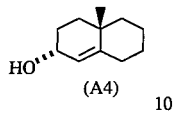
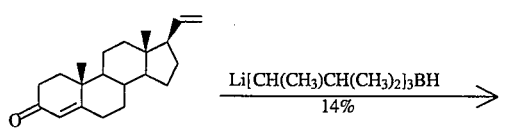
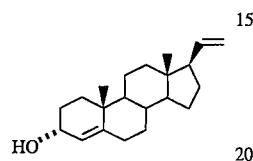
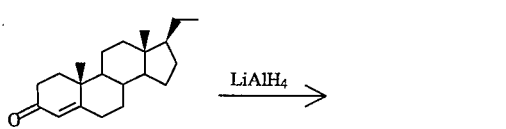
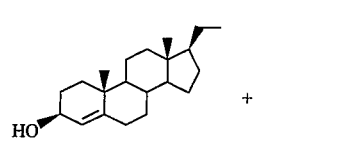
I. Z. Kabore, Q. Khuong-Huu, and A. Pancrazi, *Tetrahedron*, 1978, Vol. 34, p. 2807.
A5:
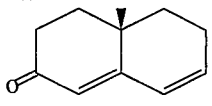
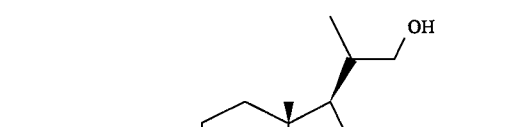
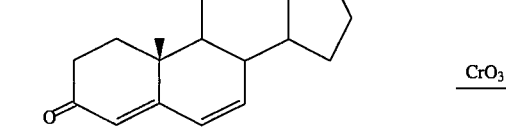
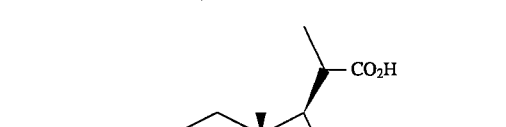
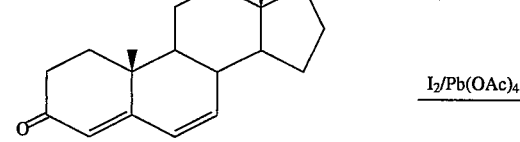
28
-continued
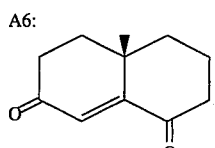
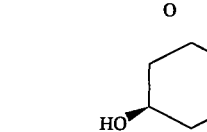
I. Dory, G. Szabo and P. Opoczky, *Acta Chim, Hung.*, Vol. 20, p. 67 (1959).
Bernhard Krieger, Egbert Blanke, and Emanuel Kaspar, German Patent 1,297,603 (1969).
A6:
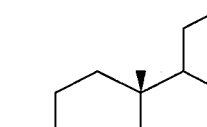

29
-continued

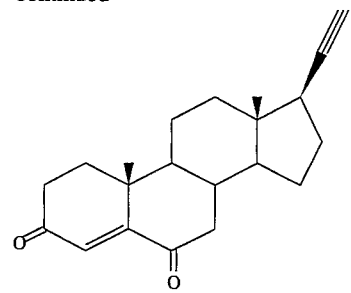

Alan M. Krubiner, Norman Gottfried, and Eugene P. Oliveto, *J. Org. Chem.*, 1969, 34, 11, 3502.

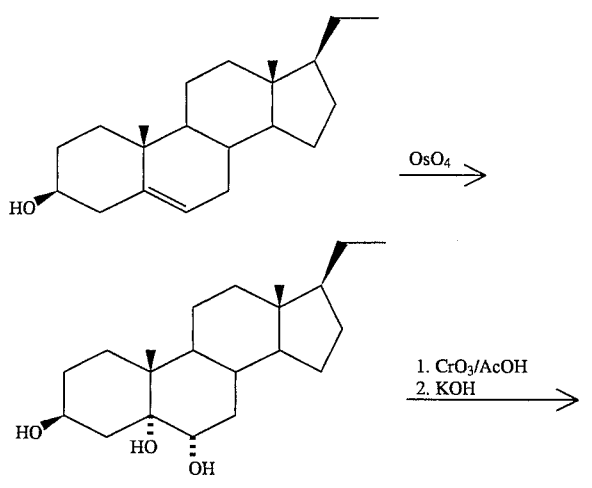

Roberto Sciaky and Alberto Consonni, *Gazz. Chim. Ital.*, 1962, 92, 730.

A7:

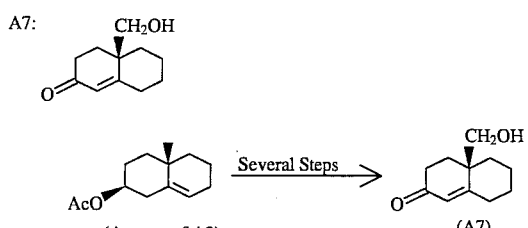

30
-continued

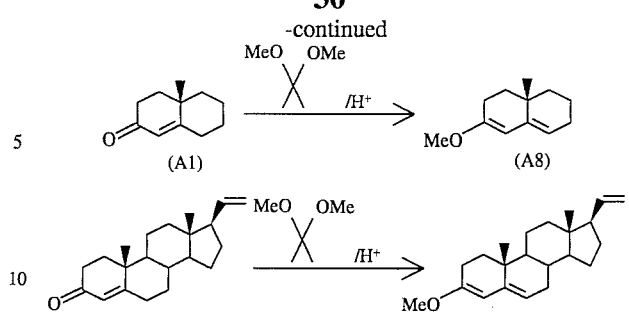

See example.

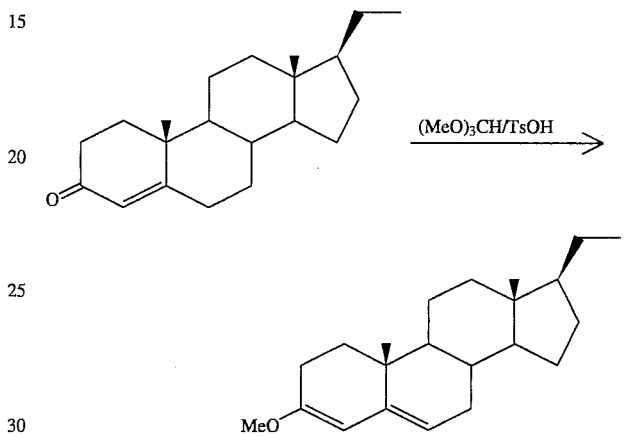

Vladimir Petrow, Yueh-sha Wang, Leon Lack, Avery Sandberg, Nobuyuki Kadohama, and Keith Kendle, *J. Steroid Biochem.*, 1983, 19 1491.

Steven R. Schow and Trevor C. McMorris, *Steroids*, 1977, Vol. 30, No. 3, p. 389.

Also a commercially available substructure, for example, 17α-ethynyldihydrotestosterone.

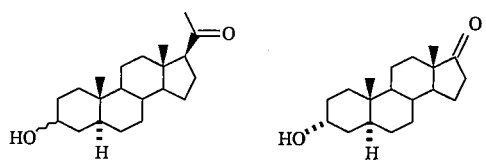
This is a commercially available substructure, for example, pregnanolone, androsterone.
Also:
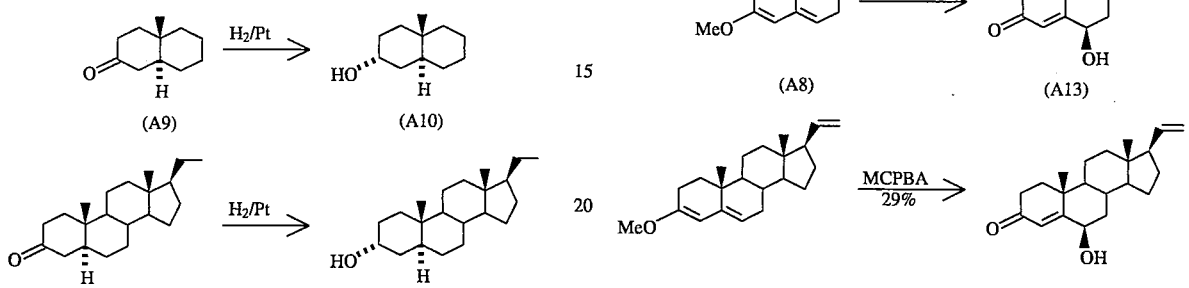
J. M. Kohli, A Zaman and A. R. Kidwai, *Phytochemistry,* 1971, Vol. 10, p. 442.
A11:
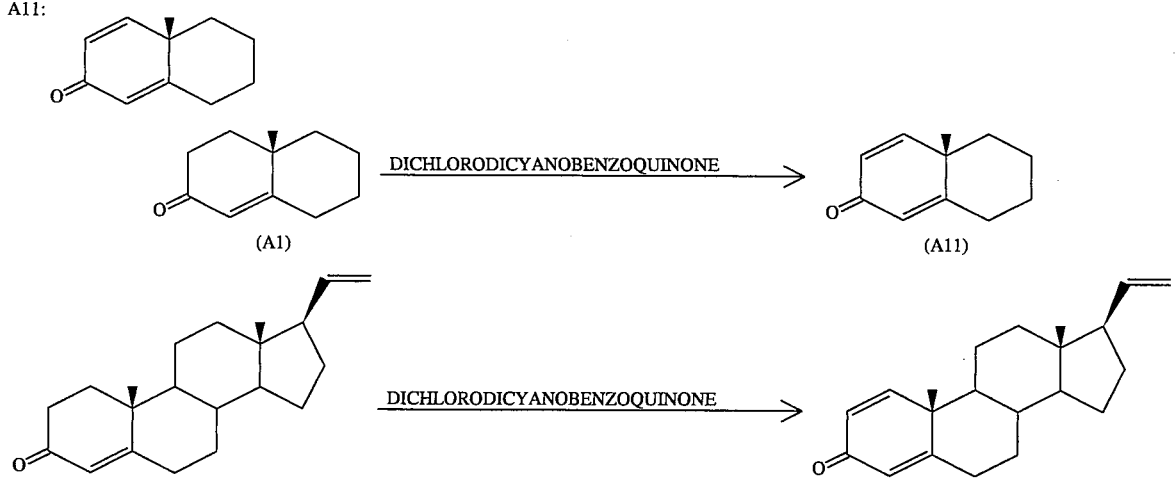
See example.
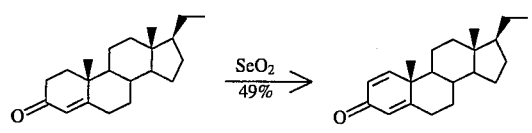
Frederick Brown and Carl Djerassi, *J. Amer. Chem. Soc.,* 1980, 102, 2, 807.
A12:
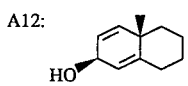
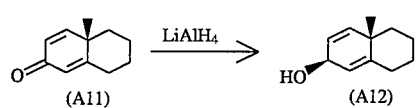
SUBSTRUCTURE SYNTHESES: TYPE P
P1:
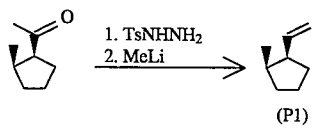
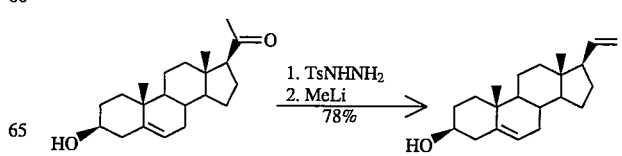

Ajay K. Bose and N. G. Steinberg, *Synthesis,* 1970, p. 595.

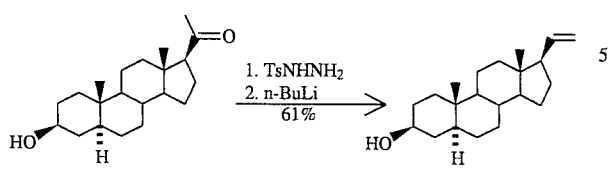

Steven R. Schow and Trevor C. McMorris, *Steroids,* 1977, vol. 30, No. 3, p. 389.

P2:

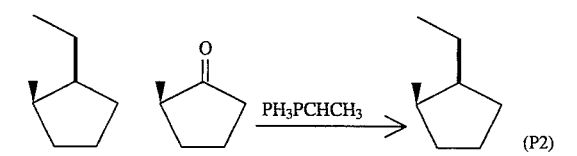

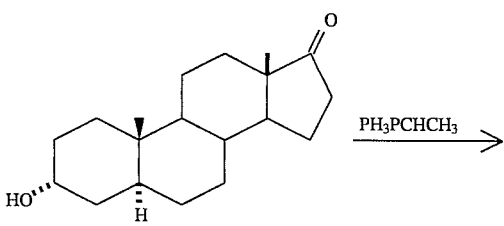

Ronald Breslow and Louis M. Maresca, *Tetrahedron Letters,* 1977, No. 7, p. 623.

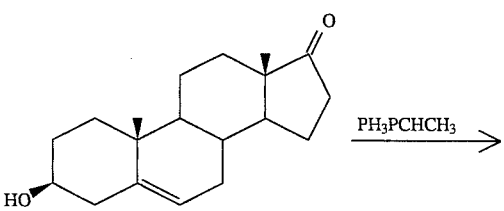

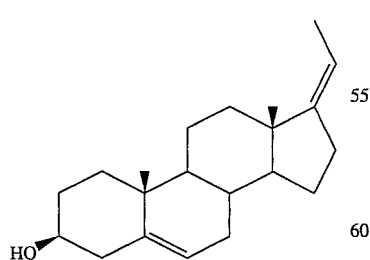

Braja G. Hazra, Vandana S. Pore, Padmakar L. Joshi, *J. Chem. Soc.,* Perkin Trans I, 1993, (15), 1819–22.

Also a commercially available substructure, for example, 5α-pregn-17(20)-en 3β-ol (Steraloids):

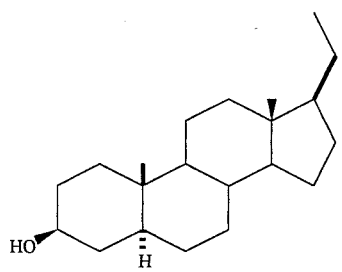

P3:

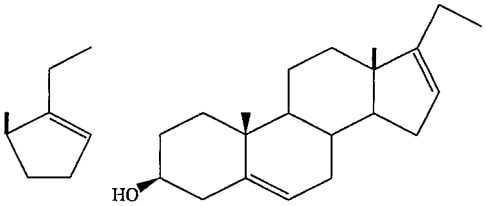

This is a commercially available substructure, for example, pregna-5,16-dien-3β-ol (Steraloids).

When commercially unavailable, synthesis proceeds as below:

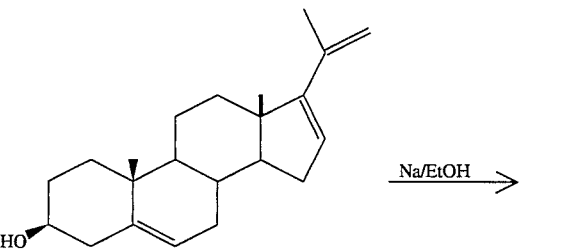

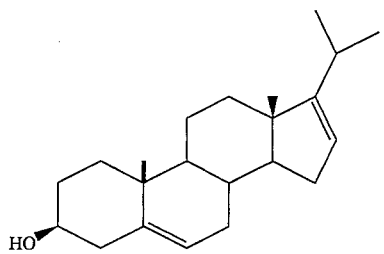

John P. Dusza and Werner Bergman, *J. Org. Chem.*, 1960, 25, 79.
P4:
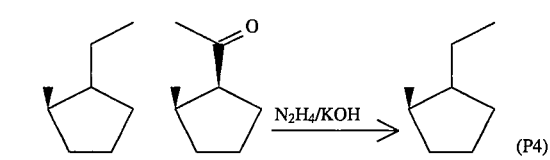
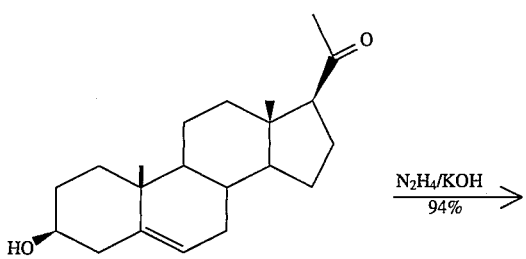
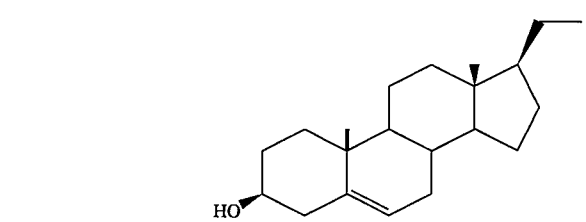
C. W. Shoppee, Ruth E. Lack, and B. C. Newman,, *J. Chem. Soc.*, 1964, p. 3388.
Also a commercially available substructure, for example, 5α-pregnan-3β-ol (Steraloids):
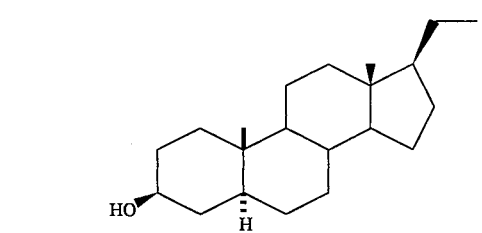
P5:
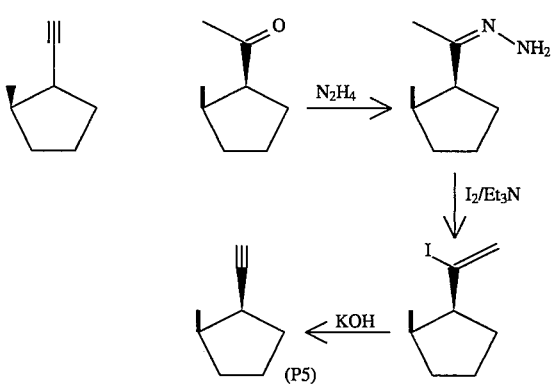
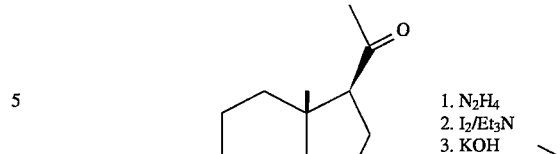
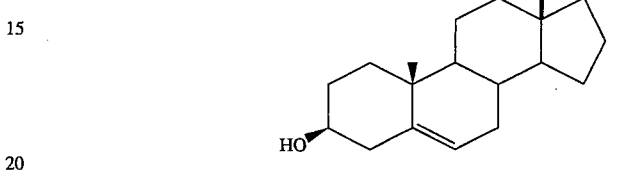
Alan M. Krubiner, Norman Gottfried, and Eugene P. Oliveto, *J. Org. Chem.*, 1969, Vol. 34, No. 11, p. 3502.
P6:
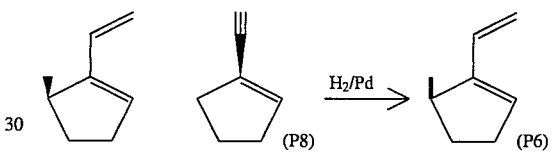
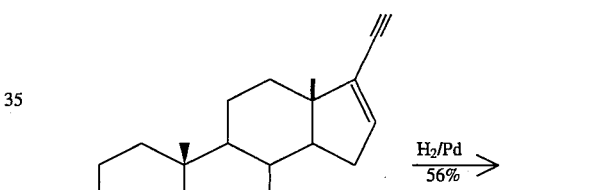
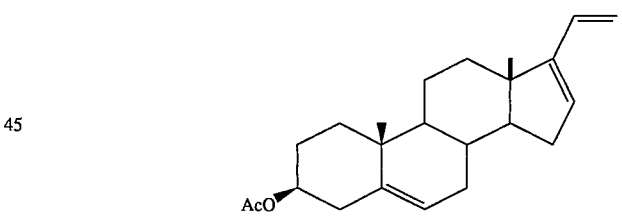
Eugene P. Oliveto, Corrine Gerold, and Lois Johnson, *J. Am. Chem. Soc.*, 1951, 73, 5073.
P7:
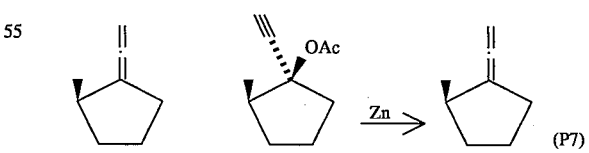

P7:
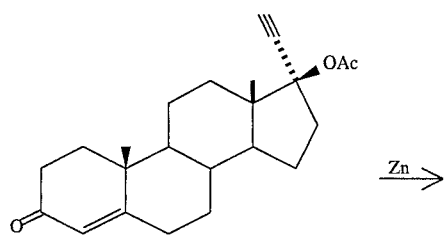
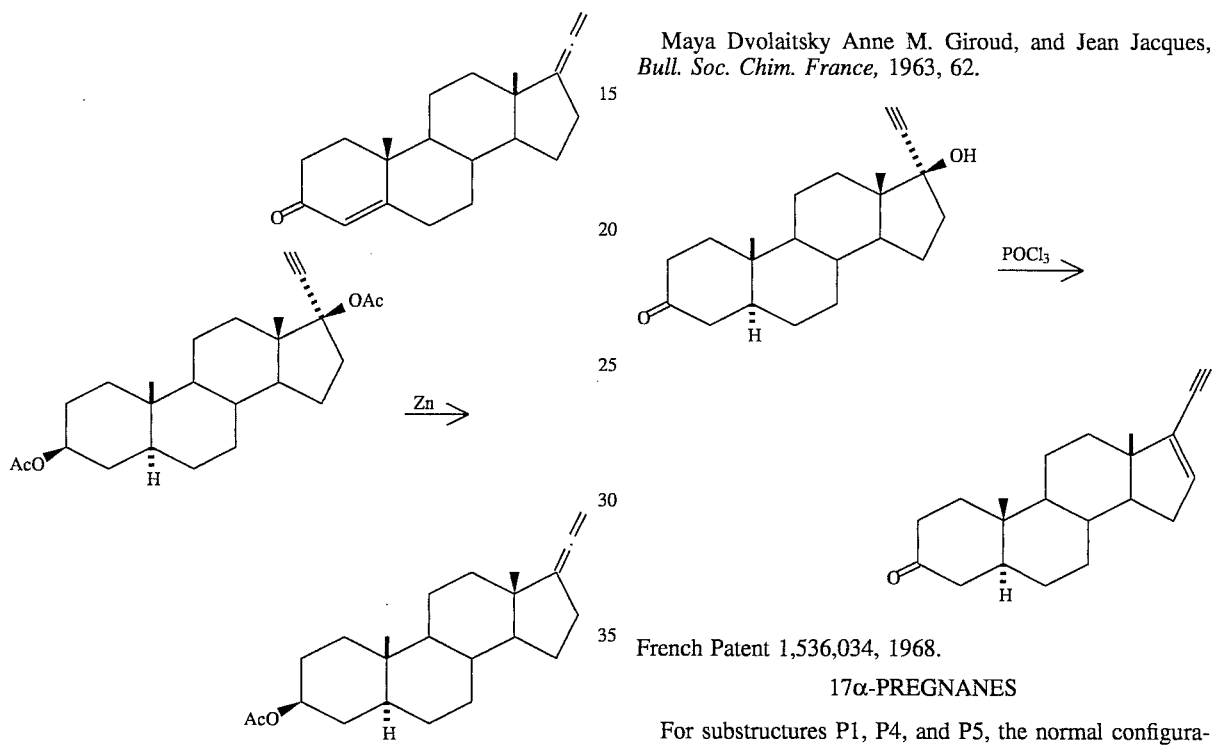
Pierre Crabble and Esperanza Velarde, U.S. Pat. No. 3,681,410, 1972.
P8:
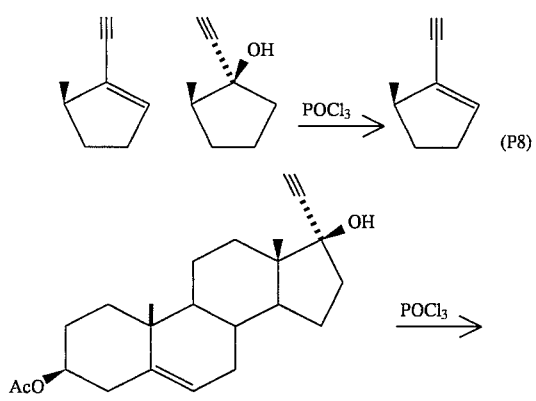
P8:
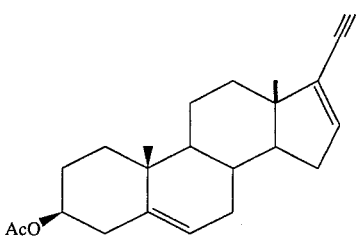
Maya Dvolaitsky Anne M. Giroud, and Jean Jacques, *Bull. Soc. Chim. France,* 1963, 62.
French Patent 1,536,034, 1968.
17α-PREGNANES
For substructures P1, P4, and P5, the normal configuration at the 17-position is β. However, the corresponding 17α analog may also be prepared by using 17α-pregnolone as the starting material. For example:
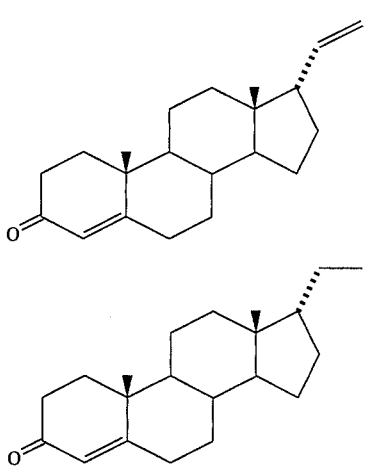

39
-continued
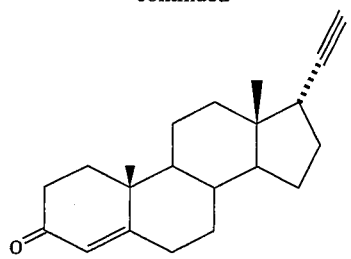
Alan M. Krubiner, Norman Gottfried, and Eugene P. Oliveto, *J. Org. Chem.*, 1969, Vol. 34, No. 11, p. 3502.
METHYLPREGNANES
The following methodology enables a methyl group to be placed at the 20-position whenever allowed by the structure, namely with P1, P2, P3, P4 and P6:
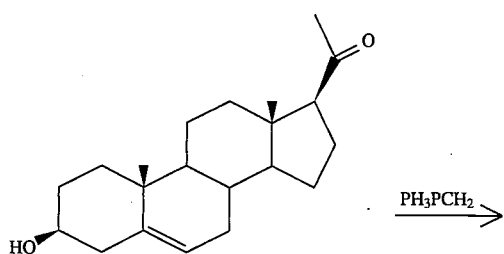
40
-continued
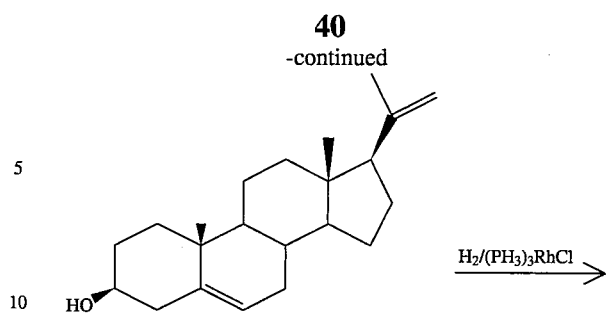
J. Bryan Jones and Keith D. Gordon, Can. *J. Chem.*, 1972, vol. 50, p. 2712.
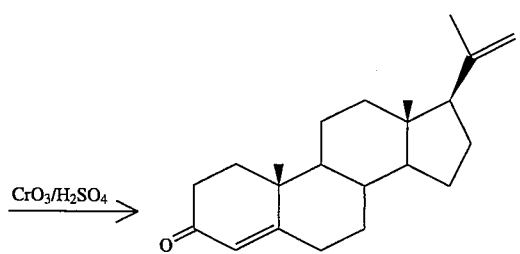
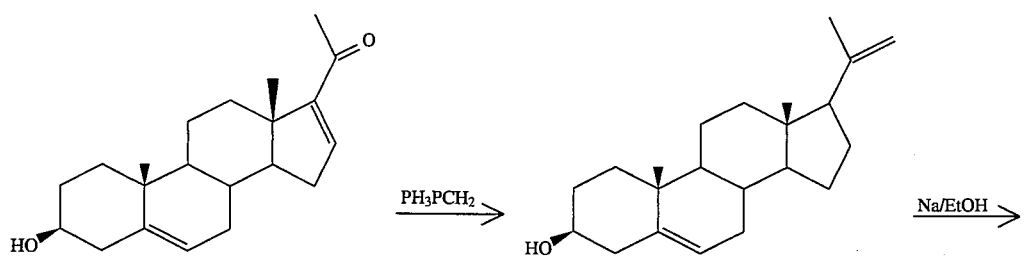
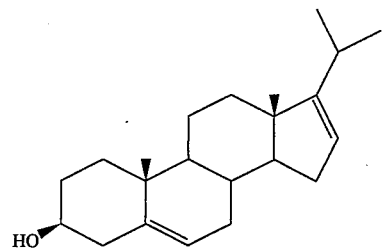

41
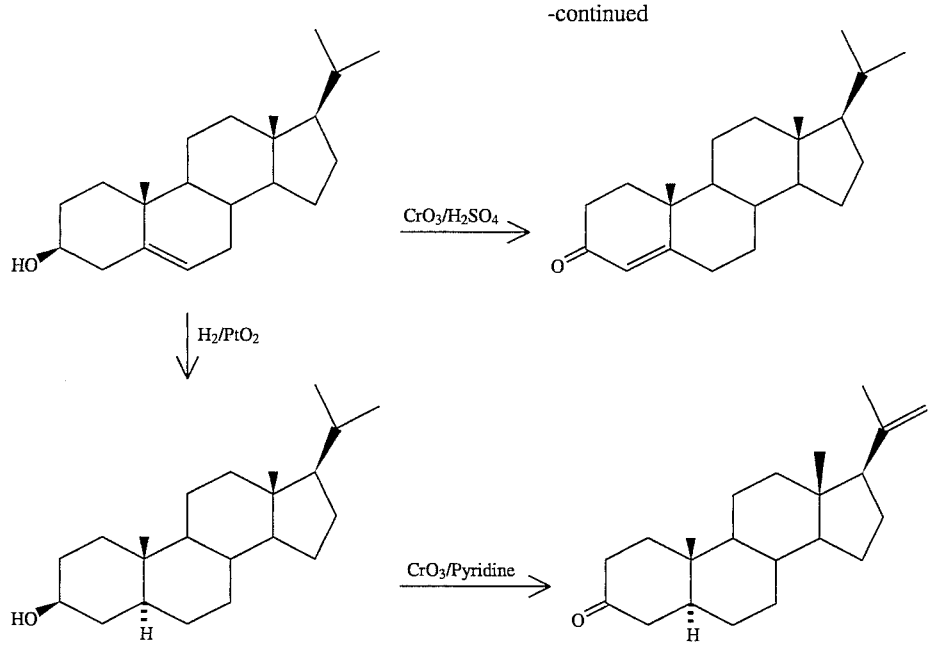
John P. Dusza and Werner Bergmann, *J. Org. Chem.*, 1960, 25, 79.
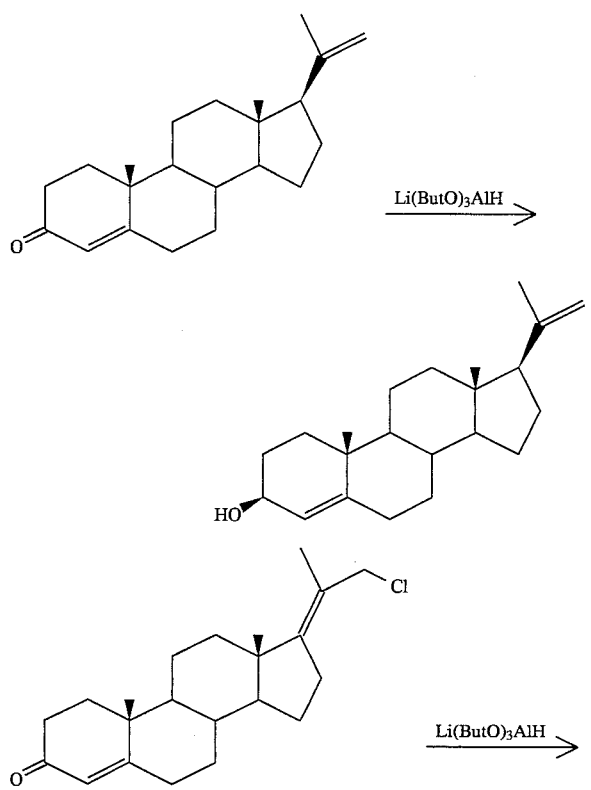
42
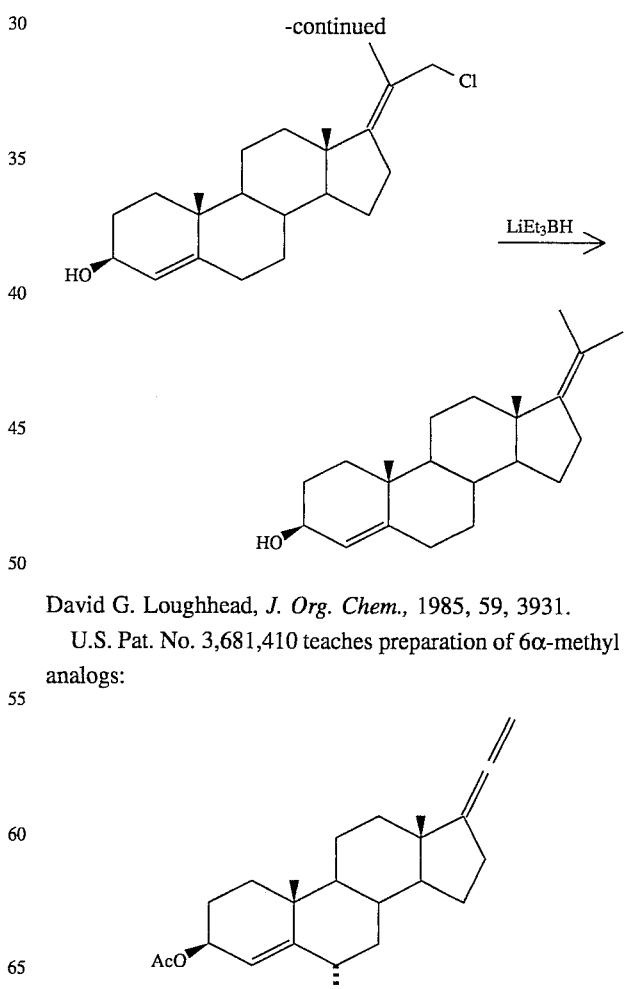
David G. Loughhead, *J. Org. Chem.*, 1985, 59, 3931.
U.S. Pat. No. 3,681,410 teaches preparation of 6α-methyl analogs:

U.S. Pat. No. 3,492,318 teaches preparation of 18- and 21-methyl analogs:

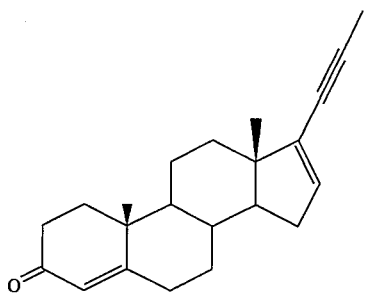

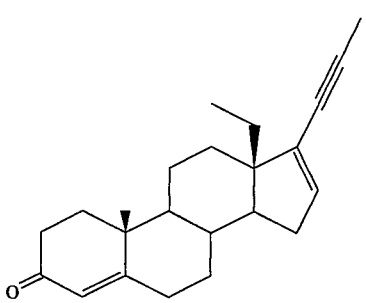

Certain methylated pregnenolone precursors are commercially available, vis 6, 16α(β)-methyl:

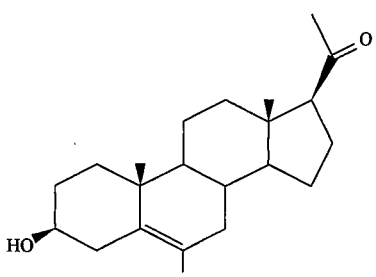

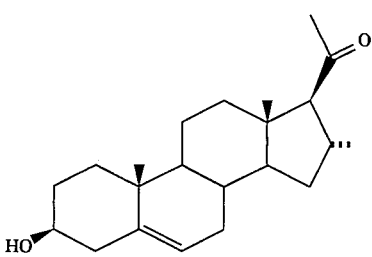

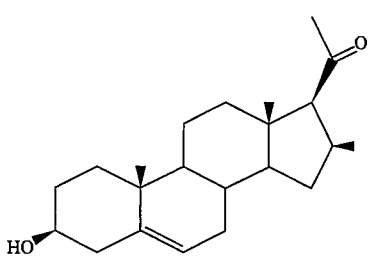

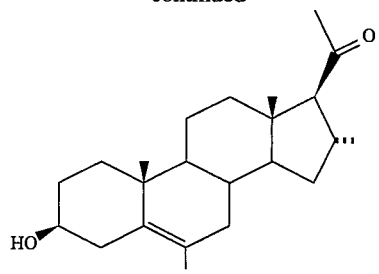

In addition 17α-methylpregnenolone is readily available: French patent 1,363,191:

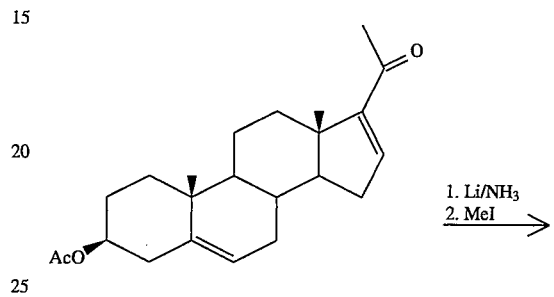

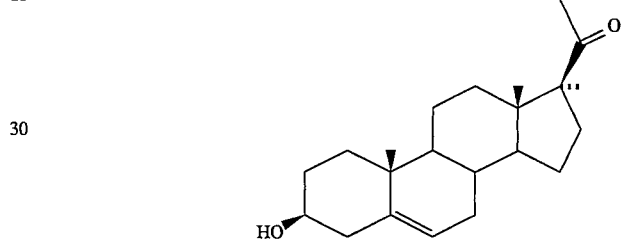

Therefore, compounds synthesized from pregnenolone may also be prepared with methyl groups at the 6, 16, or 17 positions by using the appropriate methylpregnenolone precursor.

Dimethyl compounds, such as the described 18,21-dimethylpregna- 4,16-dien-20-yn-3-one, may be prepared by one of three general methods:

The first method combines a methylated precursor, such as those in the 6, 16, or 17-positions, with methodology which introduces a methyl group, such as in the 20-position.

The second method uses a dimethylated precursor, such as the commercially available 6,16α-dimethylpregnenolone.

The syntheses of other dimethylated pregnenolone precursors have been described, as in the following examples:

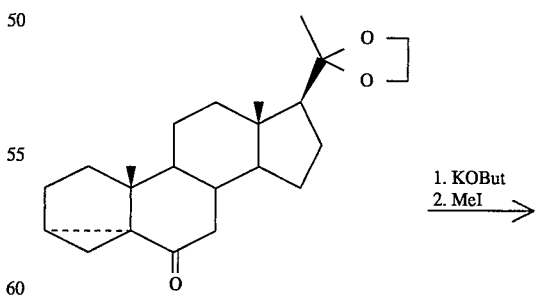

45
-continued

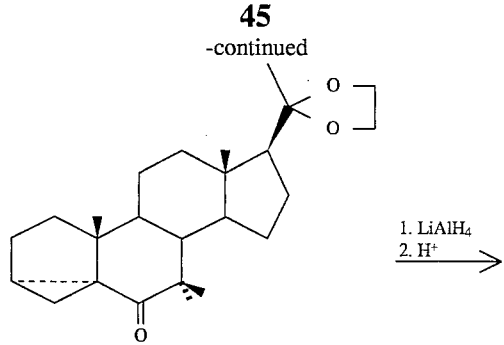

1. LiAlH₄
2. H⁺

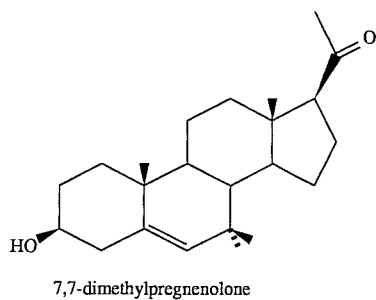

7,7-dimethylpregnenolone

Sylvestre Julia, Colette Neuville, and Pierre Simon, *Bull. Soc. Chim. France,* 1962, 1495.

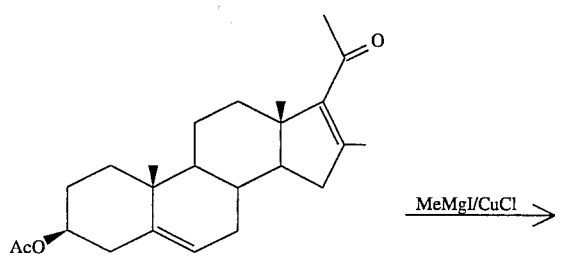

MeMgI/CuCl →

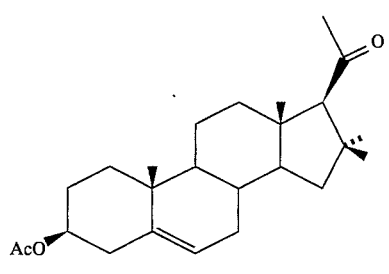

16,16-dimethylpregnenolone acetate

Elliot Shapiro, Theodore Legatt, Lois Weber, Merl Steinberg, A. Watnick, M. Eisler, Marilyn Gilmore Hennessey, C. T. Coniglio, W. Charney, and Eugene P. Oliveto, *J. Med. Pharm. Chem.* 1996, 5, 975.

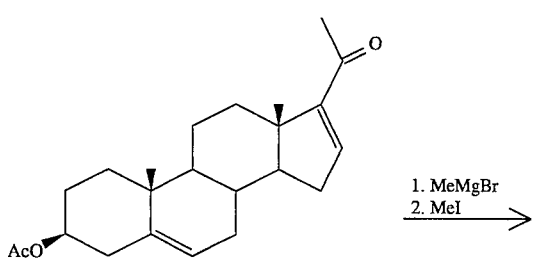

1. MeMgBr
2. MeI →

46
-continued

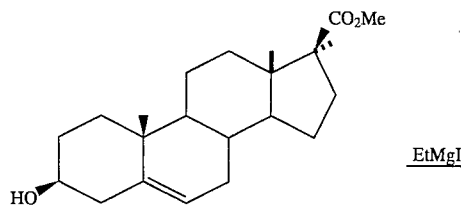

16α, 17α-dimethylpregnenolone

James Cairns, Colin L. Hewett, Robert T. Logan, George McGarry, Donald F. M. Stevenson, and Gilbert F. Woods, *J. C. S. Perkin I,* 1976, 1558.

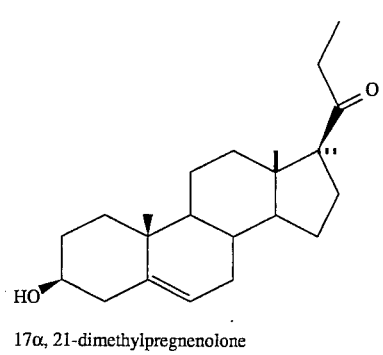

EtMgI →

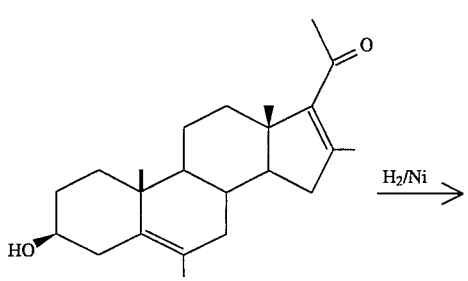

17α, 21-dimethylpregnenolone

R. Deghenghi and R. Gaudry, *J. Amer. Chem. Soc.,* 1961, 4668.

British Patent 927,515:

H₂/Ni →

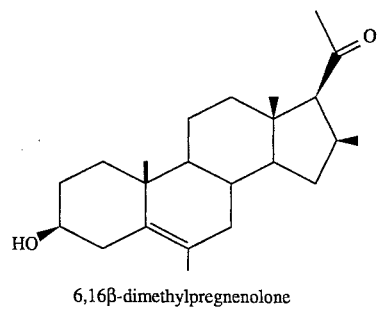

6,16β-dimethylpregnenolone

47
-continued

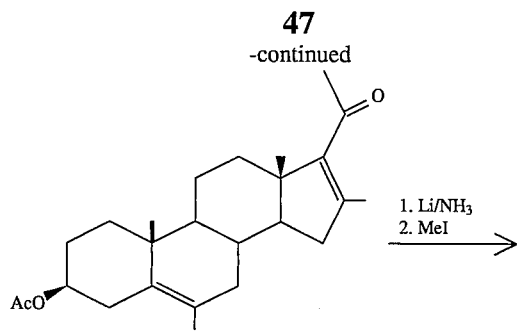

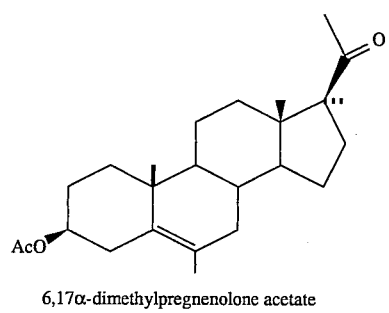

6,17α-dimethylpregnenolone acetate

Romano Deghenghi and Roger Gaudry, *Tetrahedron Letters*, 1962, No. 11, p. 489.

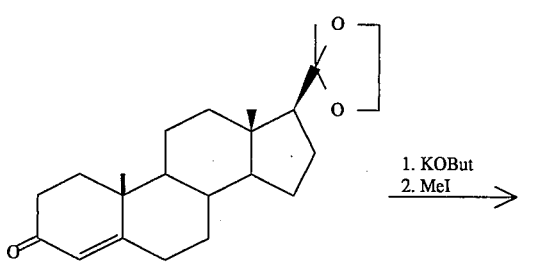

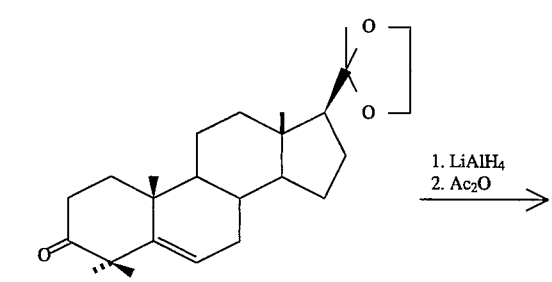

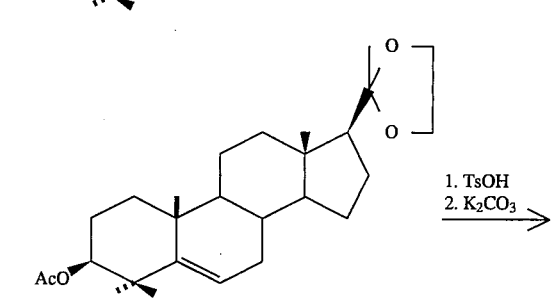

48
-continued

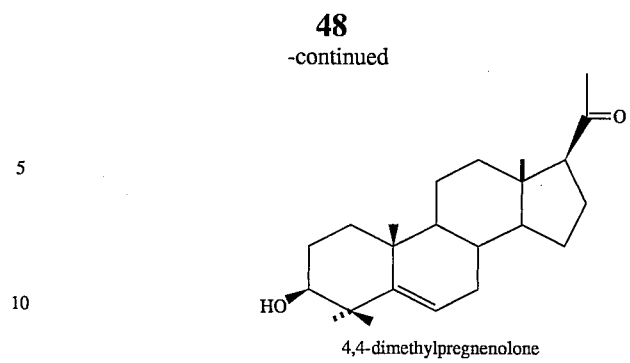

4,4-dimethylpregnenolone

W. J. Adams, D. K. Patel, V. Petrow, I. A. Stuart-Webb, and B. Sturgeon, *J. Chem. Soc.*, 1956, 4490.

The third method starts with an unmethylated precursor, such as pregnenolone, and utilizes methodology which introduces two methyl groups, as in the following example:

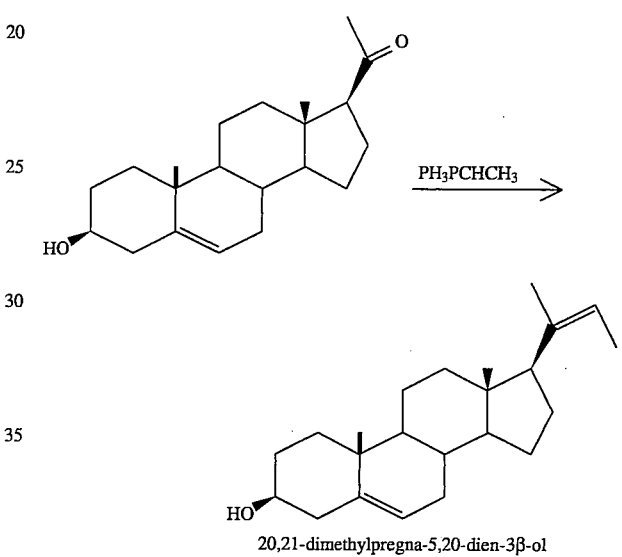

20,21-dimethylpregna-5,20-dien-3β-ol

The 20,21-dimethyl pregnanes are also known as 24-nor-cholanes. 24-norcholanes may alternatively be prepared by degradation of a cholane precursor, as in the following example:

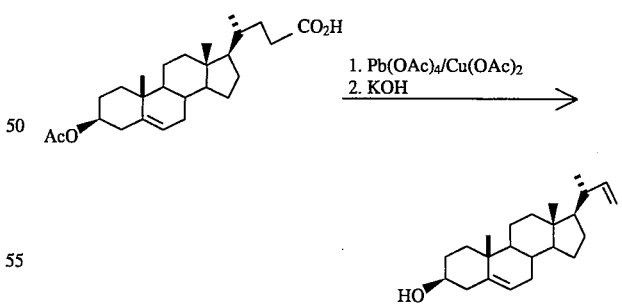

Yutaka Hirano, Tadashi Eguchi, Masaji Ishigmo, and Nobuo Ikekawa, *Chem, Pharm. Bull.*, 1983, 31(2), 394.

HALOPREGNANES

U.S. Pat. No. 3,681,410 teaches the preparation of:

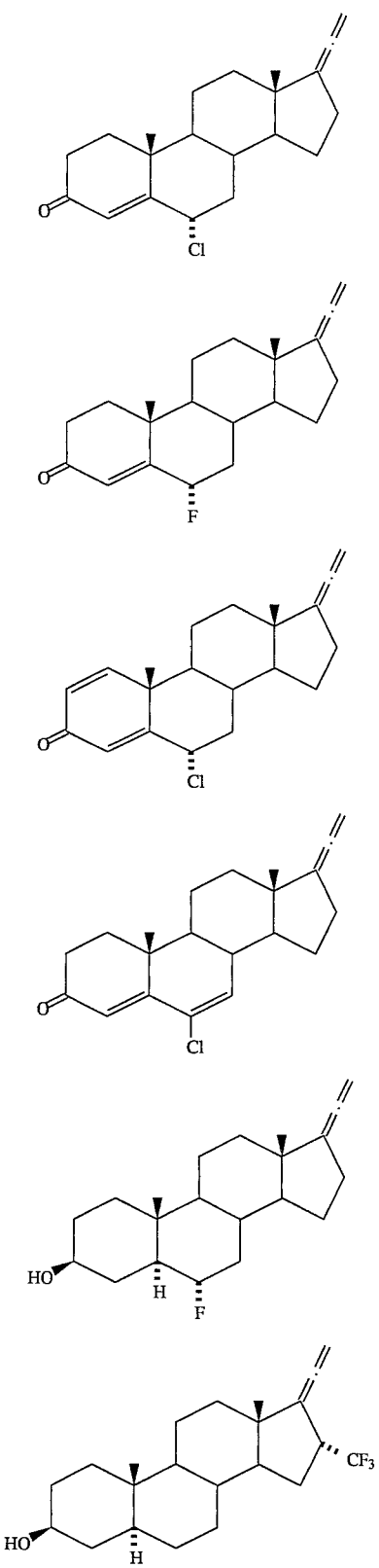

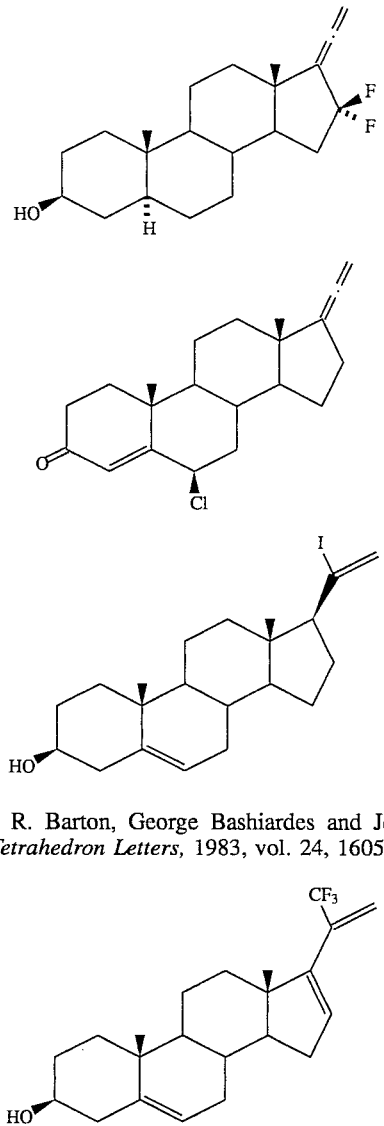

Derek H. R. Barton, George Bashiardes and Jean-Louis Fourrey *Tetrahedron Letters*, 1983, vol. 24, 1605.

Biao Jiang and Yuanyao Xu, *Tetrahedron Letters*, 1992, vol. 33, 511.

C. Synthetic Methods

1. Preparation of 3-, 6-, 19-, 20- and 21-position derivatives.

Figure 1B:
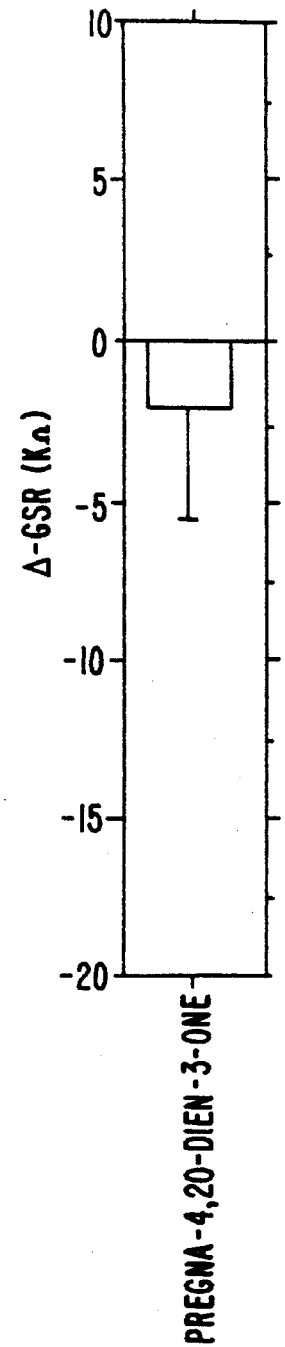
Figure 1C:
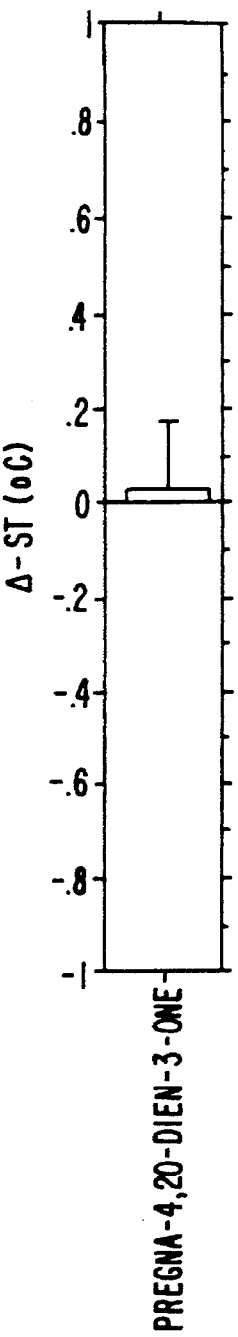

The compounds used in the methods of this invention are pregnane steroids substituted at the 3-, 6-, 19-, 20- and 21-positions. Many of the 3-substituted steroids are known compounds which may be derived from 3-oxo-steroids. As shown in FIG. 1, pregna-4,20-diene-3-one (1) can be converted to a 3,5,20 -triene ether (2) or 1,4,20-trien-3-one (3), which are respective starting materials for 6- and 3-substituted hydroxy derivatives.

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aprotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the work-up procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

2. Preparation of 19-OH derivatives

Synthesis of 19-OH-pregna-4,17-diene-3-one.

A method of synthesizing this compound is provided in SCHEME 3.

D. Pharmaceutical COmpositions and Methods of Use

An embodiment of the subject invention is a method of altering the hypothalamic function of an individual. Another embodiment is altering an autonomic function of an individual. These autonomic functions include but are not limited to heart rate, respiratory rate, brain wave patterns (percentage alpha cortical activity), body temperature. Other embodiments include, but are not limited to, methods of diminishing negative affect, negative mood or negative character traits of an individual. Another embodiment is a method of treating female premenstrual stress. All of these embodiments are accomplished by means of the non-systemic, nasal administration of certain pregnane steroids, combinations of pregnane steroids and combinations of one or more pregnane steroids and one or more androstane and/or estrene steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., non-invasively. Drug action is mediated through binding of the ligands, described herein, to specific receptors displayed by neuroepithelial cells in the nose, preferably in the VNO. This Furthermore, the mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary (See Johnson, et al., supra).

The ligand substances described herein, or their sulfated, cypionated, benzoated, propionated, or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol. Alternatively, the active compound can be prepared as a creme or an ointment composition and applied topically within the nasal cavity. In addition, a vomeropherin may be administered as vapor contained in an air puff delivered to the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active pregnane compound(s) of Formula I, and the composition may or may not additionally include one or more androstane or estrene steroids. In addition, the compositions may include other medicinal agents, pharmaceutical agents, carriers, adjuvants, etc.

The most likely means of communication of a semiochemical ligand is the inhalation of a naturally occurring pheromone present on the skin of another. Since these compounds are relatively nonvolatile, it is estimated that, even during intimate contact, a human subject would inhale picogram amounts of a naturally occurring steroid from the skin of another. From the amount inhaled it is estimated that only about 1% would reach the receptors of the vomeronasal organ.

The amount of vomeropherin administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response. When administered to the nasal cavity, the dosage is about 100 picograms to about 100 micrograms, preferably about 1 nanogram to about 10 micrograms, more preferably about 10 nanograms to 1 about microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc.

an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives Of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monoleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

F. Measuring Affect, Mood and Character Trait.

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of related adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp 1417 In: Medical Physiology. Vol. IIEd.: V. B. Mountcastle (1980); Wolfram Bouscein. Electrodermal Activity (Plenum Press 1992). In addition, non-verbal cues such as facial expression and body posture may be evaluated.

III. Examples

The following examples are intended to illustrate but not to limit the invention.

Abbreviations used in the examples are as follows: aq.= aqueous; RT.=room temperature; PE=petroleum ether (b.p. 50°–70°); DMF=N,N-dimethylformamide; DMSO=dimethyl sulfoxide; THF=tetrahydrofuran.

SCHEME 1

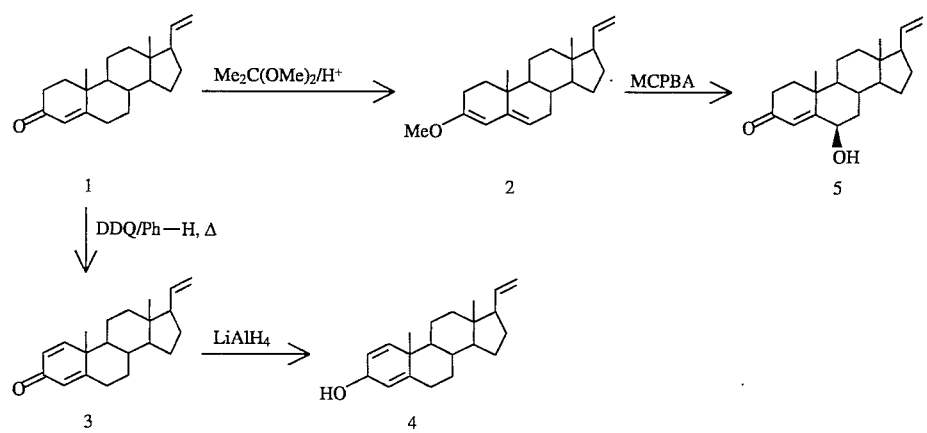

SCHEME 2
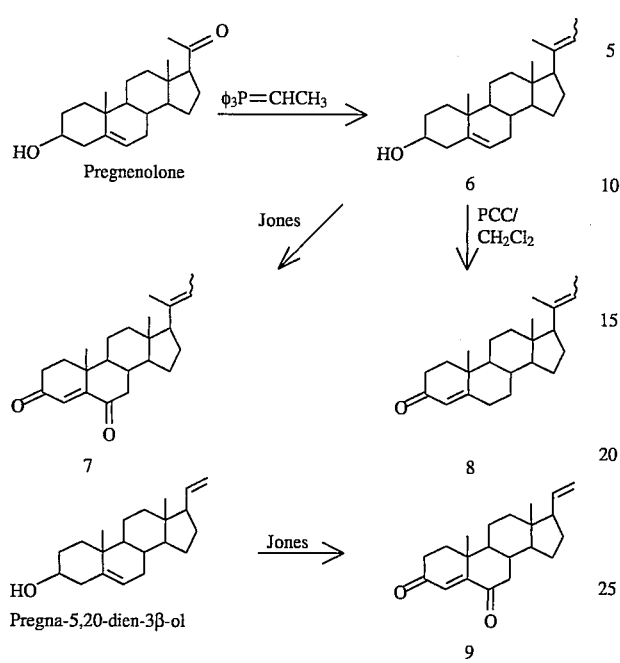
SCHEME 3
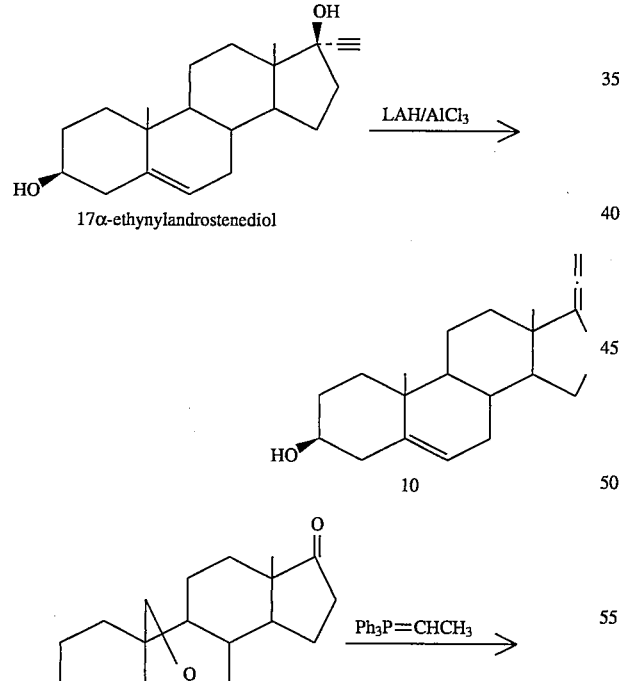
-continued
SCHEME 3
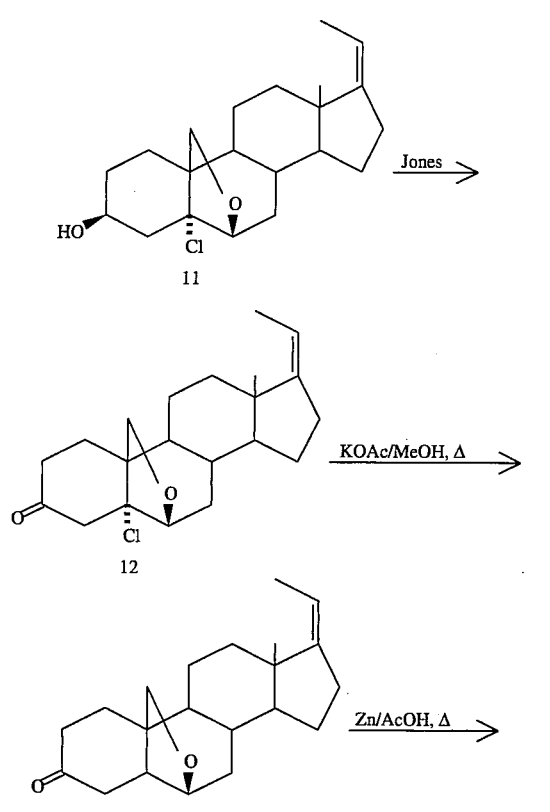
SCHEME 4
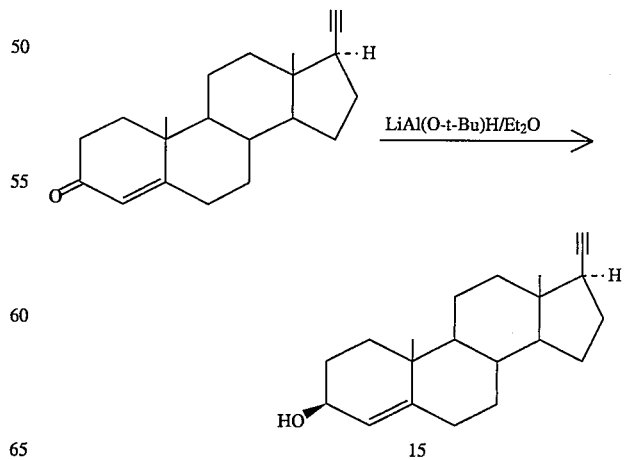

Example 1

Pregna-4,20-dien3α(β)-ol

To a 1M solution of lithium trisiamylborohydride (5.0 ml, 5.0 mmole) at −78° C. under argon was added a solution of pregna-4,20-dien-3-one (1.10 g, 3.70 mmole) in dry THF (14 ml), with stirring, and the mixture was allowed to warm to room temperature. After 3 hours, the mixture was cooled to −78° C. and the following reagents were added sequentially: water (2 ml), ethanol (6 ml), 12% aqueous KOH solution (10 ml), and 3% hydrogen peroxide (50 ml). The mixture was allowed to warm to room temperature with stirring. After 2 hours, ethyl acetate (200 ml) was added and the stirring was continued. The organic layer was separated, and was washed with satd. $NaHSO_3$ solution, satd. $NaHCO_3$ solution, and satd. NaCl solution, dried ($Na_2SO_4$), and evaporated in vacuo to give 2.1 g crude material. This was purified by flash chromatography on 210 g silica gel (230–400 mesh), eluting with $EtOAc/CH_2Cl_2$ (5:95→7:93) to give three fractions. Fraction 1 (0.8 g) contained the impure 3α-alcohol. Fraction 2 (0.1 g) was a mixture of the 3β- and 3β-alcohols. Fraction 3 (0.25 g) was the pure 3β-alcohol (23%). Fraction 1 was repurified by flash chromatography on 80 g silica gel (230–400 mesh), eluting with EtOAc/hexane (10:90→15:85) to give 0.15 g pure 3α-alcohol (14%).

Example 2

Pregna-3,5 20-trien-3-yl methyl ether, 2

Referring to SCHEME 1, compounds 2, 3, 4 and 5 were prepared as follows.

A solution of pregna-4,20-dien-3-one (1, 1.00 g 3.35 mmol) in 2,2-dimethoxypropane (5.0 Ml, 41 mmol) dimethylformamide (5.0 mL) and methanol (0.2 mL) was refluxed with catalytic p-toluenesulfonic acid monohydrate (26.9 mg, 0.141 mmol) for 2 h. After cooling, sodium bicarbonate (153.6 mg, 1.828 mmol) was added and the reaction mixture was partitioned between 75 mL of hexanes and 50 mL of ice water. The organic phase was washed twice with 50 mL portions of water and once with 50 mL of brine, after which it was filtered through a 17 mm high×30 mm dia. column of silica gel 60. Product was further eluted with 100 mL of hexanes. Concentration of the combined eluates and recrystallization from acetone/methanol gave lustrous very slightly yellow platelets (828.7 mg, 2.652 mmol, 79%) m.p. 111°–114° C. (NA-1193B-104)

Example 3

Pregna-1,4,20-trien-3-one, 3

Pregna-4,20-dien-3-one (1, 1.19 g. 3.99 mmol) was refluxed for 24 h with 2,3-dichloro-5,6-dicyano- 1,4-benzoquinone (DDQ, 2.72 g, 12.1 mmol) in 40 mL of benzene under Argon. The cooled suspension was diluted with ether and washed with two 100 mL portions of 5% (w/w) sodium hydroxide, two 100 mL portions of water and once with 100 mL of brine. Ether (100 mL) was added to the resulting emulsion, which was dried over sodium sulfate and then filtered through a column of sodium sulfate (20 g). After washing the residue twice with 50 mL portions of ether the combined filtrates were concentrated under reduced pressure and then flash chromatographed (25% ethyl acetate/hexanes on silica gel) to give a slightly yellow crystalline solid (0.26 g, 0.88 mmol, 22%). (NA-119B-64)

Example 4

Pregna-1,4,20-trien-3-ol, 4

Pregna-1,4,20-trien-3-one (3, 0.26 g, 088 mmol) in 25 mL of anh. ether was reduced under argon atmosphere with lithium aluminum hydride (250.5 mg, 6.601 mmol) for 2 h and then quenched with 2.50 g of Glauber's salt. The resulting suspension was stirred 70 min., filtered, and washed twice with 50 mL portions of ether. After concentrating the combined filtrates under reduced pressure the residue was purified using preparative TLC (35% ethyl acetate/hexanes on alumina to give white needles (26.1 mg, 87.4 μmol, 10%) m.p. 98°–128° C. (NA-1993B-81)

Example 5

Pregna-4,20-dien-6β-ol-3-one, 5 m-Chloroperbenzoic acid (MCPBA, 77.4%, 763.4 mg, 3.42 mmol) suspended in 30 mL of 1,2-dimethoxyethane (DME), 6 mL of water and 2.4 mL of 5% (w/w) sodium hydroxide was added to a solution of pregna-3,5,20-trien-3-yl methyl ether (2, 400.3 mg, 1.281 mmol) in 20 mL of DME+2 mL of water over 85 min. with stirring. The reaction was continued 5 h and was then poured into 50 mL of saturated sodium bicarbonate. The mixture was extracted three times with 50 mL of ether and the combined organic extracts were washed with 50 g of 5% (w/w) sodium thiosulfate pentahydrate+three 50 mL portions of brine, dried over magnesium sulfate, and filtered through Celite. After washing the residue with 10 mL of ether the combined filtrates were concentrated in vacuum. Flash chromatography (35% ethyl acetate/hexanes on silica gel) and preparative TLC (35% ethyl acetate/hexanes on silica gel) gave a difficultly separable mixture as white crystals (95.5 mg, 0.304 mmol, 24%). (NA-1993B-106)

Example 6

20,21-Dimethylpregna-5,20-dien-3β-ol, 6

Referring to SCHEME 2, compounds 6, 7, 8 and were prepared as follows.

Ethyltriphenylphosphonium bromide (25.99 g, 70.00 mmol) and potassium t-butoxide (7.86 g, 70.0 mmol) with 80 mL of anh. DMSO were stirred under Argon in oil bath at ca. 80° C. for 1 h, after which pregn-5-en-3β-ol-20-one (4.43 g, 14.0 mmol) in 80 mL of warm anh. DMSO was added. The red suspension was stirred 1 h, removed from the heat and poured into 200 mL of ice-brine. The mixture was then extracted three times with 100 mL of ether and the combined organic extracts were washed with 100 mL of brine, dried over sodium sulfate, and filtered through Celite. After washing the residue with 50 mL of ether the combined filtrates were concentrated under reduced pressure. The yellow residue was taken up in 95% ethanol with heating, boiled briefly with 1 g of charcoal, and filtered through Celite. After cooling and filtration the residue was recrystallized twice more from ethanol to give white crystals (1.746 g, 5.314 mmol, 38%), m.p. 140°–145° C. (NA-1993B-68)

Example 7

20,21-Dimethylpregna-4,20-dien-3,6-dione, 7

Jones reagent (2.67M, 2.0 mL. 5.3 mmol) was added to a solution of 20,21-dimethylpregna- 5,20-dien-3β-ol (6, 460.1 mg, 1.400 mmol) in 50 mL of acetone and the reaction was stirred 45 min. After quenching with 2-propanol (1.0 mL) the mixture was poured into 100 mL of water and extracted three times with 50 mL of ethyl acetate. The combined organic extracts were washed with 50 mL of saturated sodium bicarbonate+50 mL of brine, dried over magnesium sulfate, and filtered through Celite. The residue was washed with 25 mL of ethyl acetate and the combined filtrates were concentrated under reduced pressure. Flash chromatography (25% ethyl acetate/hexanes on silica gel) and recrystallization of the residue from 95% ethanol gave yellow needles (138.2 mg, 0.4059 mmol, 29%), m.p. 172°–178° C. (NA-1993B-73)

Example 8

20,21-Dimethylpregna-4,20-dien-3-one, 8

20,21-Dimethylpregna-5,20-dien-3β-ol (6,400.3 mg, 1.218 mmol) in 5 mL of methylene chloride was oxidized with pyridinium chlorochromate (525.4 mg 2.437 mmol) for 42 h. Ether (3.5 mL) was added and the suspension was filtered through a 5 mm dia.×60 mm high column of silica gel. The column was further eluted with 3.5 mL of ether and the combined filtrates were concentrated under reduced pressure. Flash chromatography of the resin followed by recrystallization from aqueous ethanol gave yellow crystals (43.6 mg, 0.134 mmol 11%). m.p. 157°–165° C. (NA-1993B-84)

Example 9

Pregna-4,20-dien-3,6-dione 9

A solution of pregna-5,20-dien-3β-ol (300.5 mg, 1.000 mmol) in 35 mL of acetone was cooled in an ice water bath and 2.67M Jones reagent (0.71 mL, 1.9 mmol) was added. After stirring 1½ h a further 0.71 mL of Jones reagent were added and the reaction was continued 45 min, 2-Propanol (1.0 mL) was added and the mixture was poured into 100 mL of water. The mixture was then extracted twice with 50 mL of ethyl acetate and the combined organic extracts were washed with 50 mL of saturated sodium bicarbonate+50 mL of water+50 mL of brine and filtered through a 21 mm dia×22 mm high column of silica gel 60. The column was eluted further with 25 mL of ethyl acetate and the combined filtrates were concentrated under reduced pressure. Recrystallization of the residue from 95% ethanol gave a light yellow powder (104.6 mg, 0.3348 mmol 33%), m.p. 114°–120° C. (NA-1993A47)

Example 10

Pregna-5,17,20-trien-3β-ol, 10

A solution of 17α-ethynylandrostenediol (439.4mg, 1.397 mmol) in 10 mL of dry THF was added to a suspension of lithium aluminum hydride (106.5 mg, 2 mmol) and aluminum chloride (122.9 mg, 0.9220 mmol) in 10 mL of dry THF under argon. After refluxing 17 h the reaction mixture was quenched by stirring 2 h with sodium sulfate decahydrate (1.00 g, 3.10 mmol). The reaction was-filtered and the residue washed with three 10 mL portions of THF. Concentration of the combined filtrates under reduced pressure gave 0.44 g of white solid,which was purified by flash chromatography (30% ethyl acetate/hexanes on silica gel) and twofold recrystallization from aqueous ethanol, giving lustrous white crystals (92.0 mg, 0.303 mmol, 22%), m.p. 144°–149° C. (NA-1994A-195)

Example 11

5α-Chloro-6β,19-epoxypregn-17-en-3β-ol, 11

Referring to SCHEME 3, compounds 11, 12, 13, and 14 were made as follows.

Ethyltriphenylphosphonium bromide (3.05 g, 8.22 mmol) and potassium t-butoxide (0.92 g, 8.2 mmol) were reacted under argon in anh. DMSO (9.2 mL) for 1 h in a 76°–86° C. bath, following which 5α-chloro-6β,19 -epoxyandrostan-3β-ol-17-one (555.9 mg, 1.640 mmol) in 9.2 mL of warm anh. DMSO was added and the mixture stirred a further 1 h. The reaction was then poured into 25 mL of ice-brine and extracted three times with 10 mL portions of ether. The combined organic extracts were washed with brine, dried over magnesium sulfate, and filtered through Celite. The residue was washed twice with 5 mL of ether and the combined filtrates were dried in vacuum. The residual yellow oil was purified by flash chromatography (60% ethyl acetate/hexanes on silica gel) to give a white syrupy solid (0.34 g, 0.97 mmol, 59%). (NA-1993B-97)

Example 12

5α-Chloro-6,β,19-epoxypregn-17-en-3-one, 12

A solution of 5α-chloro-6β,19-epoxypregn- 17-3β-ol (11, 0.34 g, 0.97 mmol) in 35 mL of acetone was cooled in an ice-acetone bath and 0.47 mL of 2.67M Jones reagent were added. After stirring 40 min. the reaction was quenched with the addition of 0.5 mL of 2-propanol. Water (15 mL) was added and the mixture was extracted three times with 15 mL portions of methylene chloride. The combined organic extracts were washed with 15 mL of saturated sodium bicarbonate+15 mL of brine, dried over magnesium sulfate, and filtered through Celite. After washing the residue twice with 5 mL of methylene chloride the combined filtrates were dried in vacuum. The residue was flash chromatographed on silica gel using 30% ethyl acetate/hexanes as eluent to give a white crystalline solid (0.34 g, 0.97 mmol, quantitative). (NA-1993B-100)

Example 13

6β,19-Epoxypregna-4,17-dien-3-one, 13

5α-chloro-6β,19-epoxypregn-17-en-3-one (12, 0.34 g, 0.97 mmol) was dissolved with warming in 10 mL of anh. methanol, potassium acetate (0.60 g, 6.1 mmol) was added, and 6.5 mL of solvent were distilled off at room pressure. The residue was concentrated under reduced pressure, taken up in 25 mL of water, and extracted three times with 10 mL portions of methylene chloride. The combined organic extracts were dried over magnesium sulfate and filtered through Celite. The residue was washed with 10 mL of methylene chloride and the combined filtrates concentrated under reduced pressure to give a white crystalline solid (290.0 mg, 0.9281 mmol, 96%) homogeneous to TLC (60% ethyl acetate/hexanes on silica gel; 0.61). (NA-1993B-101)

Example 14

Pregna-4,17-dien-19-ol-3-one, 14

To a solution of 6β,19-epoxypregna-4,17-dien- 3-one (290.0 mg, 0.9281 mmol) in 10 mL of glacial acetic acid was added zinc dust (1.12 g, 17.1 mg-atom) activated by stirring 2 min. with 10% hydrochloric acid followed by washing with water and acetone. The suspension was stirred vigorously for 10 min. in a 99°–102° C. and was then filtered through Celite. The residue was washed 4 times with 10 mL of acetic acid and the combined filtrates were concentrated in vacuum. The residue was taken up in 50 mL of ethyl acetate. washed with 50 mL of water+50 mL of saturated sodium bicarbonate+50 mL of brine, dried over magnesium sulfate, and filtered through Celite. The residue was washed with 10 mL of ethyl acetate and the combined filtrates dried in vacuum. The residue was recrystallized from ethyl acetate to give white crystals (46.4 mg, 0.148 mmol, 16%) , m.p. 192°–195° C. (NA-1993B-102)

Example 15

Pregn-4-en-3β-ol-20-yne, 15

Pregn-4-en-3-ol-20-yn, 15:

Pregn-4-en-3-on-20-yne (200.1 mg, 0.6750 mmol) and lithium aluminum tri(t-butoxy)hydride (343.8 mg, 1.352 mmol) were suspended in 3.6 mL of anhydrous ether. After reacting 4 h, a further 343.5 mg (1.351 mmol) of hydride were added and the reaction was allowed to continue 16 h. See Scheme 4. After quenching with sodium sulfate decahydrate (3.41 g) the reaction mixture was agitated 15 min. and then filtered through diatomaceous earth. The residue was extracted 5 times with 10 mL portions of ether and the combined filtrates were concentrated under reduced pressure. Flash chromatography of the residue (25% ethyl acetate/hexanes on silica gel) followed by recrystallization from aqueous ethanol yielded a white powder (85.0 mg, 0.285 mmol, 42%), m.p. 120.5°–123.5° C. (NA-1994A-235)

Example 16

Measurement of Autonomic Responses to Stimulation of the VNO.

Various autonomic parameters were monitored

Figure 2:
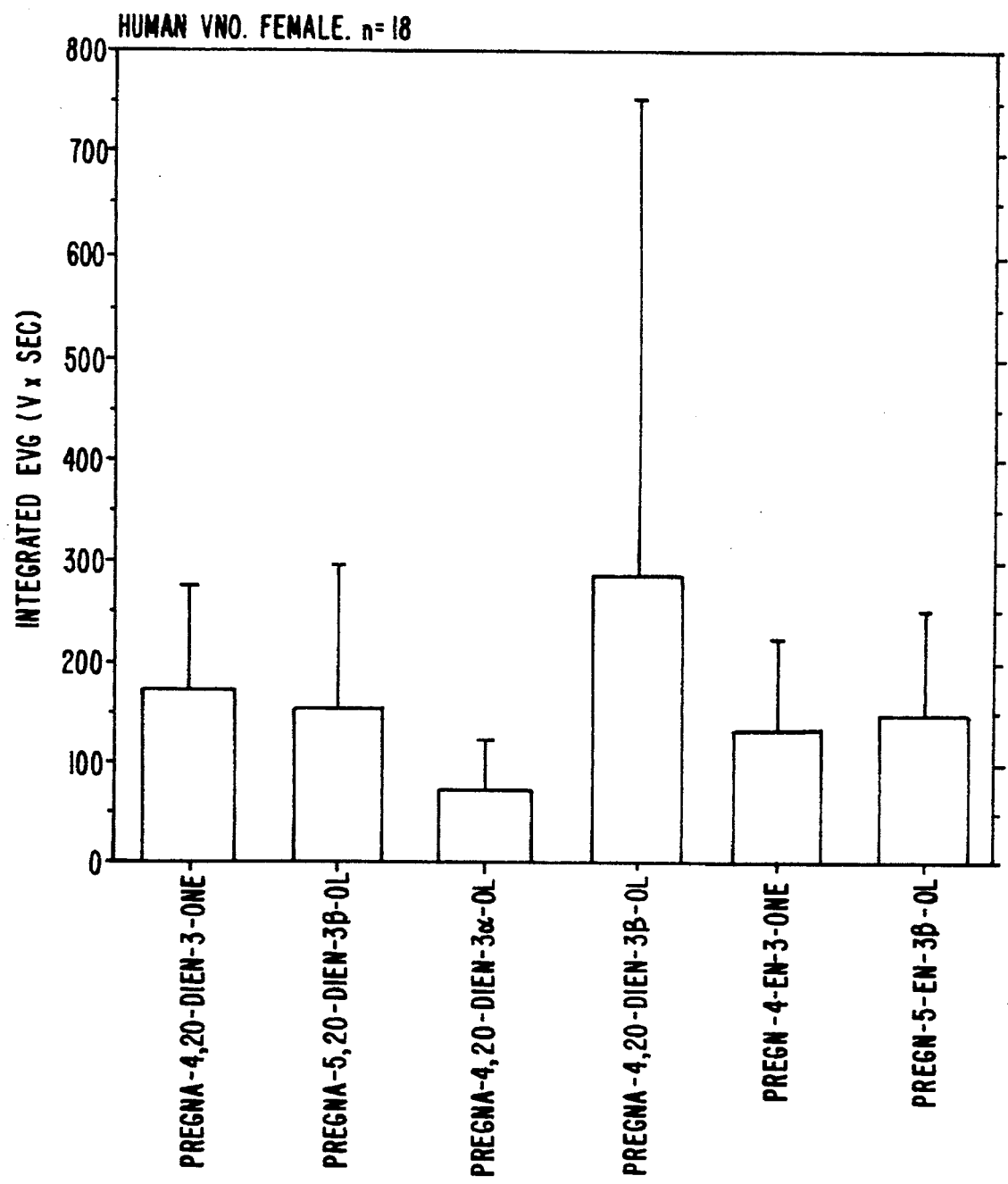
FIG. 2 is the data for the integrated EVG for compounds A1-P1, A2-P1, A4-P1, A3-P1, A1-P4, A2-P4 in females.
Figure 3:
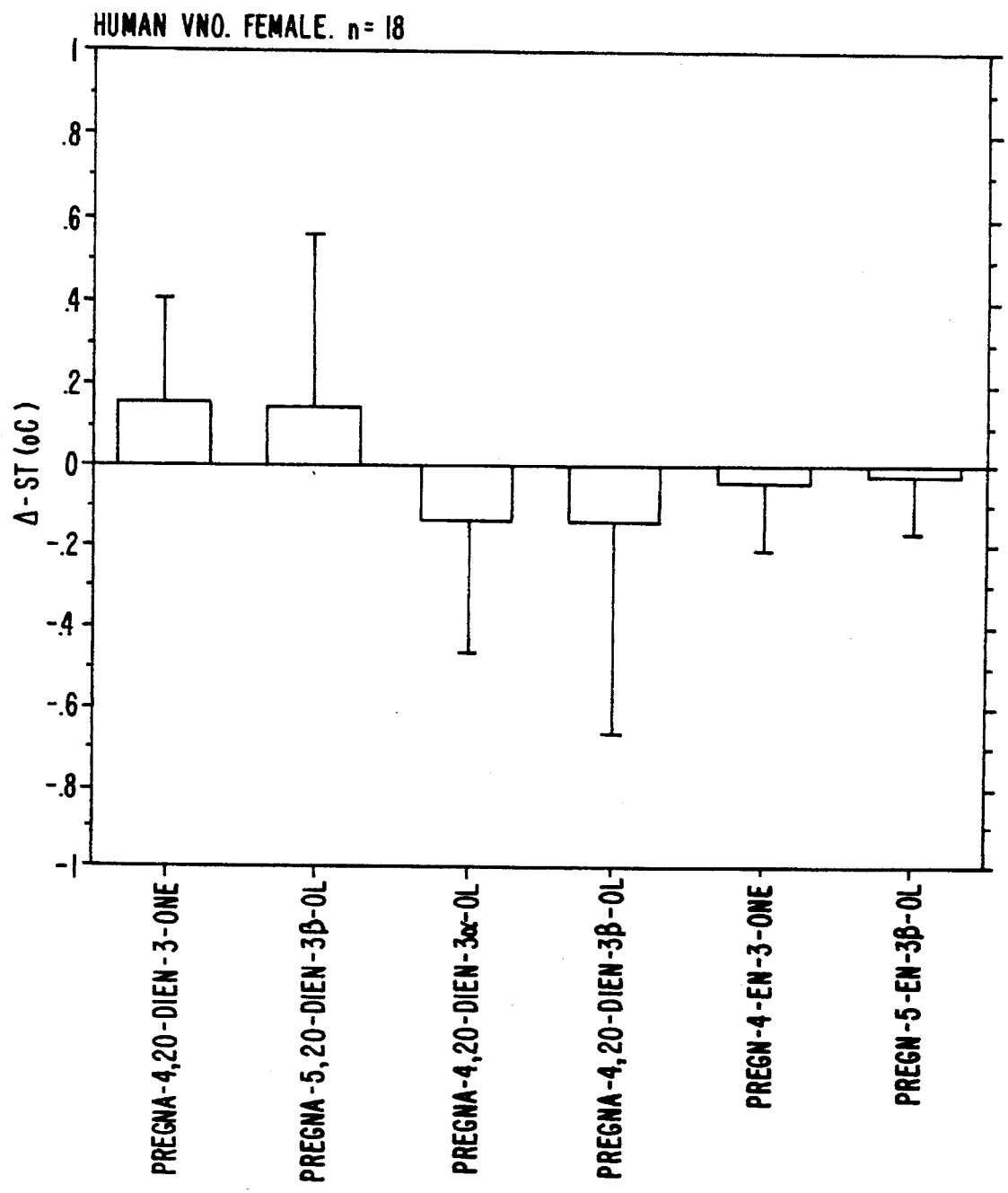
FIG. 3 is the data for the ST measurements of compounds A1-P1, A2-P1, A4-P1, A3-P1, A1-P4, A2-P4 in females.
Figure 4:
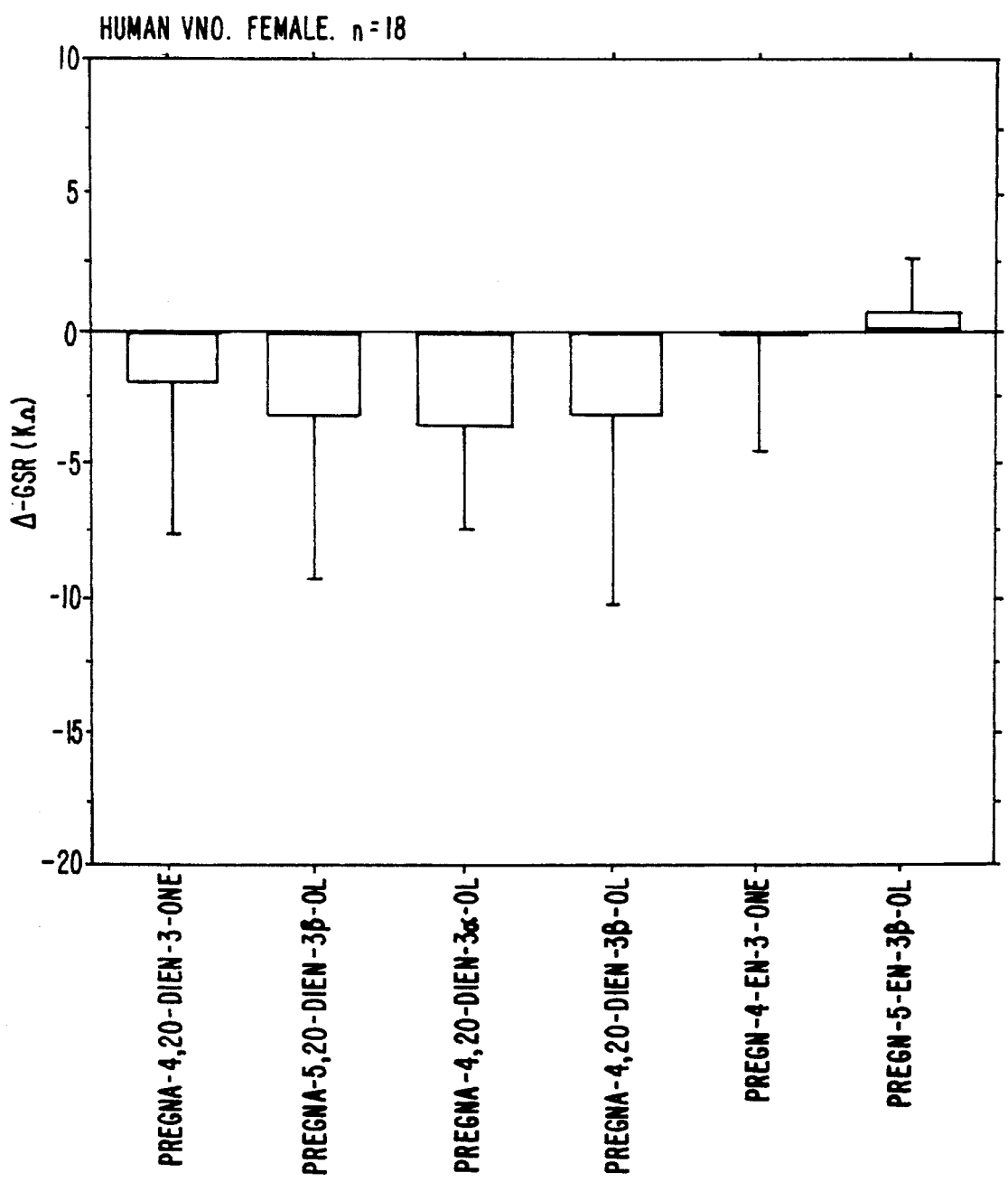
FIG. 4 is the data for the GSR measurements in females of compounds A1-P1, A2-P1, A4-P1, A3-P1, A1-P4, A2-P4.
Figure 5:
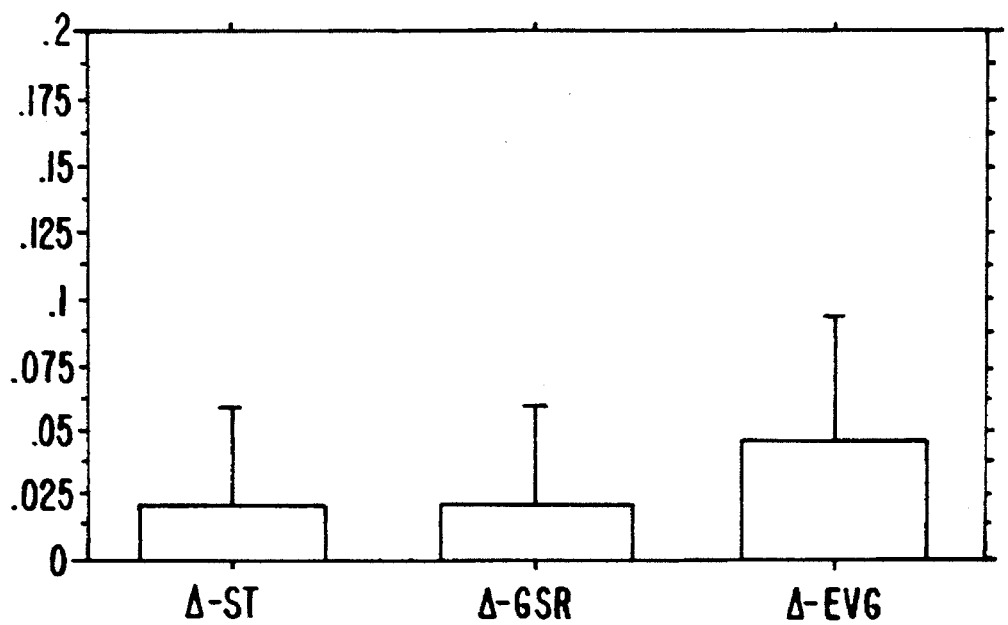
FIG. 5 is the data for ST, GSR and EVG measurements in females of compound A1-P3.
Figure 6:
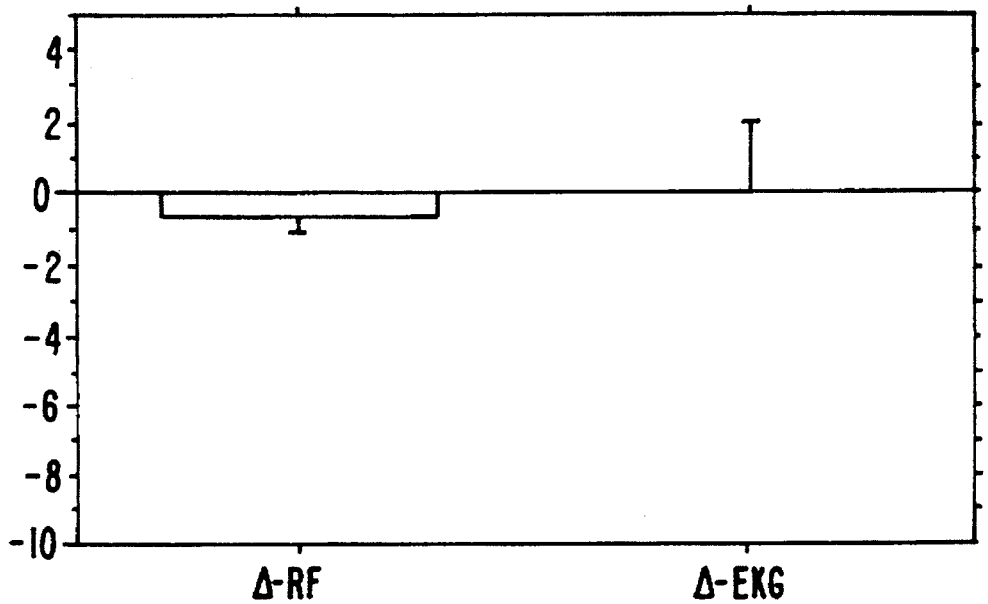
FIG. 6 is the data for RF and EKG measurements in females of compound A1-P3.
Figure 7:
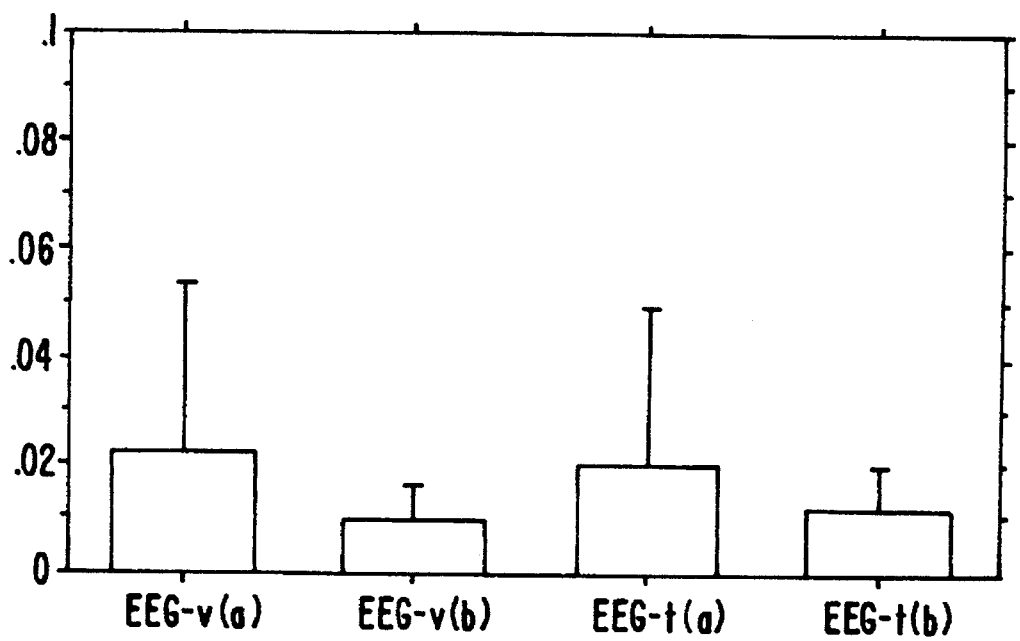
FIG. 7 is the data for EEG measurements in females of the compound A1-P3.
Figure 8:
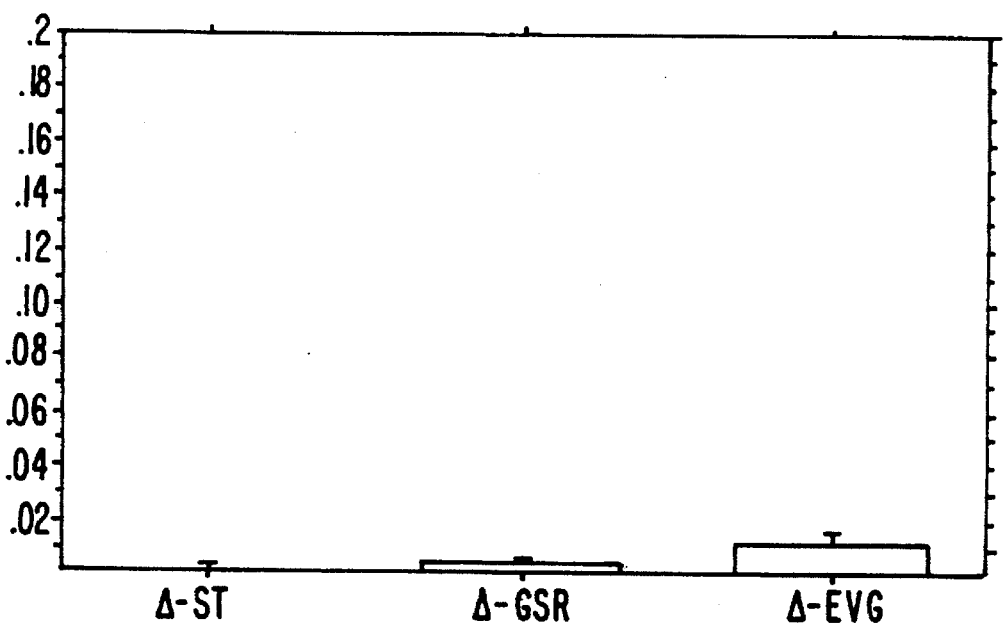
FIG. 8 is the data for the ST, GSR and EVG measurements in males of compound A1-P3.
Figure 9:
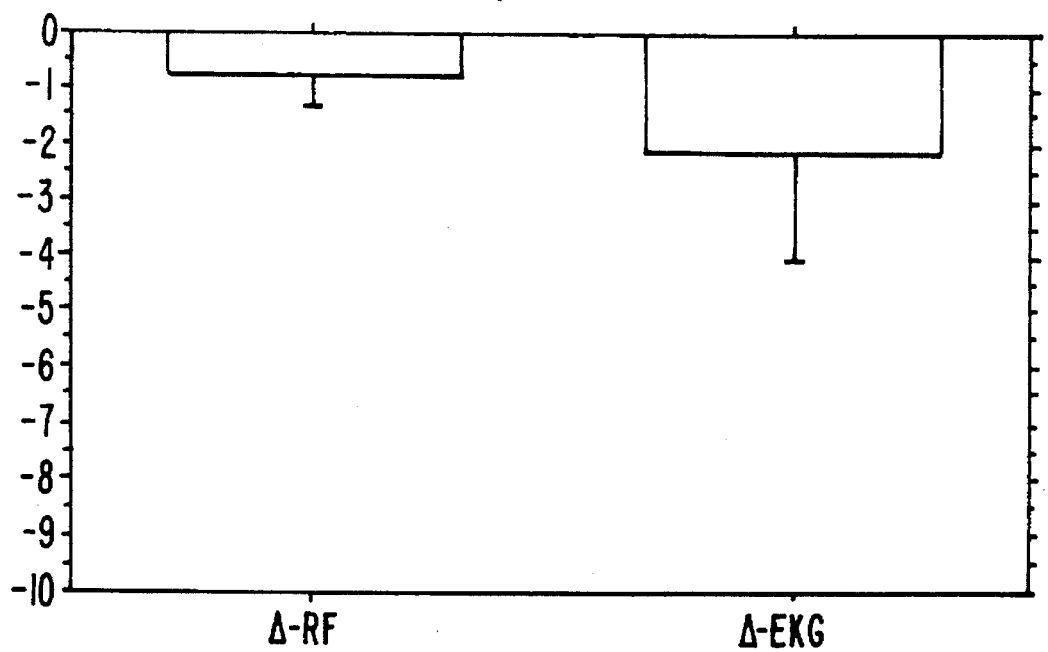
FIG. 9 is the data for the RF and EKG measurements in males of compound A1-P3.
Figure 10:
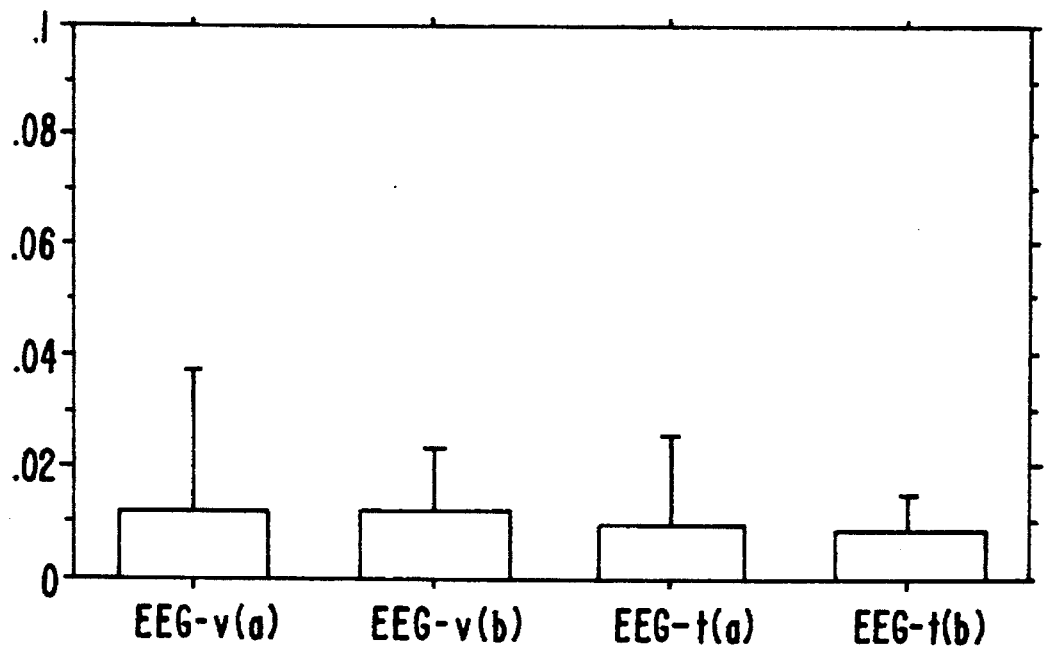
FIG. 10 is the data for the EEG measurements in males of compound A1-P3.
Figure 11:
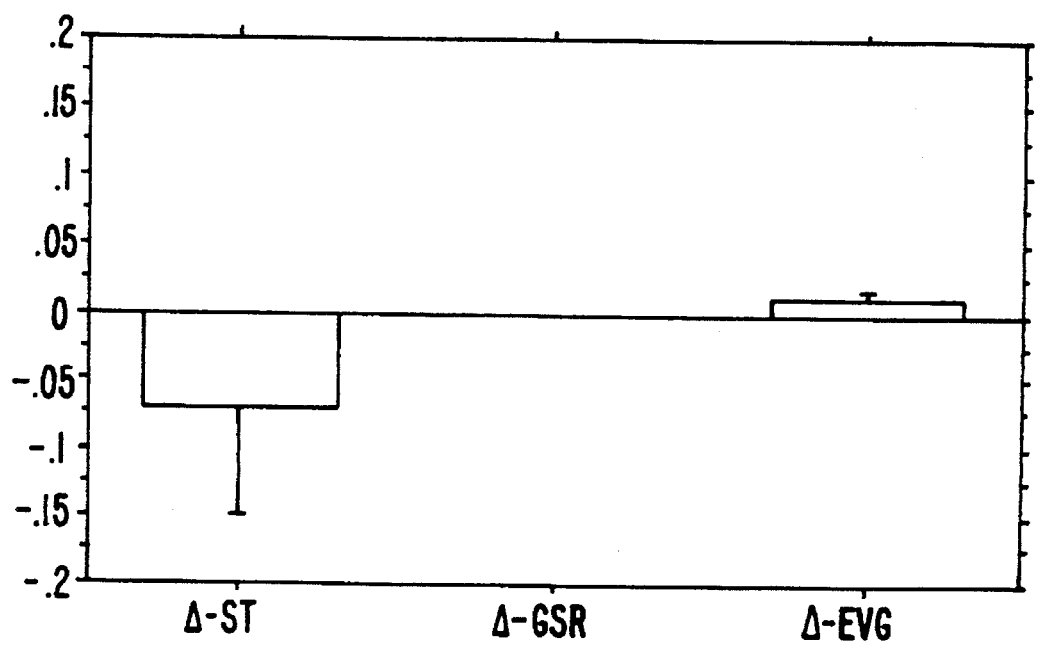
FIGS. 11 and 12 show the data of the ST, GSR and EVG measurements in males and females, respectively, for compound A2-P3.
Figure 12:
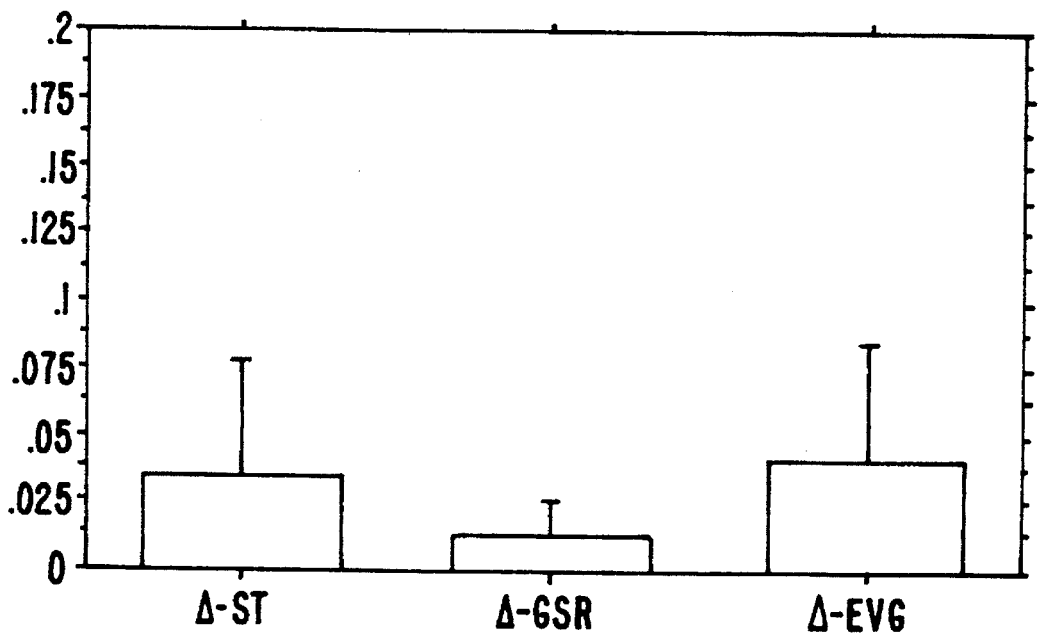
Figure 13:
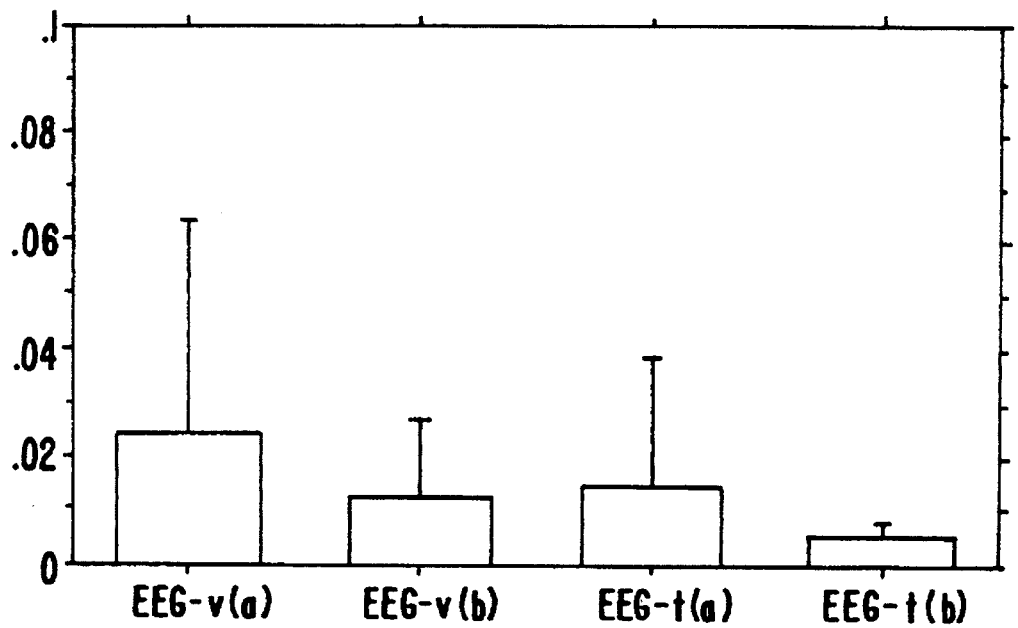
FIGS. 13 and 14 show the data of the EEG measurements in males and females, respectively, for compound A2-P3.
Figure 14:
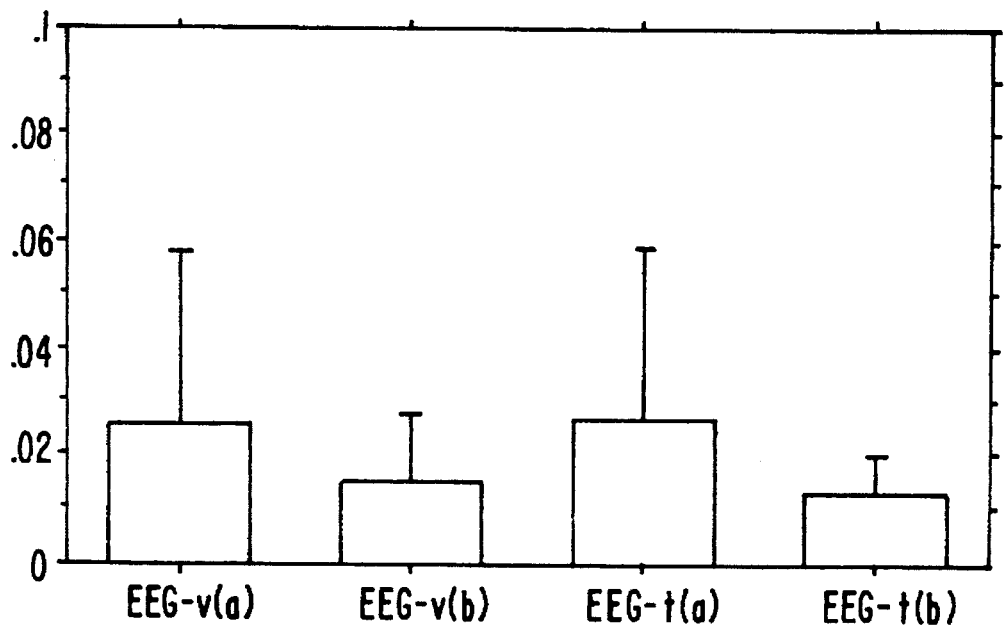
Figure 15:
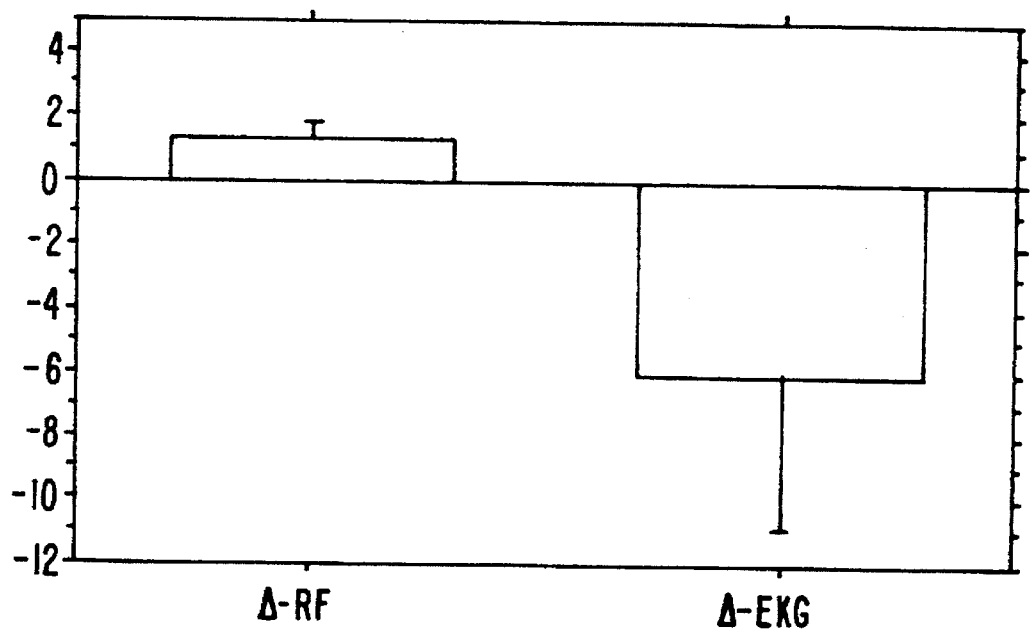
FIGS. 15 and 16 show the data for the RF and EKG measurements in males and females, respectively, for compound A2-P3.
Figure 16:
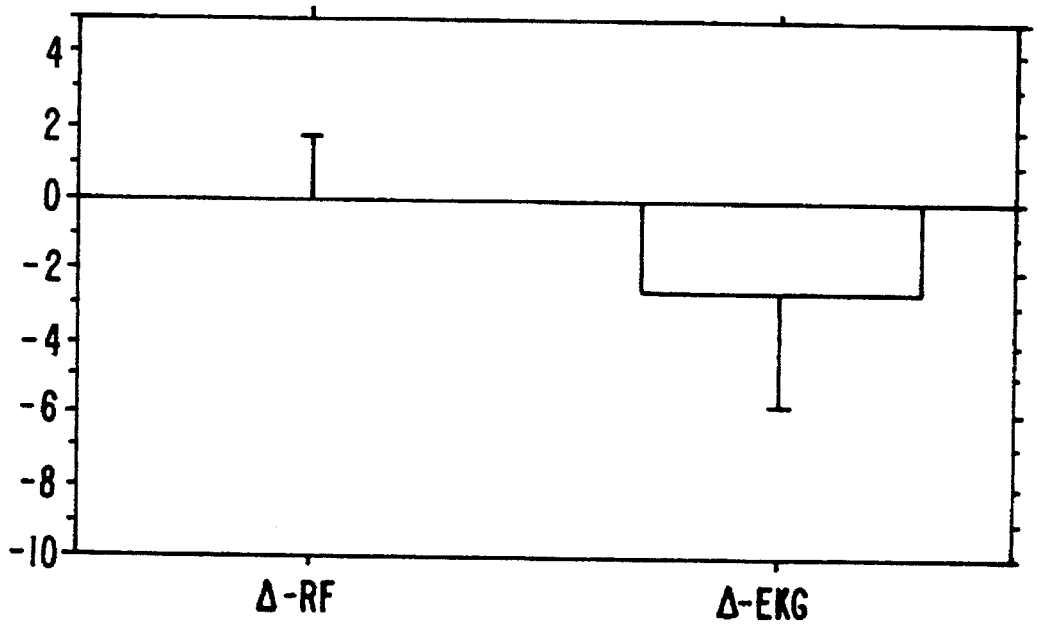
Figure 17:
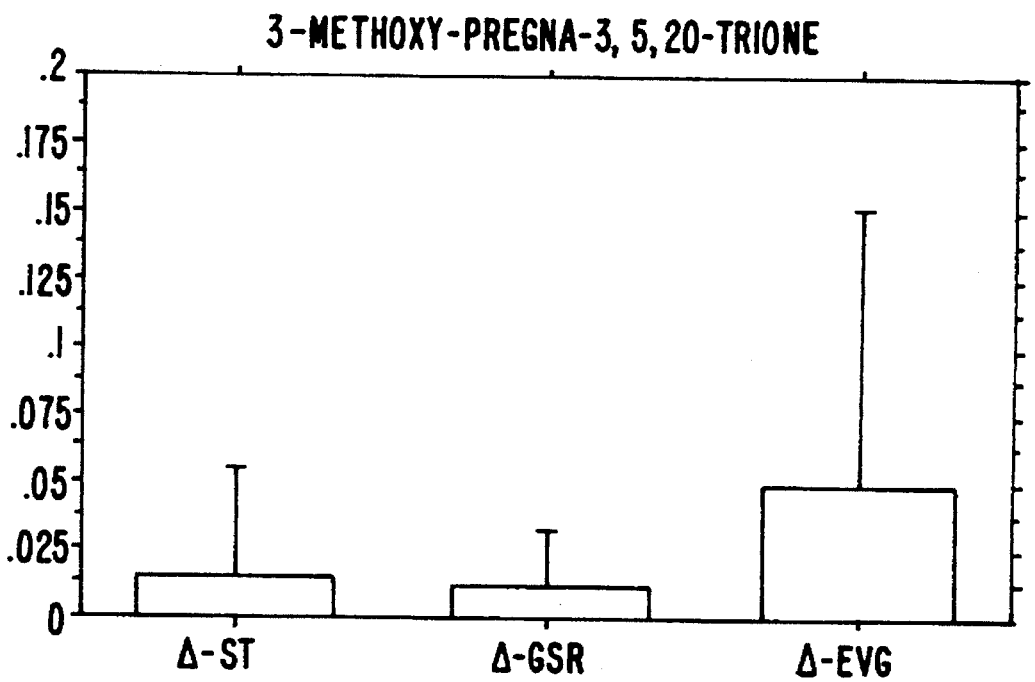
FIGS. 17 and 18 show the data of the ST, GSR and EVG measurements in males and females, respectively, for compound A8-P1.
Figure 18:
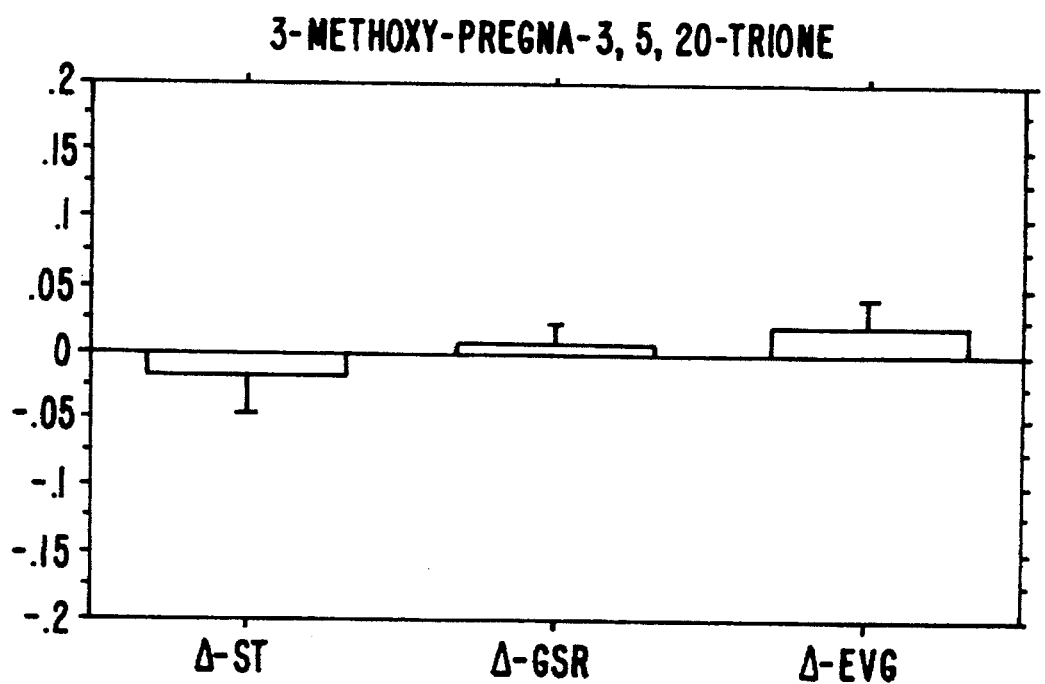
Figure 19:
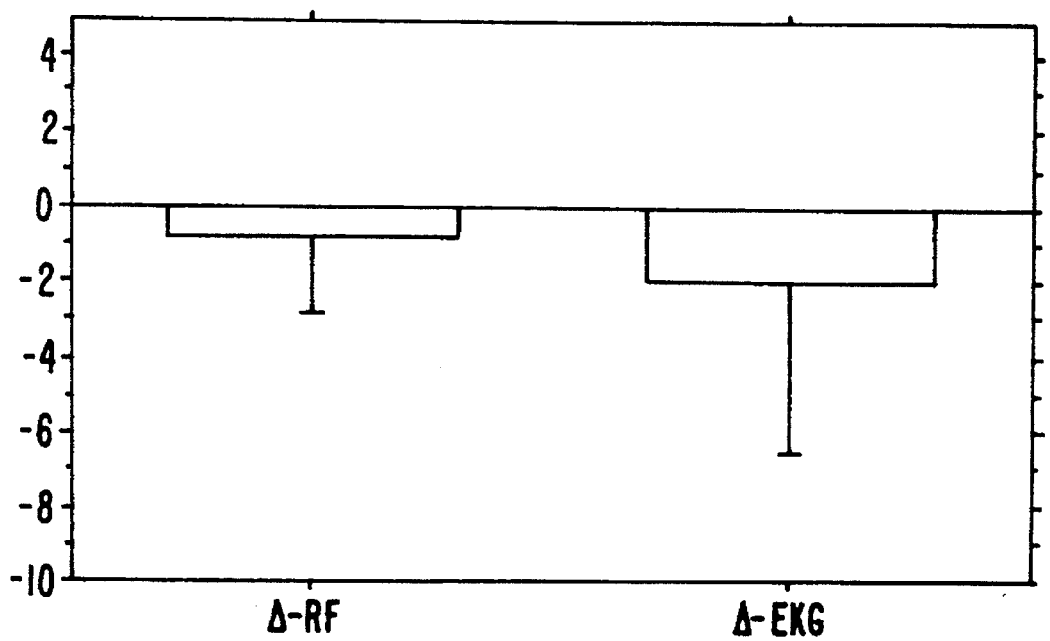
FIGS. 19 and 20 show the data of the RF and EKG measurements in males and females, respectively, for compound A8-P-1.
Figure 20:
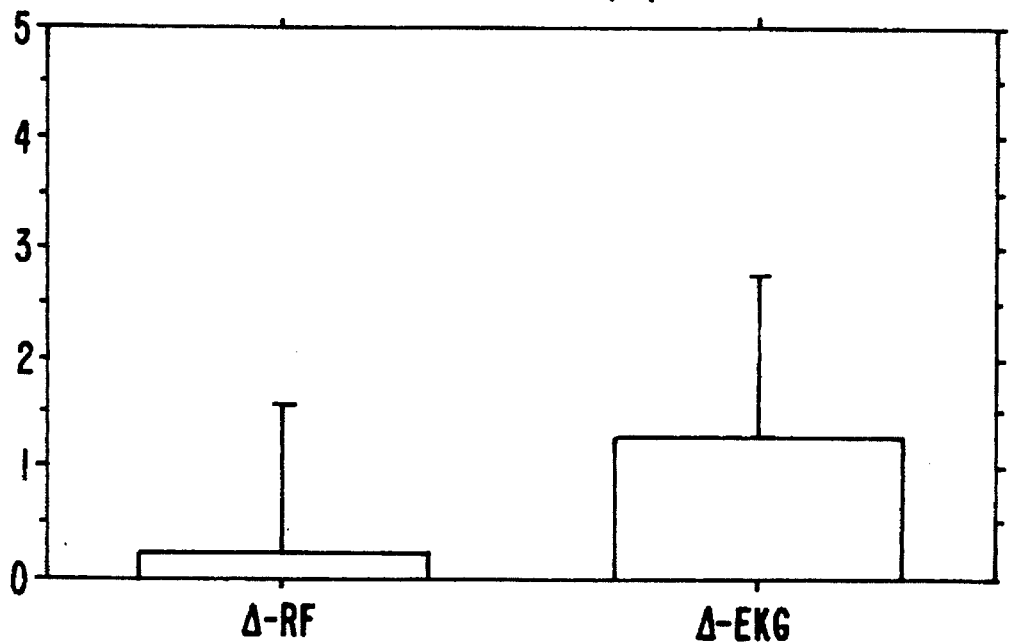
Figure 21:
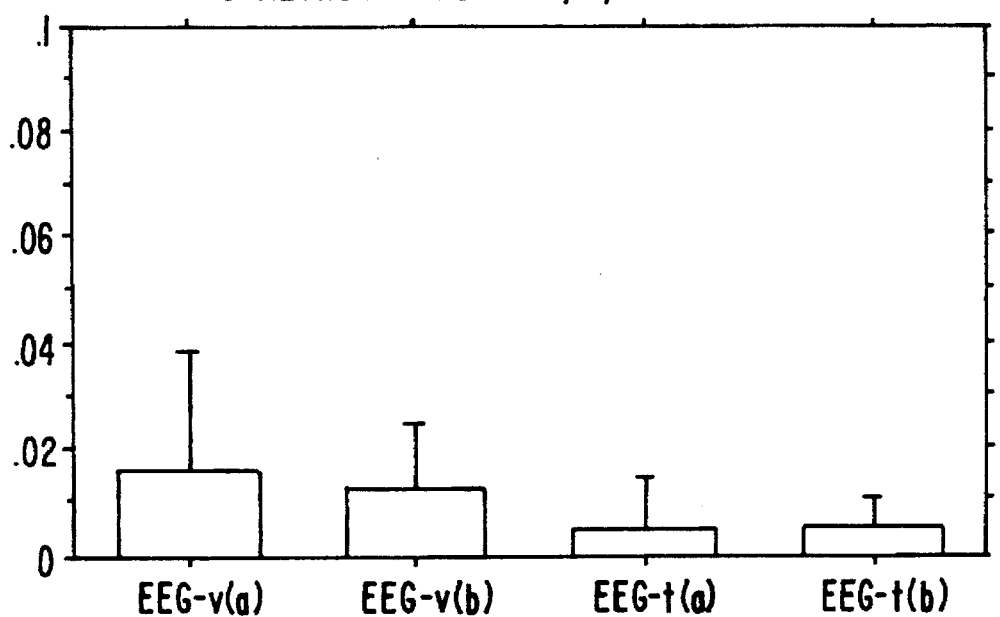
FIGS. 21 and 22 show the data for EEG measurements in males and females, respectively, for compound A8-P1.
Figure 22:
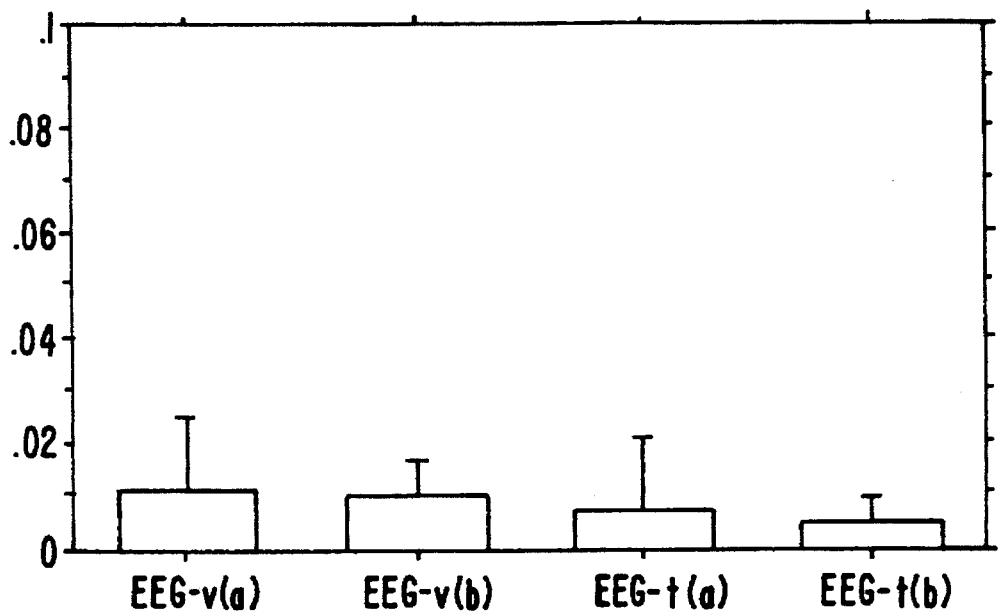
Figure 23:
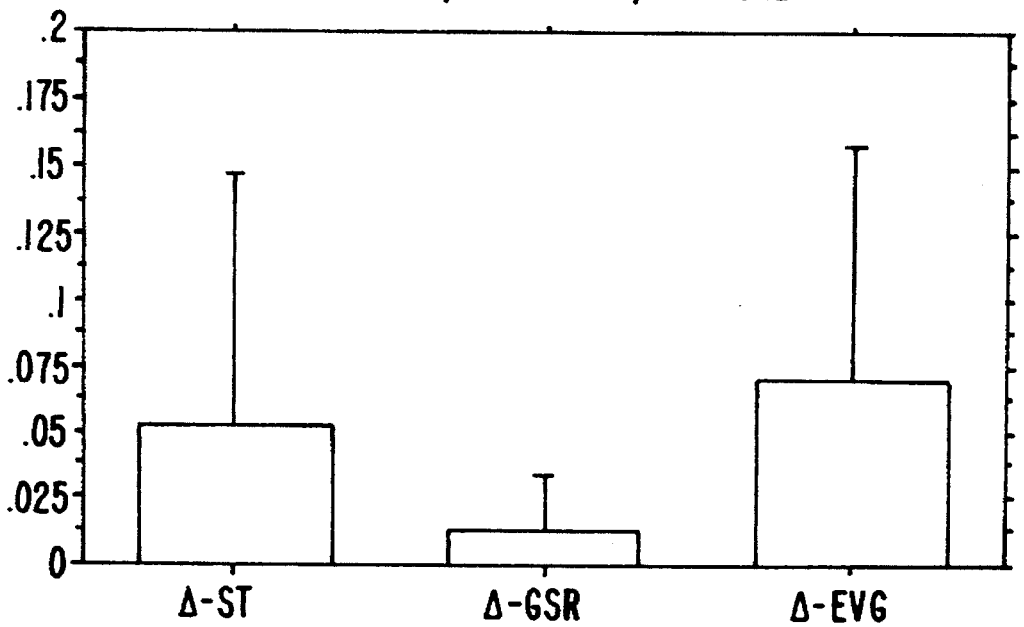
FIGS. 23 and 24 show the data for ST, GSR and EVG measurements in males and females, respectively, for compound A6-P1.
Figure 24:
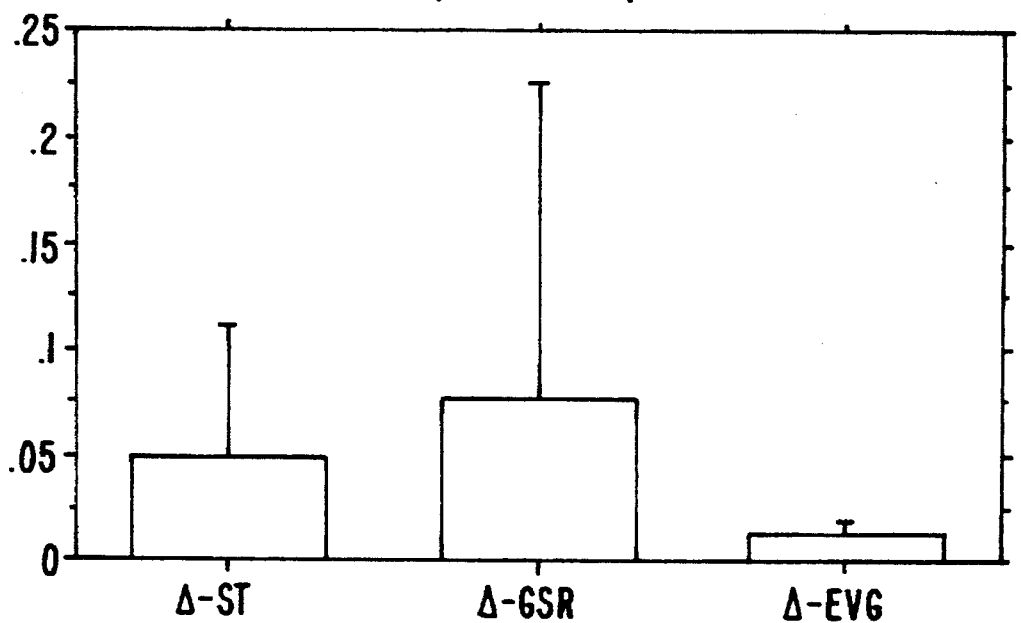
Figure 25:
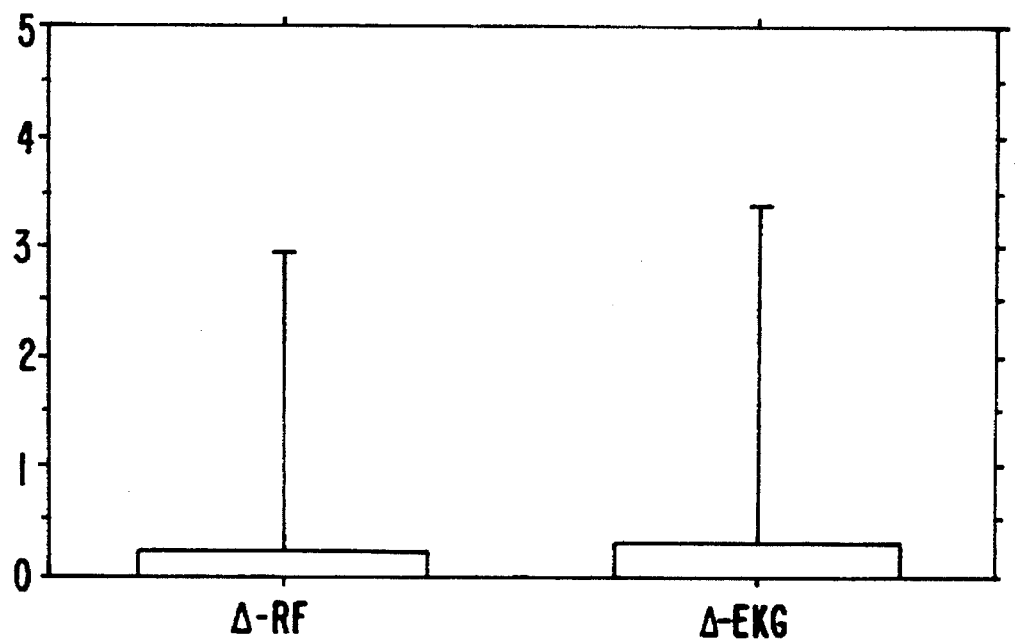
FIGS. 25 and 26 show the data for RF and EKG measurements in males and females, respectively, for compound A6-P1.
Figure 26:
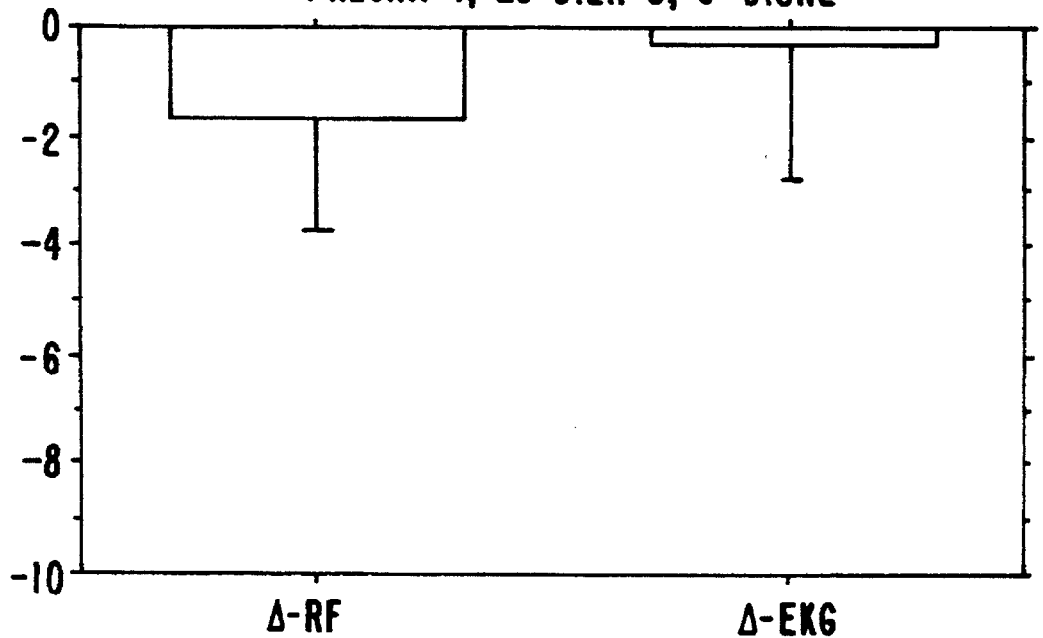
Figure 27:
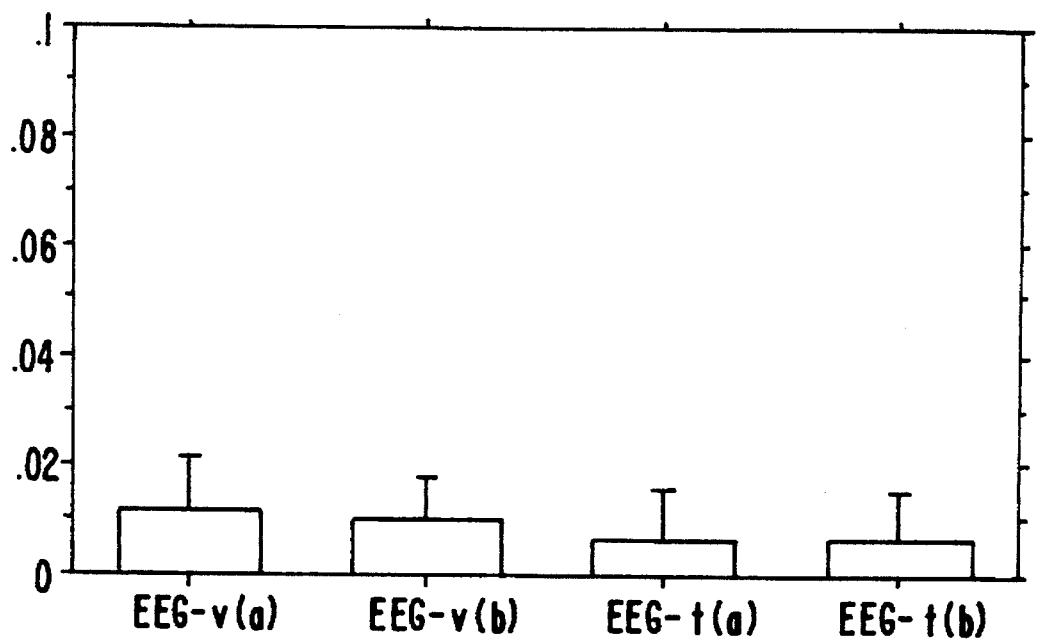
FIGS. 27 and 28 show the data for EEG measurements in males and females, respectively, for compound A6-P1.
Figure 28:
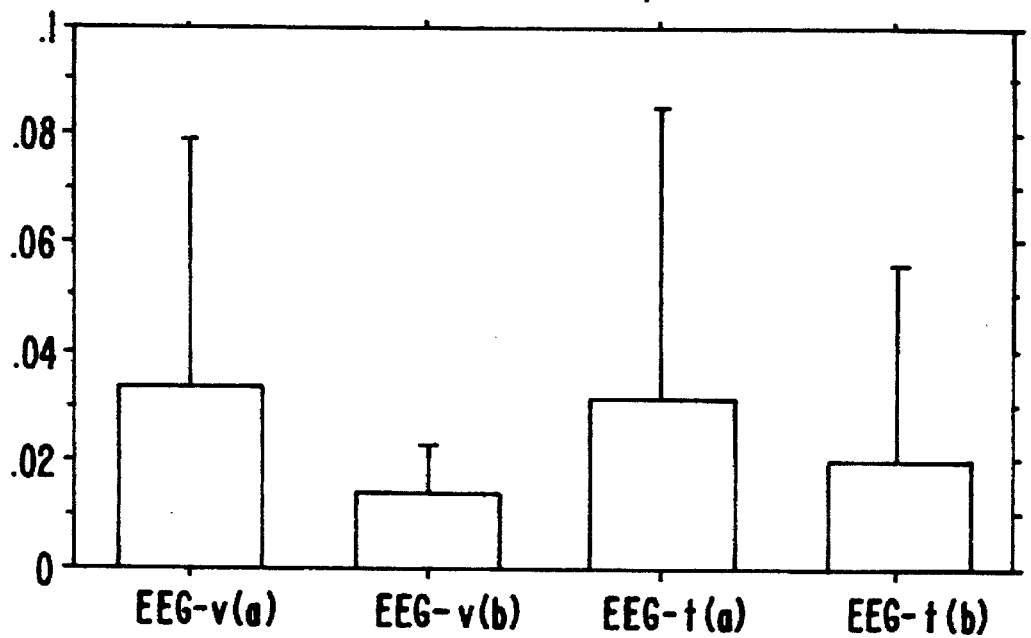
Figure 29:
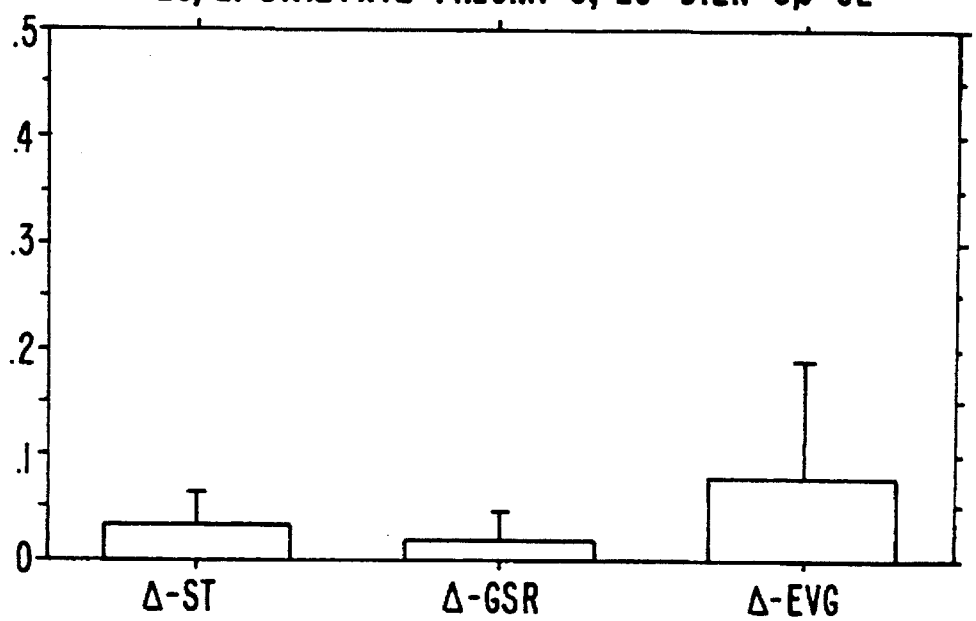
FIGS. 29, 30 and 31 show the data for ST, GSR, EVG, RF EKG and EEG measurements in males of 20,21-dimethylpregna-5,20-dien-3β-Ol.
Figure 30:
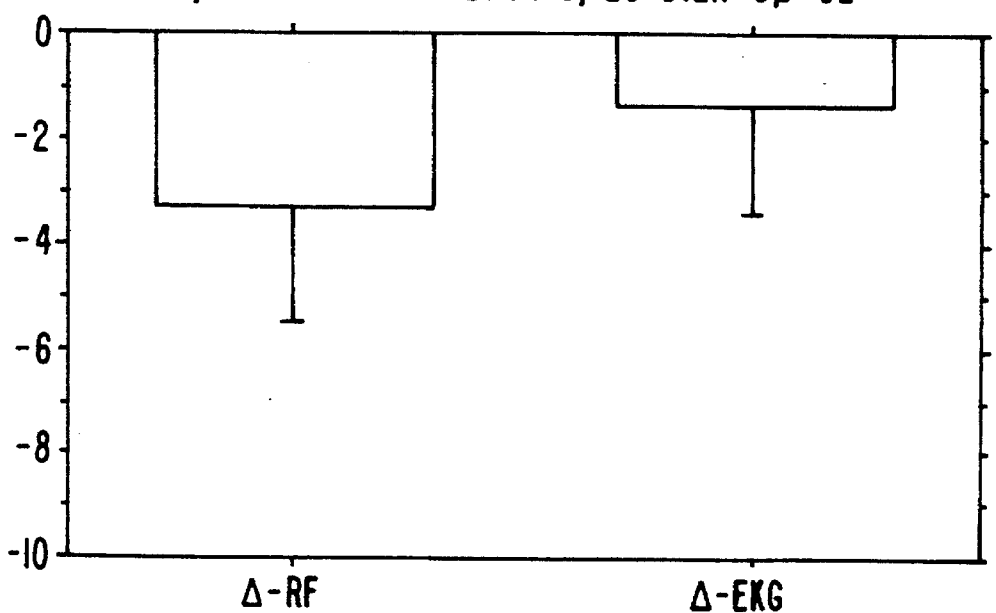
Figure 31:
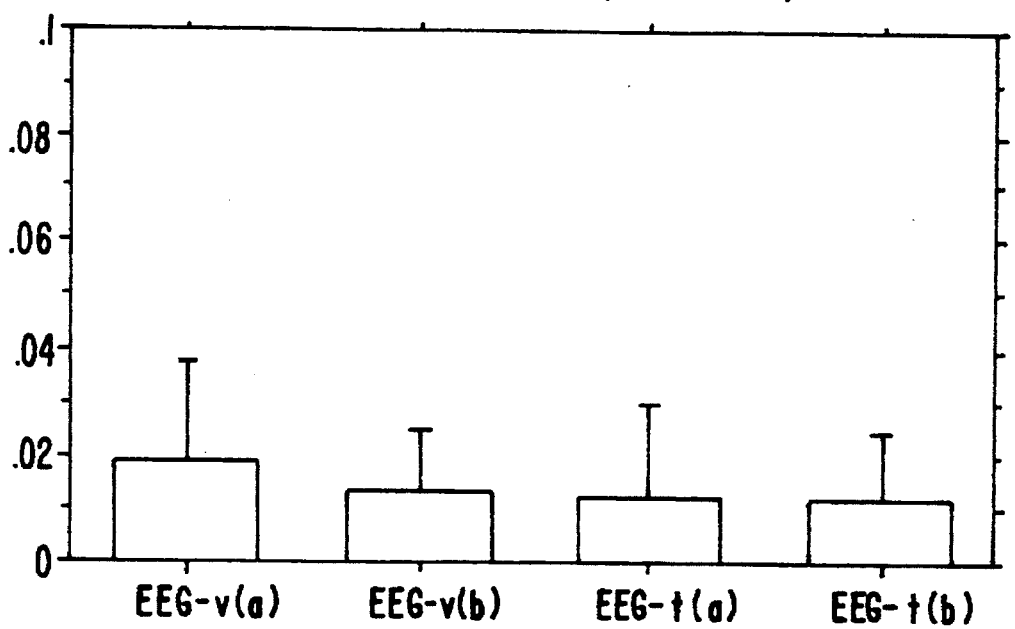
Figure 32:
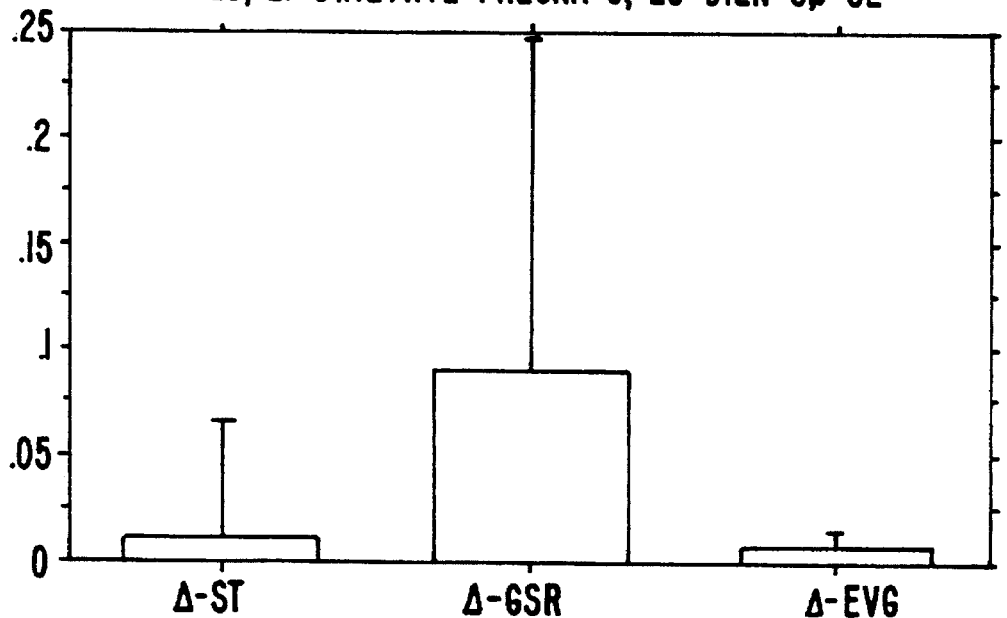
FIGS. 32, 33 and 34 show the data for the ST, GSR, EVG, RF EKG and EEG measurements in females of 20,21-dimethylpregna-5,20-dien-3β-Ol.
Figure 33:
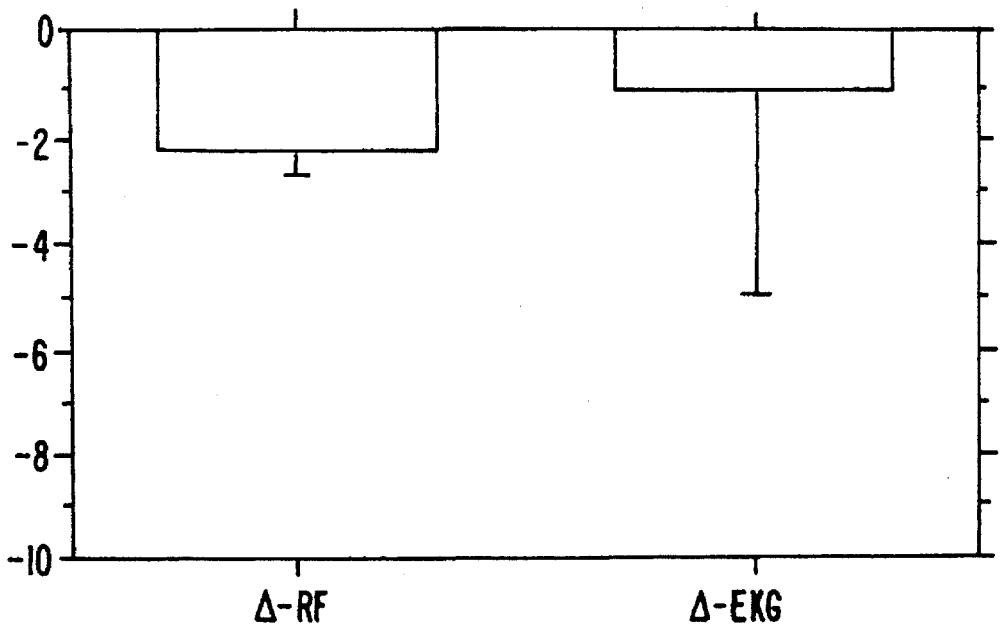
Figure 34:
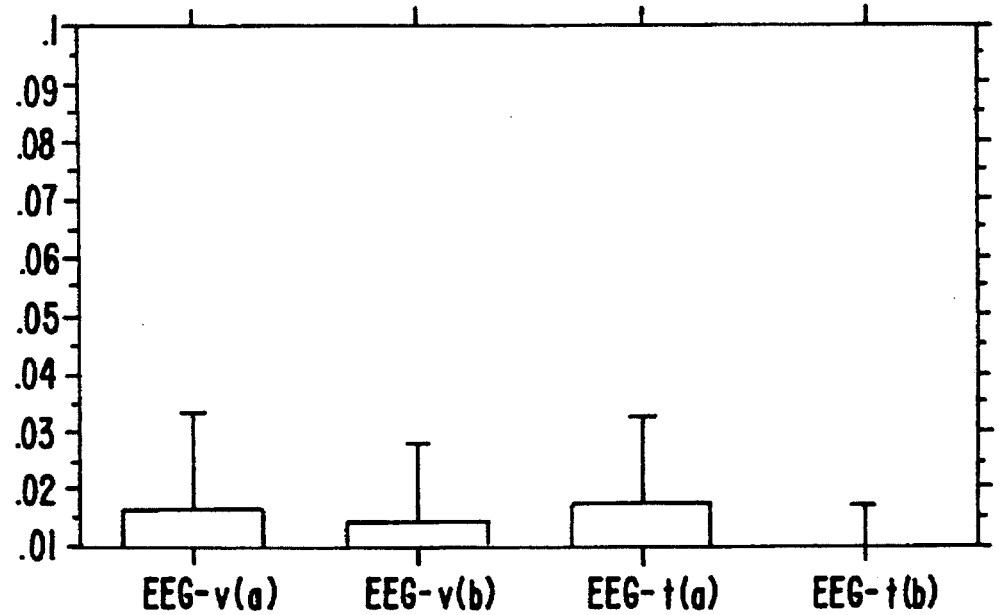
Figure 35:
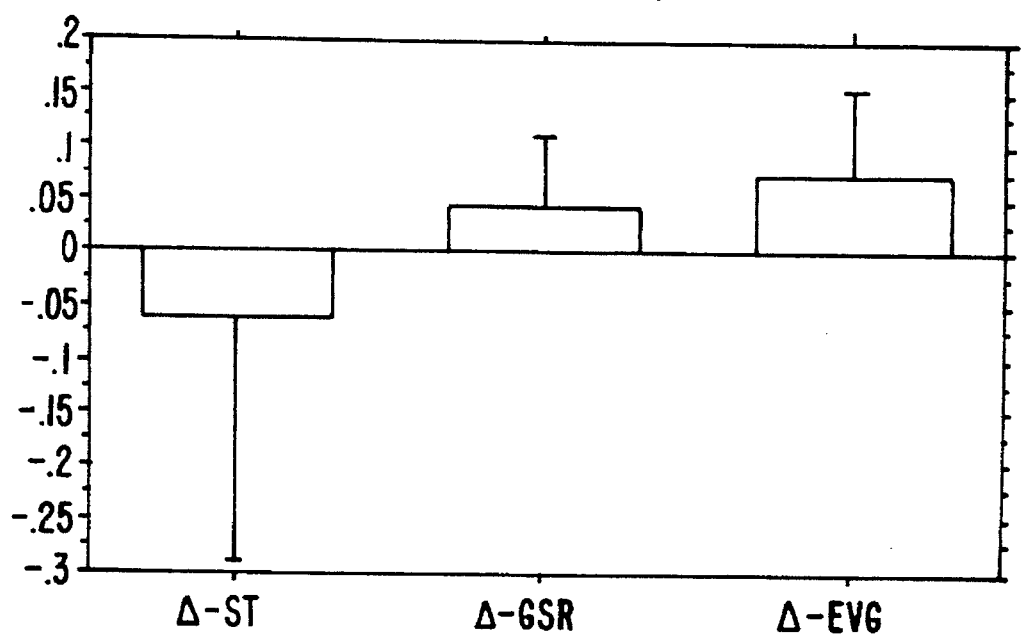
FIGS. 35, 36 and 37 show the data for the ST, GSR, EVG, RF EKG and EEG measurements in males of 20,21-dimethylpregna-5,20-dien-3-one.
Figure 36:
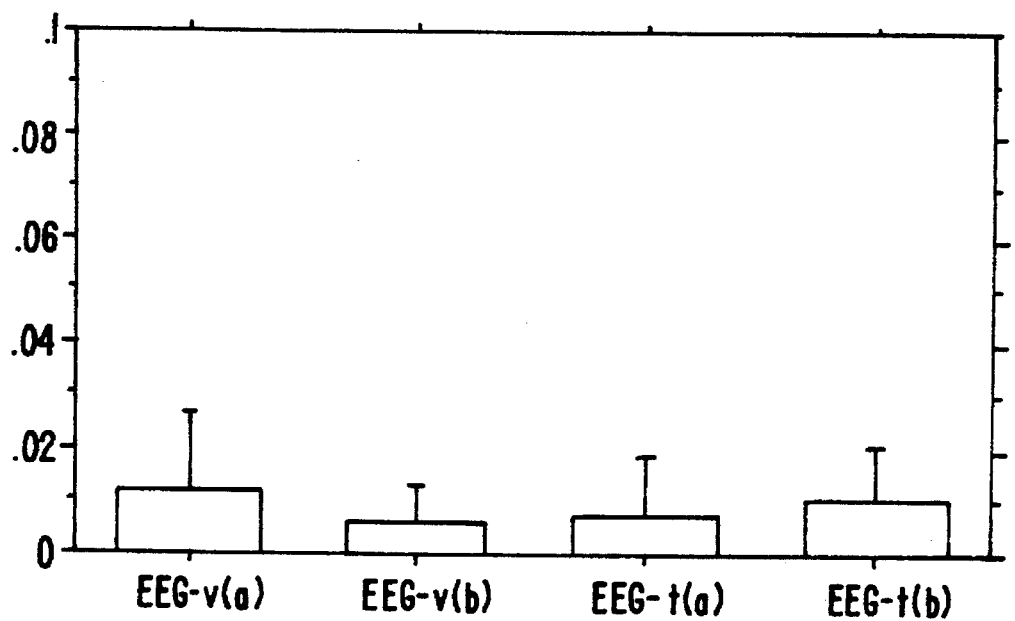
Figure 37:
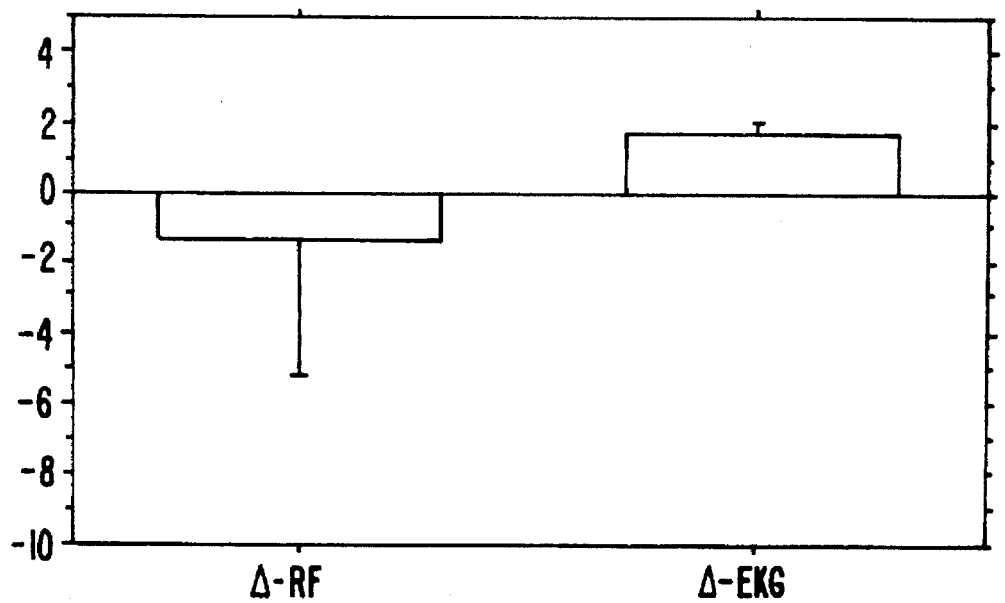
Figure 38:
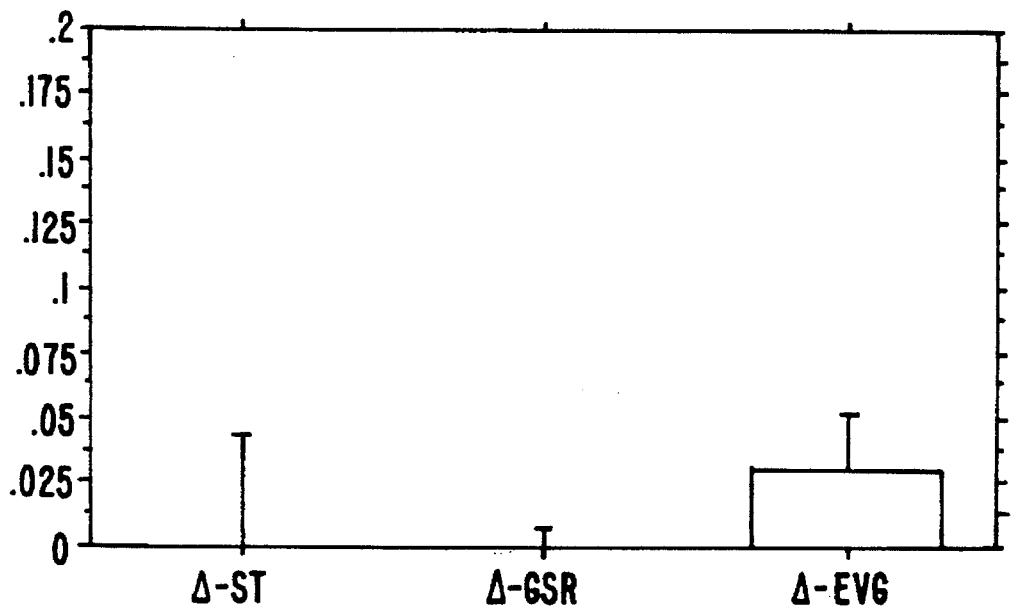
FIGS. 38, 39 and 40 show the ST, GSR, EVG, RF EKG and EEG measurements in females of 20,21-dimethylpregna-5,20-dien-3-one.
Figure 39:
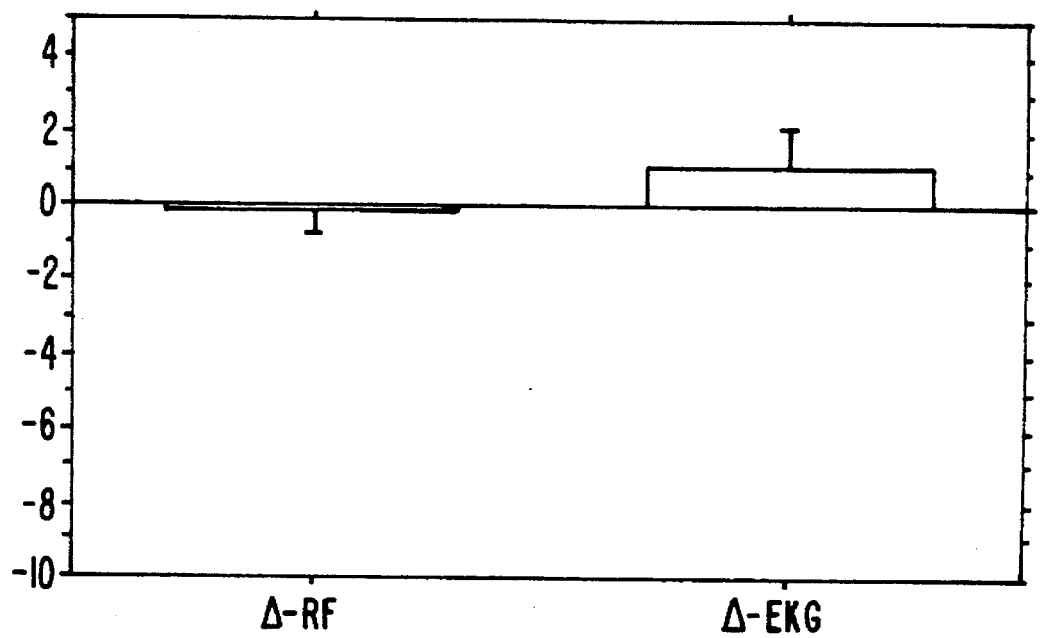
Figure 40:
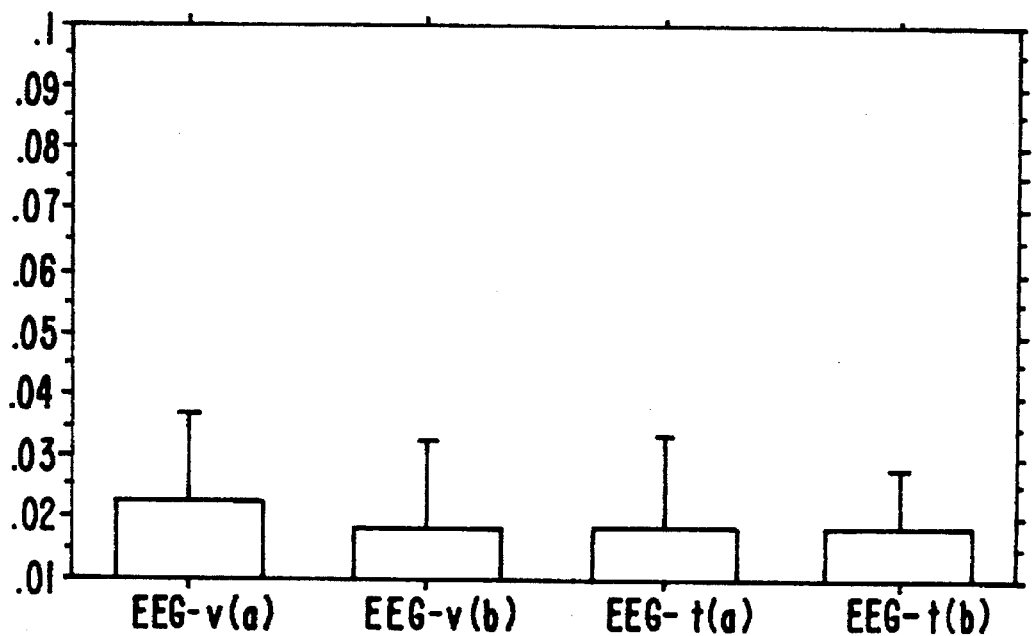
Figure 41:
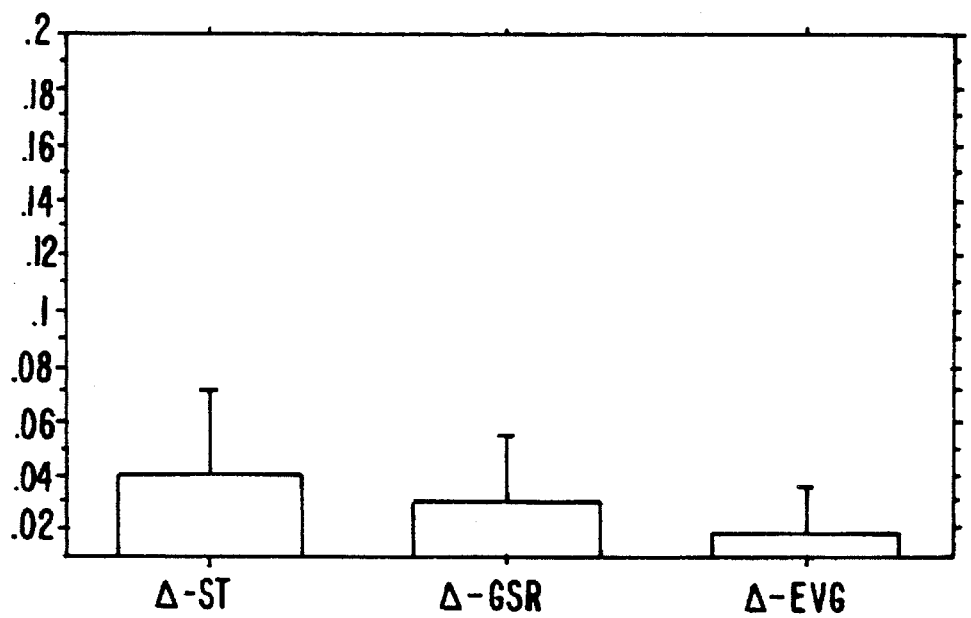
FIGS. 41, 42 and 43 show the ST, GSR, EVG, RF, EKG and EEG measurements in males of compound A14-P2.
Figure 42:
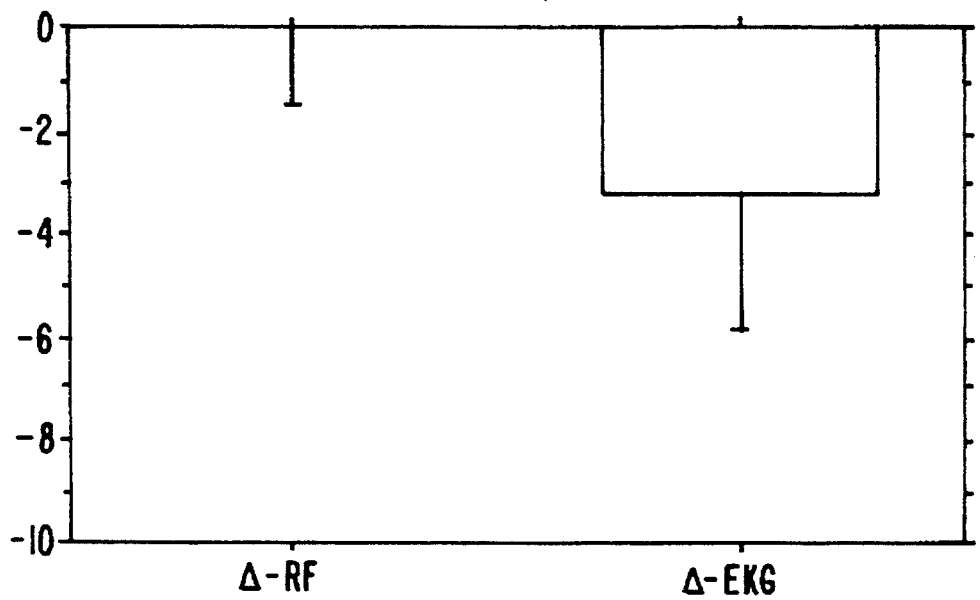
Figure 43:
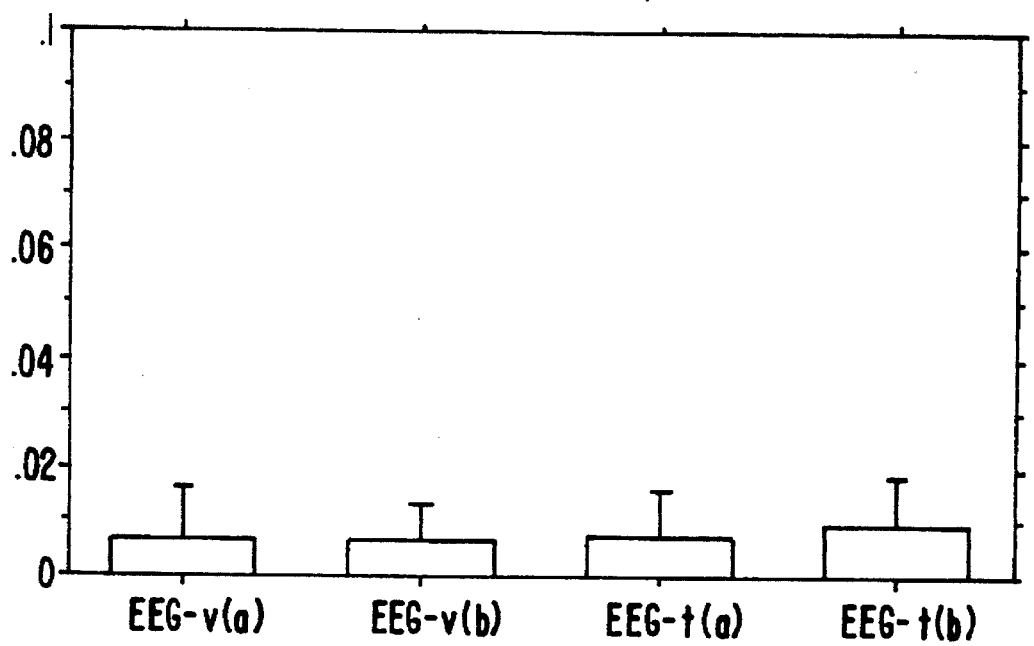
Figure 44:
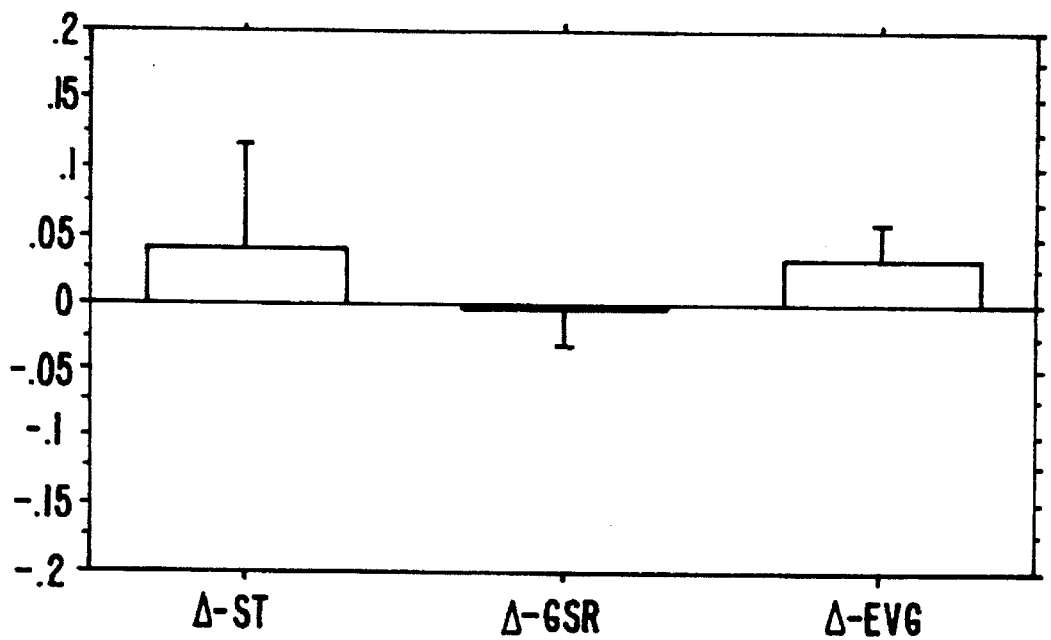
FIGS. 44, 45 and 46 show the ST, GSR, EVG, RF, EKG and EEG measurements in females of compound A14-P2.
Figure 45:
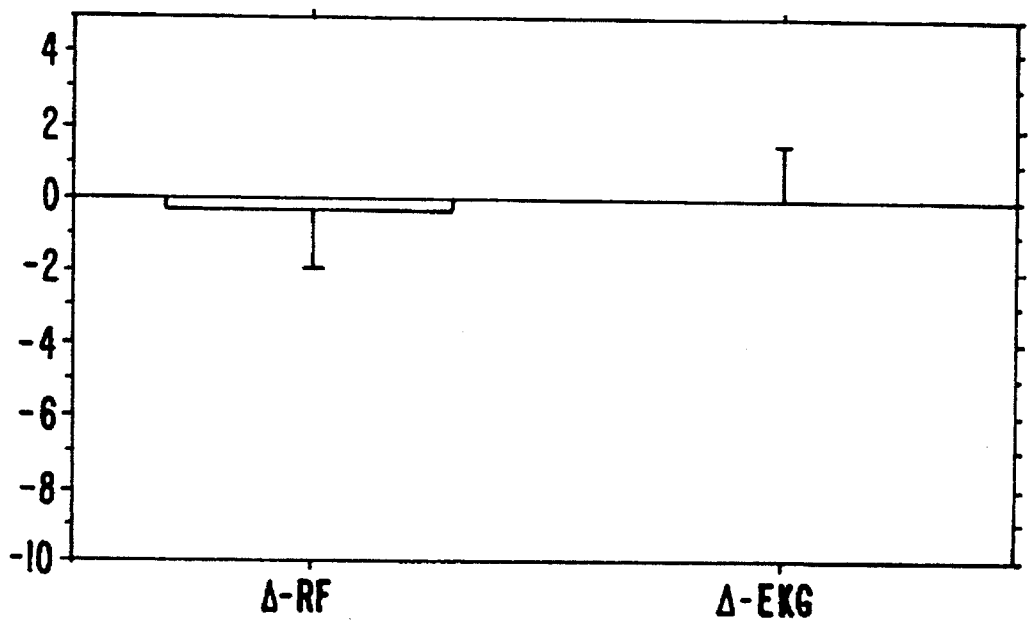
Figure 46:
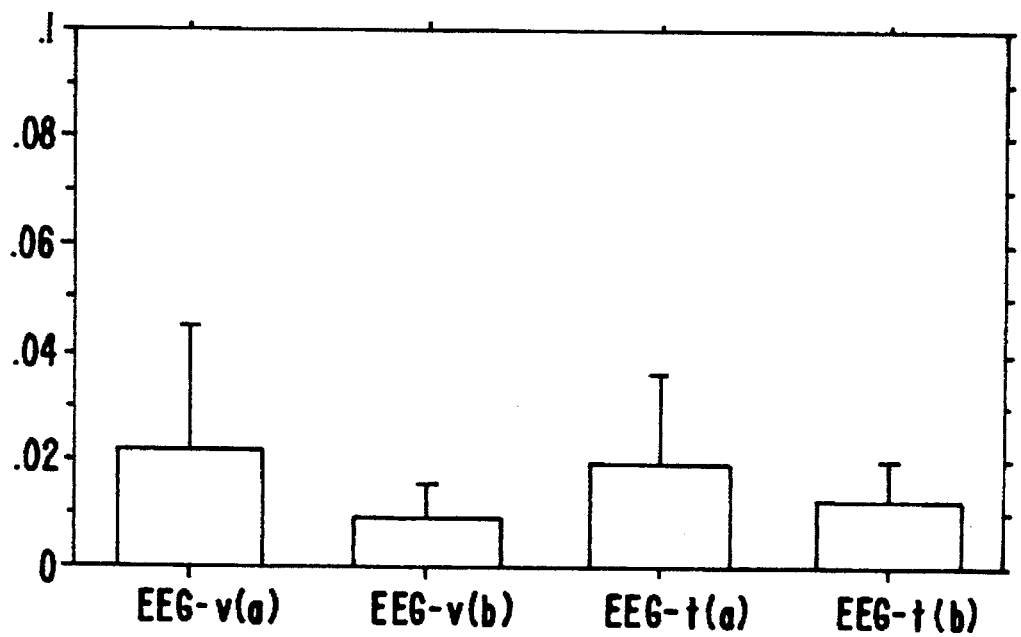
Figure 47:
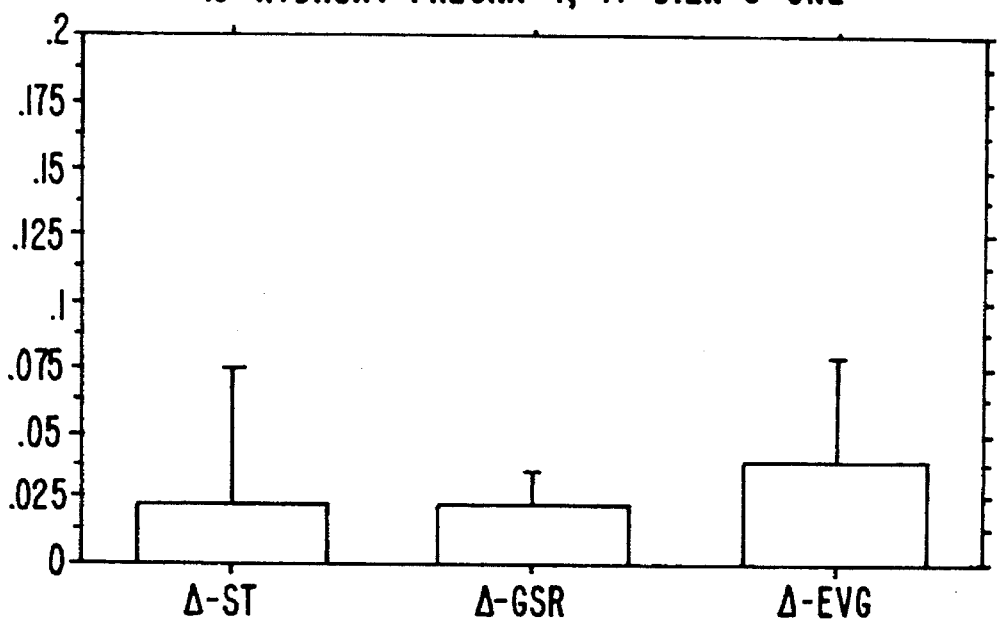
FIGS. 47, 48 and 49 show the ST, GSR, EVG, RF, EKG and EEG measurements in males of compound A7-P2.
Figure 48:
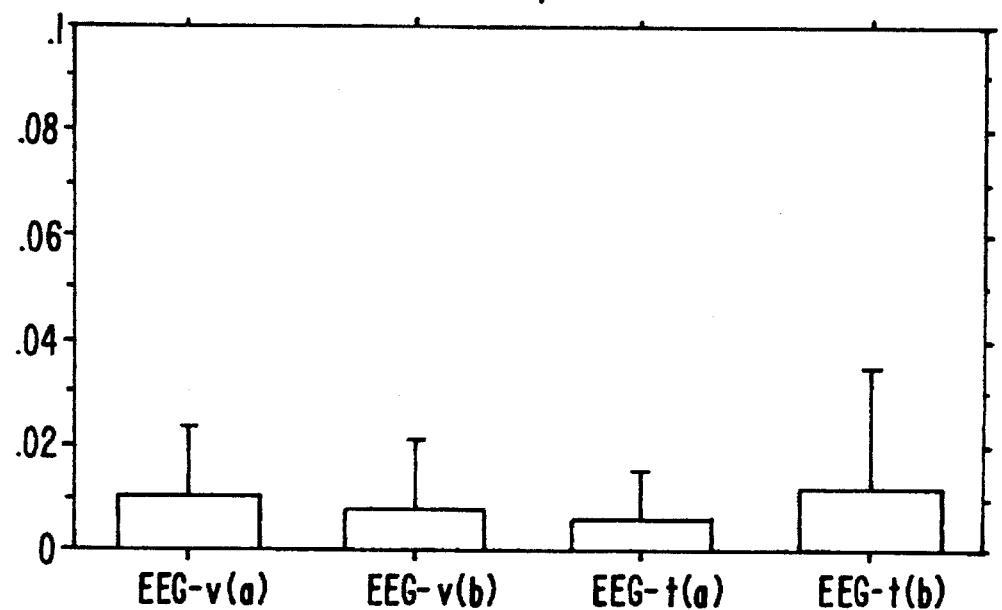
Figure 49:
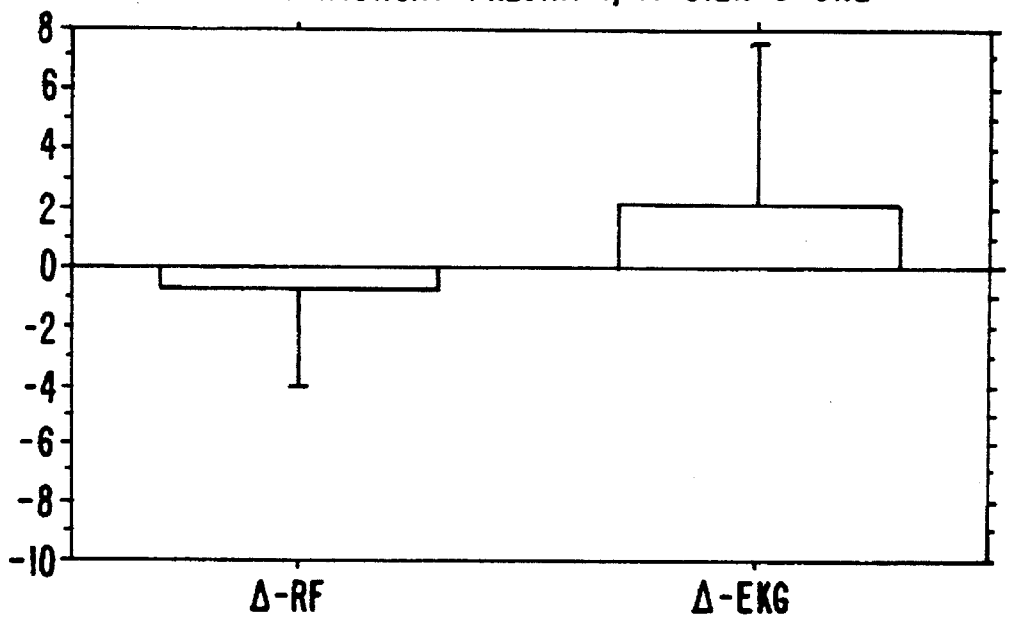
Figure 50:
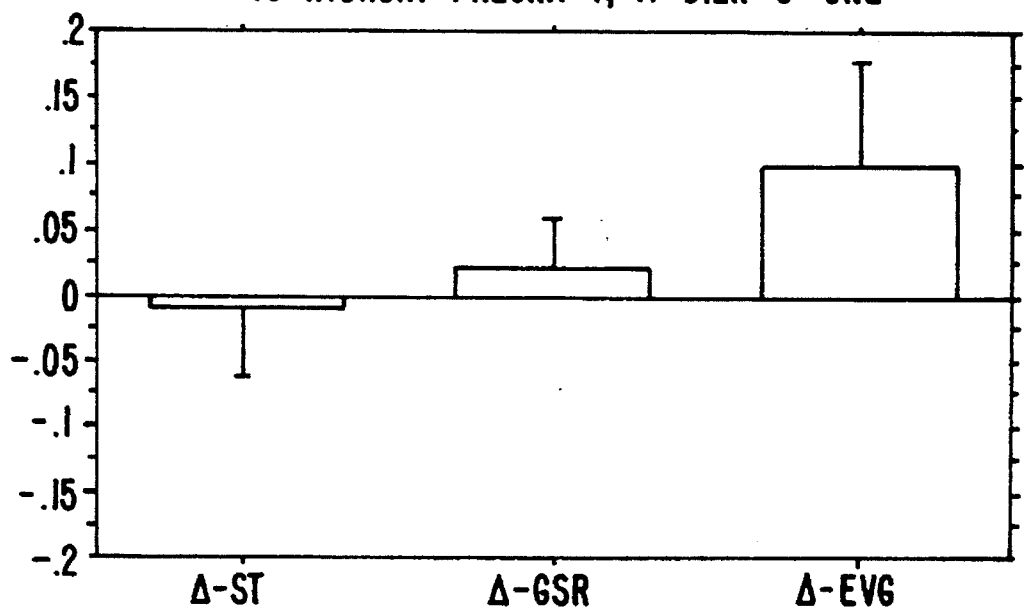
FIGS. 50, 51 and 52 show the ST, GSR, EVG, RF, EKG and EEG measurements in females of compound A7-P2.
Figure 51:
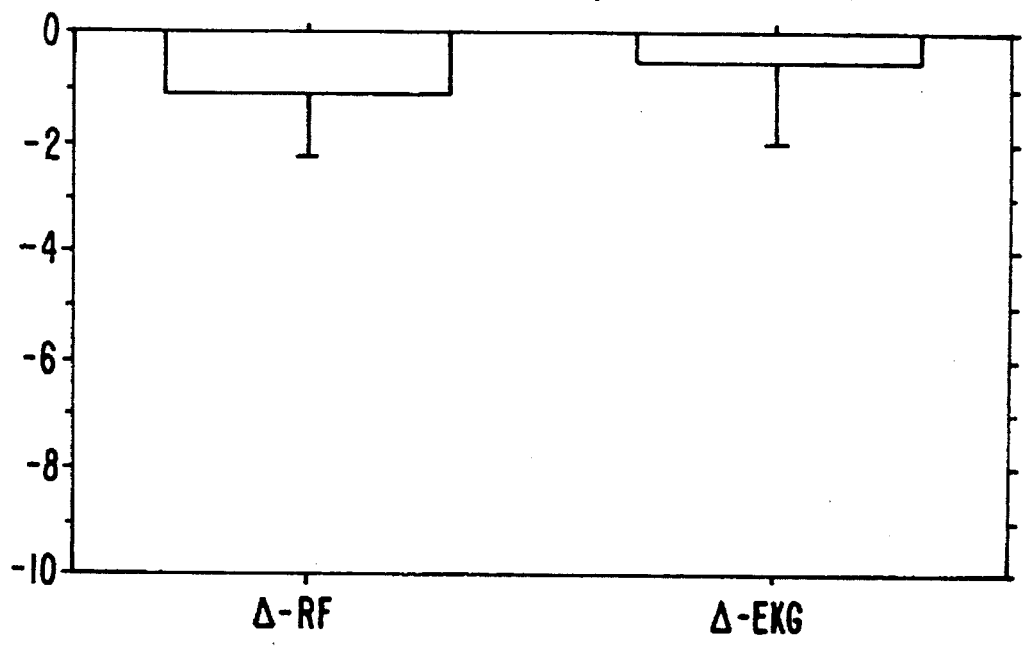
Figure 52:
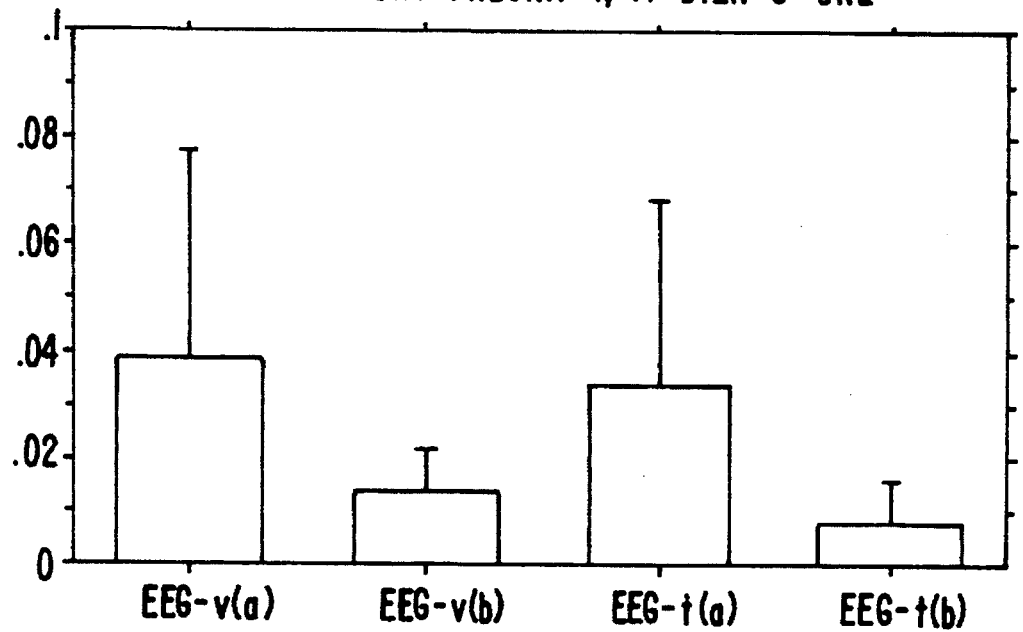
Figure 53:
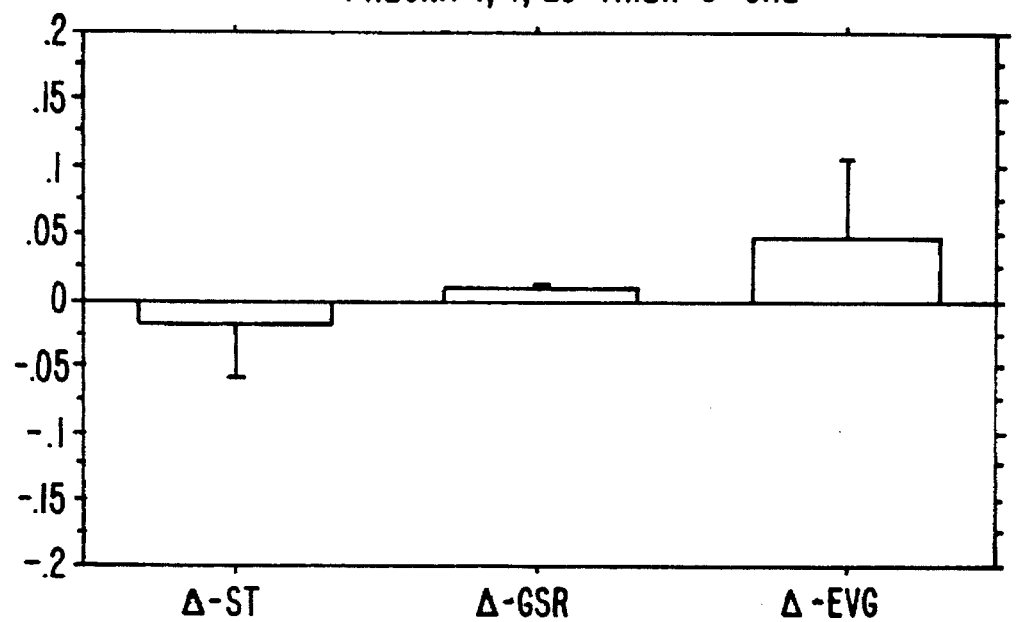
FIGS. 53 and 54 show the ST, GSR, EVG, EEG measurements in males of compound A11-P1.
Figure 54:
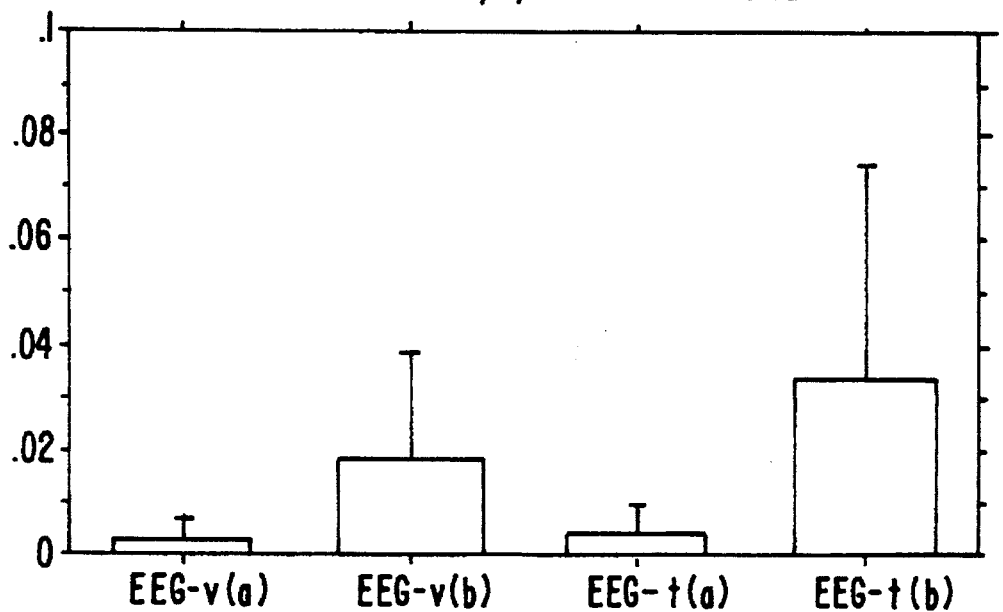
Figure 55:
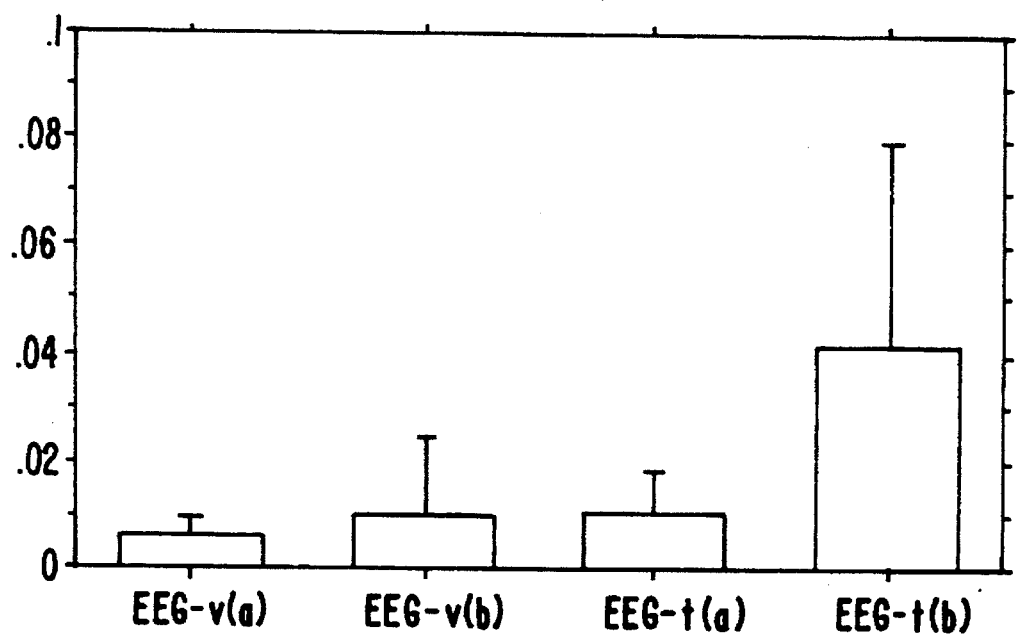
FIG. 55. shows the data of EEG measurements in males of compound A13-P1.
Figure 56:
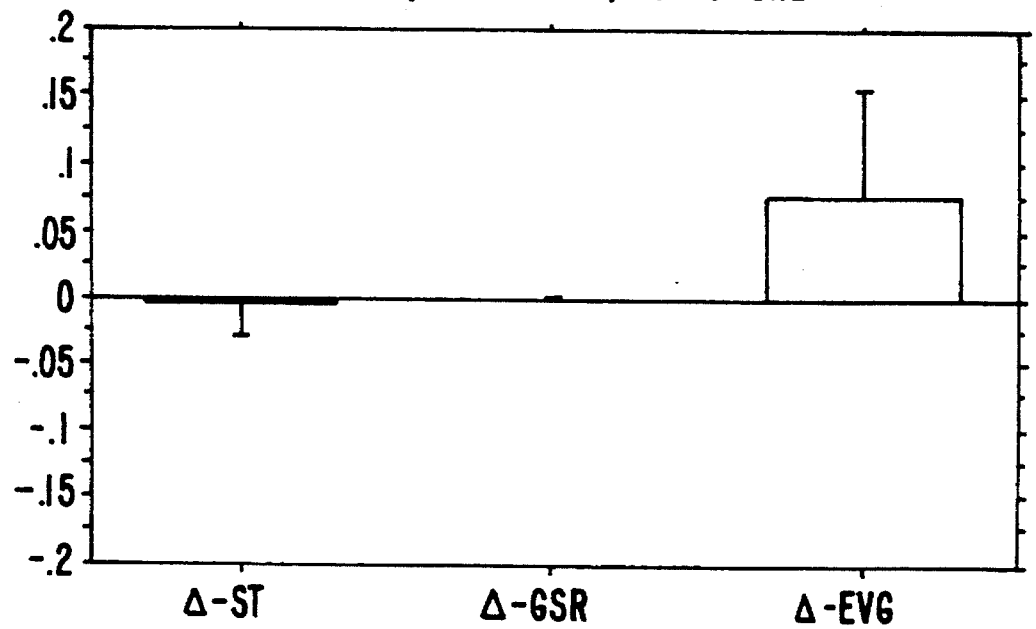
FIGS. 56, 57 and 58 show the data of measurements of ST, GSR, EVG, RF, EKG and EEG in females of compound A13-P1.
Figure 57:
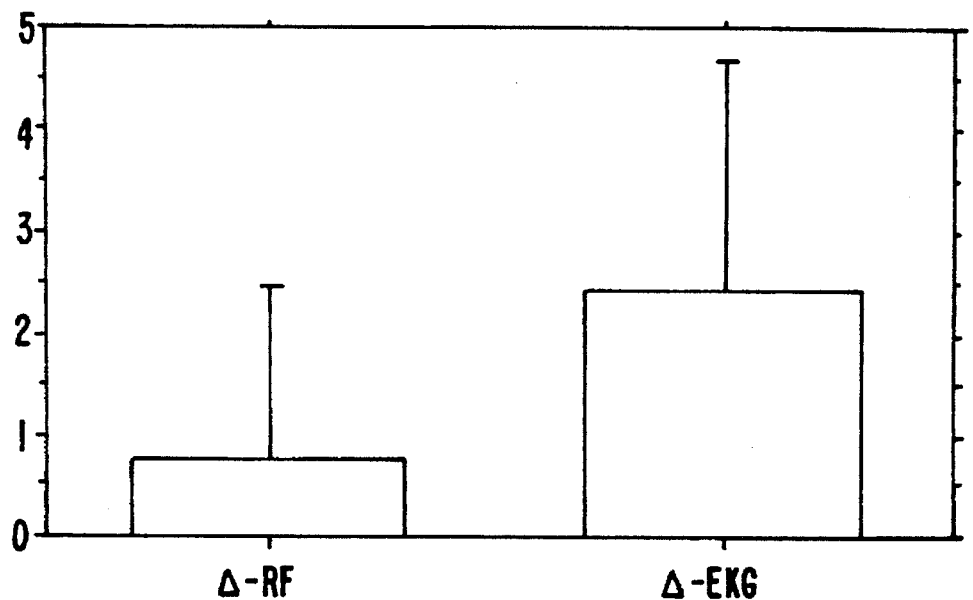
Figure 58:
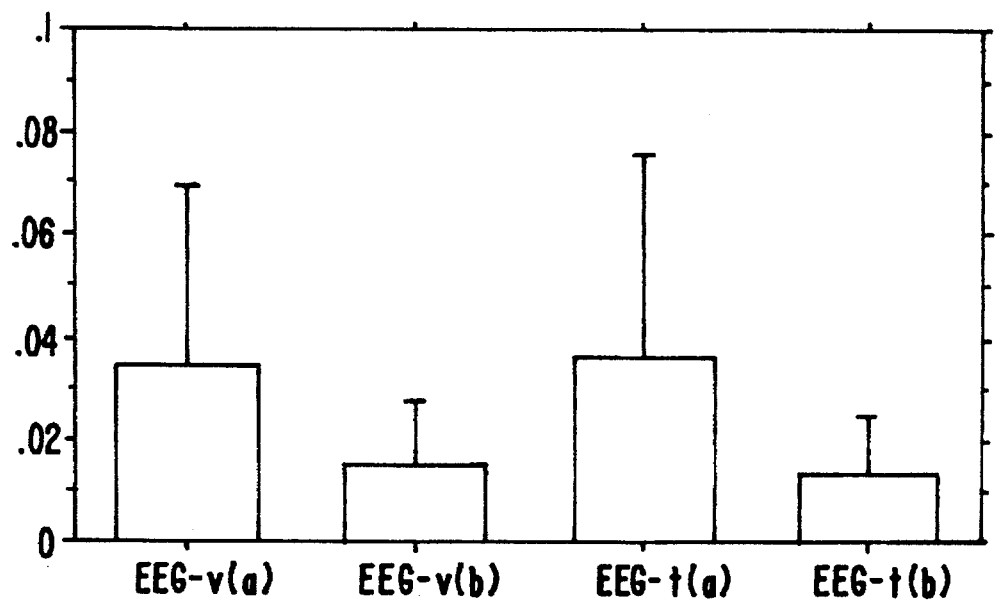

| | |
|---|---|
| A1-P3 | Pregna-4,16-dien-3-one |
| A2-P3 | Pregna-5,16-dien-3β-ol |
| A8-P1 | 3-Methoxy-pregna-3,5,20-triens |
| A6-P1 | Pregna-4,20-dien-3,6-dione |
| | 20,21-Dimethylpregna-5,20-dien-3β-01 |
| | 20,21-Dimethylpregna-5,20-dien-3-one |
| A14-P2 | 6β,19-Epoxypregna-4,17-dien-3-one |
| A7-P2 | 19-Hydroxy-pregna-4,17(20)-dien-3-one |
| A13-P1 | Pregna-4,20-dien-6β-ol-3-one |
| A11-P1 | Pregna-1,4,20-trien-3-one |
| A1-P1 | Pregna-4,20-dien-3-one |
| A2-P1 | Pregna-5,20-dien-3β-ol |
| A4-P1 | Pregna-4,20-3α-ol |
| A3-P1 | Pregna-4,20-3β-ol |
| A1-P4 | Pregn-4-en-3-one |
| A2-P4 | Pregn-5-en-3β-ol | was administered to 24 female and 24 male subjects using the procedure described in Example 17. Propylene glycol was also administered as a control. When compared to a propylene glycol control, the test compounds induced a significant change in the integrated receptor potential in the VNO, galvanic skin response (GSR), skin temperature (ST), the percentage of cortical alpha wave activity as measured by electroencephalogram (EEG), electrocardiogram (EKG) and respiratory frequency (RF). The results are shown in FIGS. 2 through 58.

Example 17

Electrophysiological Studies

The following electrophysiological studies were performed in clinically normal human volunteers of both sexes whose ages ranged from 20 to 45 years. No anesthetics were used, and female subjects were excluded if pregnant.

The stimulation and recording system consists of a "multifunctional miniprobe" described elsewhere (Monti-Bloch, L. and Grosser, B.l. (1991) "Effect of putative pheromones on the electrical activity of the human vomeronasal organ and olfactory epithelium," *J. Steroid Biochem. Molec. Biol.* 39:573–582.). The recording electrode is a 0.3 mm silver ball attached to a small (0.1 mm) silver wire insulated with Teflon© the surface of the electrode is first treated to produce a silver chloride interface, and is then covered with gelatin It is positioned within a small caliber Teflon© catheter (dia=5 mm) such that the tip of the electrode protrudes approximately 2 mm. The Teflon© catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon® tube with a diameter of 2 mm surrounds the catheter-electrode assemblage, and its central end is connected to an aspirator that provides continuous suction of 3 ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNO, or on the surface of the olfactory or respiratory epithelium.

Electro-vomeronasogram (EVG):

Recordings are carried out in a quiet room with the subject supine; the multi-functional miniprobe is initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6× magnifying binocular loupe with halogen illumination is then used to introduce the tip of the Teflon© catheter and recording electrode assemblage into the VNO opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. The integrated EVG is shown in FIGS. 1 and 2 for compounds A1-P1, A2-P1, A4-P1, A3-P1, A1-P 4, A2-P4 (referring to the chart). Artifacts produced by respiratory movements are deleted by training the subjects to practice mouth breathing with velopharyngeal closure. Samples of vomeropherins in concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon©, glass or stainless steel and are carefully cleaned and sterilized before each use. Activity was recorded using standard electroencephalographic (EEG) electrodes placed at positions Cz-A1 and Tz-A1 of the international 10120 system; the ground electrode was placed on the mastoid process. Skin temperature (ST) was recorded by a small (1.0 mm) thermistor probe placed in the right ear lobe. Respiratory frequency (RF) was measured with an adjustable strain gauge placed around the lower thorax. All electrical signals were DC amplified, digitized (MP-100, Biopac Systems) and continuously monitored utilizing a computer.

Statistical Analysis:

EVGs, peak-to-peak changes and frequency changes of other parameters were measured and statistically analyzed. The significance of the results was determined by either using paired t-tests or analysis of variance (ANOVA).

Reflex Effects of Vomeropherins:

Studies were conducted to determine the central nervous system (CNS) reflex responses to vomeropherin stimulation of the VNO. The sexually dimorphic local responses induced by vomeropherins were mirrored in the autonomic response of male & female subjects.

Cortical activity was recorded from Cz and Tz in male and female subjects during application to the VNO of air pulses (300 ms to 1 sec) containing 200 fmoles of vomeropherin. There is also preliminary evidence that the EVG is not associated with trigeminal nociceptor endings since application of a local anesthetic (2% lidocaine) to the respiratory epithelium of the nasal septum neither blocks nor diminishes the EVG (Monti-Bloch, L. and Grosser, B.l. (1991) "Effect of putative pheromones on the electrical activity of the human vomeronasal organ and olfactory epithelium,"*J. Steroid Biochem. Molec. Biol.* 39:573–582.), also, subjects failed to report sensations of pain as a consequence of any of the stimulation procedures.

We claim:

1. A pharmaceutical composition suitable for nasal administration in an individual, said composition comprising asteroid and a pharmaceutically acceptable carrier, wherein said steroid has the formula:

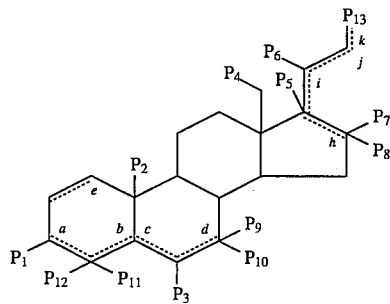

wherein $P_1$ is selected from the group consisting of oxo, α-(β-)hydroxy, α-(β-)acetoxy, α-(β-)propionoxy, α-(β-)methoxy, α-(β-)lower acyloxy, α-(β-)lower alkyloxy, and α-(β-)benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, oxo, halo, hydroxy, alkoxy, and acyloxy; $P_4$ through $P_{12}$ may each be, independently, hydrogen, halo, methyl, or halo-, dihalo- or perhalomethyl; $P_{13}$ is hydrogen, methyl, methylene, halo-substituted methyl or halo-substituted methylene; and "a", "b", "c", "d", "e", "h", "i", "j" and "k" are alternative sites for optional double bonds and "j" may also be a triple bond; and when $P_2$ is methyl and $P_3$ is β-hydroxy, $P_2$ and $P_3$ may be joined to form a cyclic ether.

2. A composition according to claim 1 wherein "b" is a double bond.

3. A composition according to claim 2 wherein "e" or "d" is a double bond.

4. A composition according to claim 1 wherein "a" and "c" are double bonds.

5. A composition according to claim 1 wherein "h" is an optional double bond, and "i" and "j" are absent.

6. A composition according to claim 1 wherein "j" is a double bond.

7. A composition according to claim 1 wherein "j" is a triple bond.

8. The pharmaceutical composition of any of claims 1 through 7 wherein said steroid is dissolved in said carrier.

9. The pharmaceutical composition of any of claims 1 through 7 wherein said composition is in a liquid form.

10. The pharmaceutical composition of any of claims 1 through 7 wherein said composition further contains a pharmaceutically acceptable ointment base.

11. The pharmaceutical composition of any of claims 1 through 7 which contains no more than one of said steroids.

12. The pharmaceutical composition of any of claims 1 through 7 which contains more than one of said steroids.

13. A method of altering a hypothalamic function of an individual, said method comprising:

providing a pregnane derivative on the surface of nasal neuroepithelial cell of said individual wherein said cell is a part of tissue other than olfactory epithelia; and, administering said pregnane derivative within a nasal passage of said individual such that said pregnane derivative binds specifically to said surface and results in an alteration of hypothalamic function of said individual.

14. A method of altering an autonomic function of an individual, said method comprising:

providing a pregnane derivative for a chemoreceptor of a nasal neuroepithelial cell of said individual wherein said cell is a part of tissue other than olfactory epithelia; and, administering said pregnane derivative within a nasal passage of said individual such that said pregnane derivative binds specifically to said receptor and results in an alteration of autononic function of said individual.

15. The method of claim 13 or 14 wherein said neuroepithelial cell is located within a vomeronasal organ of said individual.

16. The method of claim 15 wherein said pregnane is of the formula:

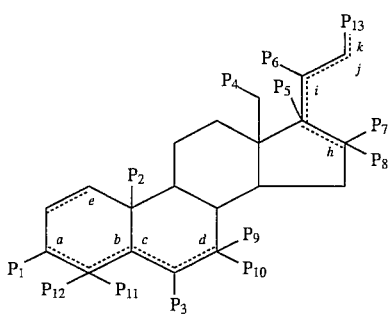

wherein $P_1$ is selected from the group consisting of oxo, α-(ε-)hydroxy, α-(β-)acetoxy, α-(β-)propionoxy, α-(β-) methoxy, α-(β-)lower acyloxy, α-(β-)lower alkyloxy, and α-(β-)benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, oxo, halo, hydroxy, alkoxy, and acyloxy; $P_4$ through $P_{12}$ may each be, independently, hydrogen, halo, methyl, or halo-, dihalo- or perhalomethyl; $P_{13}$ is hydrogen, methyl, methylene, halo-substituted methyl or halo-substituted methylene; and "a", "b", "c", "d", "e", "h", "i", "j" and "k" are alternative sites for optional double bonds and "j" may also be a triple bond; and when $P_2$ is methyl and $P_3$ is β-hydroxy, $P_2$ and $P_3$ may be joined to form a cyclic ether.

17. A method according to claim 16 wherein "b" is a double bond.

18. A method according to claim 17 wherein claim 17 or "e" or "d" is a double bond.

19. A method according to claim 16 wherein "a" and "c" are double bonds.

20. A method according to claim 16 wherein "h" is an optional double bond, and "i" and "j" are absent.

21. A method according to claim 16 wherein is a double "j" is a double bond.

22. A method according to claim 16 wherein "j" is a triple bond.

23. The method of claim 15 wherein the amount of said pregnane derivative that is administered is at least about 100 picograms, but no more than about 100 micrograms.

24. The method of claim 23 wherein the amount of said pregnane derivative that is administered is at least about 1 nanograms, but no more than about 10 micrograms.

25. The method of claim 24 wherein the amount of said pregnane derivative that is administered is at least about 10 nanograms, but no more than about 1 microgram.

26. The method of claim 13 or 14 further comprising one step of preparing a pharmaceutical composition of said pregnane derivative dissolved in a pharmaceutically acceptable carrier.

27. The method of claim 26 wherein said pharmaceutical composition is an ointment.

28. The method of claim 26 wherein said pharmaceutical composition is liquid.

29. The method of claim 26 wherein the administration is by aerosol.

30. The method of claims 13 or 14 wherein more than one pregnane steroid is administered.

* * * * *

UNITED STATES PATENT AND TRADEMARK OFFICE
CERTIFICATE OF CORRECTION

PATENT NO. : 5,563,131
DATED : October 8, 1996
INVENTOR(S) : Berliner, et al

It is certified that error appears in the above-identified patent and that said Letters Patent is hereby corrected as shown below:

In column 60, line 67, change "0.61" to read -- $R_f$ 0.61 --.

In column 61, line 25, change "3-ol" to read -- 3$\beta$-ol --.

Signed and Sealed this

Third Day of March, 1998

Attest:

BRUCE LEHMAN

*Attesting Officer*  *Commissioner of Patents and Trademarks*